US008703707B2

(12) United States Patent
Sakmar et al.

(10) Patent No.: US 8,703,707 B2
(45) Date of Patent: Apr. 22, 2014

(54) NUCLEOBINDIN I VARIANT PROTEIN COMPOSITIONS AND METHODS OF USE

(75) Inventors: Thomas P. Sakmar, New York, NY (US); Santosh T. Menon, Edgewater, NJ (US); Neeraj Kapoor, New York, NY (US); Ruchi Gupta, New York, NY (US); Dan Raleigh, Stony Brook, NY (US)

(73) Assignees: The Rockefeller University, New York, NY (US); The Research Foundation of State University of New York, Albany, NY (US)

( * ) Notice: Subject to any disclaimer, the term of this patent is extended or adjusted under 35 U.S.C. 154(b) by 33 days.

(21) Appl. No.: 13/054,263

(22) PCT Filed: Jul. 16, 2009

(86) PCT No.: PCT/US2009/050873
§ 371 (c)(1),
(2), (4) Date: May 20, 2011

(87) PCT Pub. No.: WO2010/009330
PCT Pub. Date: Jan. 21, 2010

(65) Prior Publication Data
US 2011/0224143 A1    Sep. 15, 2011

Related U.S. Application Data

(60) Provisional application No. 61/081,589, filed on Jul. 17, 2008.

(51) Int. Cl.
*A61K 38/00* (2006.01)
*A61P 13/12* (2006.01)

(52) U.S. Cl.
USPC ...................................................... 514/15.4

(58) Field of Classification Search
None
See application file for complete search history.

(56) References Cited

U.S. PATENT DOCUMENTS

2008/0115231 A1 *   5/2008  Mori et al. ..................... 800/3

FOREIGN PATENT DOCUMENTS

EP      1900813 A1 *  3/2008
WO      2010/009330 A1    1/2010

OTHER PUBLICATIONS

Roberts et al. (Advanced Drug Delivery Reviews, 2002, 54, 459-476).*
Terpe (Appl. Microbiol. Biotechnol. 2003, 60:523-533).*
International Search Report and Written Opinion for PCT/US2009/050873 dated Dec. 2, 2009.
Lin et al., "Calnuc Binds to Alzheimer's Beta-Amyloid Precursor Protein and Affects its Biogenesis", Journal of Neurochemistry, Mar. 2007, pp. 1505-1514, Vol. 100, No. 6.
Gupta, "Study of Factors Affecting Amylin Fibril Formation and the Characterization of a Protein which Prevents Amyloidogenesis". Doctoral Thesis, published by the Graduate School, Stony Brook University: Stony Brook, NY online at <http://dspace.sunyconnect.suny.edu/handle/1951/45453>, submitted May 2008, Issued Aug. 1, 2008, date available Feb. 12, 2010.
De Alba et al., "Structural Studies on the Ca2+-binding Domain of Human Nucleobindin (Calnuc)", Biochemistry, 2004, pp. 10039-10049, vol. 43, No. 31.
Gifford et al., "Structures and Metal Ion-Binding Properties of the Ca2+-binding helix-loop-helix EF-hand Motifs", The Journal of Biochemistry, 2007, pp. 199-221, vol. 405.
Grabarek, "Structural Basis for Diversity of the EF-hand Calcium-binding Proteins", Journal of Molecular Biology, 2006, pp. 509-525, vol. 359.
International Preliminary Report on Patentability (Chapter I) for PCT/US2009/050873 dated Jan. 18, 2011.
Kapoor et al, "Nucleobindin 1 is a Calcium-Regulated Guanine Nucleotide Dissociation Inhibitor of G alphai 1", The Journal of Biological Chemistry, 2010, pp. 31467-31660, vol. 285, No. 41.
Lin et al., "Overexpression of CALNUC (Nucleobindin) Increases Agonist and Thapsigargin Releasable Ca2+ Storage in Golgi", The Journal of Cell Biology, 1999, pp. 279-289, vol. 145, No. 2.
Lin et al., "The Mammalian Calcium-Binding Protein, Nucleobindin (CALNUC), is a Golgi Resident Protein", The Journal of Cell Biology, 1998, pp. 1515-1527, vol. 141, No. 7.
Miura et al., "Calcium-Binding Activity of Nucleobindin Mediated by an EF Hand Moiety", Biochemical and Biophysical Research Communications, 1994, pp. 1388-1393, vol. 99, No. 3.
Valencia et al., "Modulation of Nucleobindin-1 and Nucleobindin-2 by Caspases", FEBS Lett., 2008, pp. 286-290, vol. 582, No. 2.

* cited by examiner

*Primary Examiner* — Marcela M Cordero Garcia
*Assistant Examiner* — Kaipeen Yang
(74) *Attorney, Agent, or Firm* — Thompson Coburn LLP; Charles P. Romano

(57) ABSTRACT

The invention relates to Nucleobindin-1 (NUCB1) protein variants that are capable of disaggregating amyloid fibrils as well as inhibiting the formation of fibrils in the presence of physiological concentrations of calcium. Isolated NUCB1 protein variants, nucleic acids encoding the protein variants, cells comprising the isolated nucleic acids, pharmaceutical compositions and kits comprising the variants, methods of making the variants, and therapeutic uses of the variants are provided.

23 Claims, 29 Drawing Sheets

FIG.3A,B

```
NUCB1EF1/1-12  D I N S D G V L D E Q E
NUCB1EF2/1-12  D T N Q D R L V T L E E
CaMEF4/1-12    D I D G D G Q V N Y E E
CaMEF2/1-12    D A D G N G T I D F P E
CaMEF3/1-12    D K G G N G Y I S A A E
CaMEF1/1-12    D K D G D G T I T T K E
```

FIG. 7

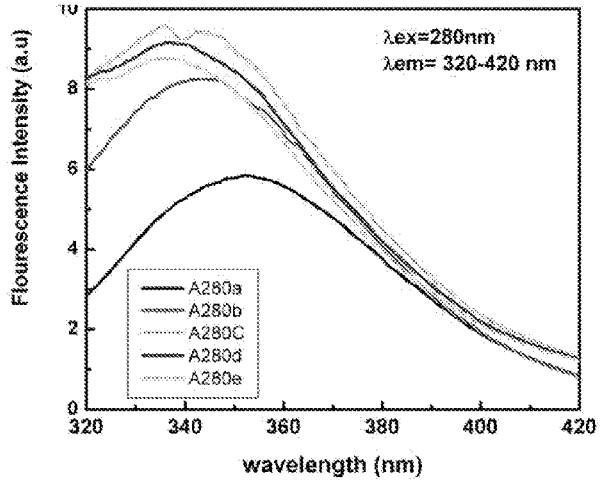
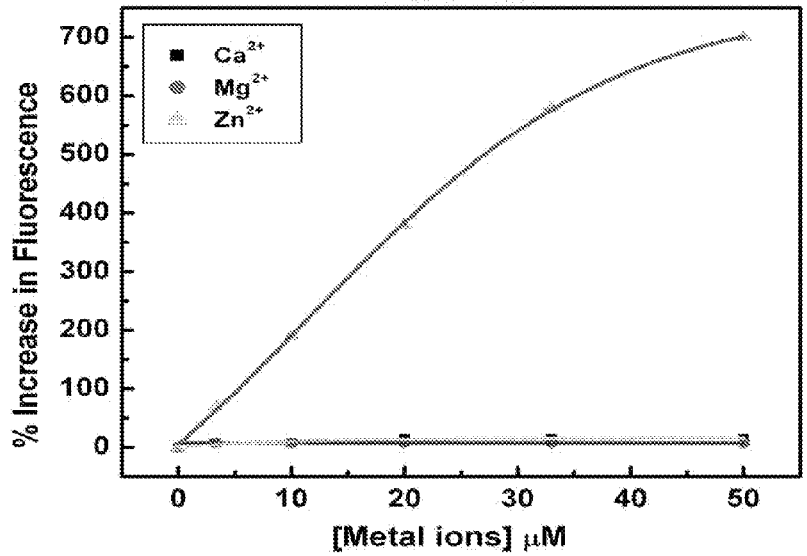
FIG. 26

NUCLEOBINDIN I VARIANT PROTEIN COMPOSITIONS AND METHODS OF USE

CROSS-REFERENCE TO RELATED APPLICATIONS

This application is a National Stage application of International Patent Application No. PCT/US2009/050873, filed Jul. 16, 2009 and incorporated by reference herein in its entirety, which claims the benefit of U.S. Provisional Patent Application Ser. No. 61/081,589, filed on Jul. 17, 2008 and incorporated herein by reference in its entirety.

STATEMENT REGARDING FEDERALLY SPONSORED RESEARCH OR DEVELOPMENT

This invention was made with government support under grant number GM078114 awarded by the National Institute of Health. The government has certain rights in the invention.

INCORPORATION OF SEQUENCE LISTING

A computer readable form of the sequence listing is provided herein, containing the file named "49248_93134_SEQ_LST.txt", which is 82248 bytes in size (measured in MS-DOS), and is herein incorporated by reference in its entirety. This Sequence Listing consists of SEQ ID NOs: 1-39.

BACKGROUND OF THE INVENTION

Amyloid fibril formation has been implicated in approximately 25 different diseases including Type 2 diabetes, Alzheimer's disease and Parkinson's disease. The proteins involved in each of these diseases show no sequence or structural homology. The proteins like Amylin associated with Type 2 diabetes and Amyloid Beta (Aβ) associated with Alzheimer's disease are natively unstructured. The aggregation of these proteins initially involves a structural rearrangement of monomers to form the nucleus, which then serves as a template for the addition of monomers/oligomers for fibril growth. The rates of nucleus formation as well as the growth of fibrils vary from peptide to peptide and depend on the conditions used.

The manifestation of prefibrillar and fibrillar species comprising amyloid proteins has been shown to be toxic to cells. In addition to cell death, aggregation of these normally soluble proteins makes them unavailable for the execution of their normal physiological functions. The association of these aggregates with pathogenesis of the disease has stimulated great interest in searching for molecules that can inhibit their formation. Such treatments available can either slow down the progression of the disease or simply manage the symptoms. However an effective therapeutic aid that can cure Alzheimer's disease or amyloid formation in Type 2 diabetes still remains to be established. During the past decade, several small molecules have been discovered that decrease the amyloid load in the brain and seen to partially reverse the cognitive impairment. They function either by preventing the association of the protein monomers or interfere with the pathways involved in generating the amyloidogenic peptides like Aβ. Several chaperones such as heat shock proteins (Hsps) and small heat shock proteins (sHsps) have also been shown to inhibit aggregation. Hsp 104 inhibits the fibrillization of Sup35 prion conformers. Several members of sHsps like αB-crystallin, Hsp27, Hsp20 and HspB8 bind to Aβ40 and Aβ42 and completely inhibit the aggregation of Aβ40 into mature fibrils. The small heat shock proteins bind to prefibrillar species and inhibit their progression to amyloid fibrils (Wilhelmus et al., Brain Research, 1089, 67-78, 2006; Wilhelmus et al., Acta Neuropathol., 111, 139-149, 2006).

Calnuc or Nucleobindin 1 (NUCB1) is a 55 kDa protein, which was first reported to be a growth and differentiation factor associated with lupus syndrome (Kanai et al., Immunol. Lett., 32, 43-48, 1992). Calnuc acquires its name from its DNA-binding and calcium binding ability. Its domain structure comprises, from N-terminus to C-terminus, a signal sequence at its N-terminus followed by a DNA binding domain of basic residues, an N-terminal proximal EF hand domain comprising a helix-loop-helix motif, an intervening acidic region, a second C-terminal proximal EF hand domain comprising a helix-loop-helix motif, and a leucine zipper domain (Miura et al., Biochem. Biophys. Res. Commun., 187, 375-380, 1992). Both the DNA binding domain and leucine zipper are crucial for binding of NUCB1 to DNA.

NUCB1 has been postulated to be involved in several important cellular functions. However, the pathways associated with the functionality of NUCB1, which require its conservation across the animal kingdom, still remain to be deciphered. Since its discovery, NUCB1 has been reported to be widely expressed in cells and tissues and is conserved from flies to humans (Kawano et al., Eur. J. Cell Biol. 79, 208-217, 2000). This suggests that NUCB1 is an essential calcium binding protein present in the eukaryotic genome. NUCB1 is primarily a golgi resident protein found in both cytosolic and membrane fractions (Lin et al., J. Cell Biol., 141, 1515-1527, 1998). $^{45}Ca2+$-binding assays with golgi fractions revealed NUCB1 to be the major calcium binding protein in golgi. In fact, NUCB1 shows high homology with the ER resident protein Calreticulin and displays similar properties suggesting it has a role in both calcium storage and homeostasis in golgi. Osteocytes and osteoblasts have also been reported to produce NUCB1 where it is thought to function as a modulator of matrix maturation during mineralization process in the bone (Petersson et al., Bone, 34, 949-60, 2004). The calcium binding ability of NUCB1 was found to cause accumulation and transport of Ca2+ ions to the mineralization front before hydroxyapatite deposition in bones (Somogyi et al., Calcif Tissue Int., 74, 3 66-76, 2004).

The structural basis of NUCB1 calcium binding activity has also been studied. Miura et al., reported that a C-terminal deletion of 166 residues of NUCB1 that contained only the N-terminal EF hand domain could bind calcium while a C-terminal deletion of 208 residues of NUCB1 that lacked both EF hand domains could not bind calcium (Miura et al., Biochem Biophys Res Commun. 1994 Mar. 30; 199(3):1388-93). Lin et al., disclosed an N-terminally truncated NUCB1 mutant where both EF hand loop domains and the intervening acidic region had been deleted and speculated that other acidic regions of the C-terminal domain of NUCB1 may contain low affinity calcium binding sites (Lin et al., J. Cell Biol. 141 (7): 1515. (1998). Lin et al. also subsequently reported that deletion of the entire N-terminal EF-hand (EF-1) loop domain or deletion of both EF loop hand domains and intervening acidic region of a Rat NUCB1-GFP fusion protein eliminated calcium binding (Lin et al., J Cell Biol. 1999 Apr. 19; 145(2):279-89). This same report by Lin et al. further suggested that the Rat NUCB1 protein had a single high affinity, low capacity calcium binding domain corresponding to the N-terminal (EF-1) domain.

As a first step in understanding the ubiquitous nature of NUCB1, the pathway of secretion for this protein was investigated through pulse-chase experiments. It was found that NUCB1 is synthesized in the ER and then transported to the Golgi where it resides for more than 12 hours. In the Golgi, NUCB1 undergoes O-glycosylation and sulfation and is then secreted into the extracellular medium via the constitutive-like pathway (Lavoie et al., Mol. Endocrinol., 16, 2462-74, 2002). Interactions with Cox-1 and Cox-2 isozymes have been shown to be involved in the retention of NUCB1 in the ER (Ballif et al., Proc. Natl. Acad. Sci., 93, 5544-9, 1996). NUCB1 has also been shown to interact with the $G\alpha_i$; and $G\alpha_s$ subunits of heterotrimeric G-proteins and has been postulated to participate in regulating downstream signaling (Lavoie et al., Mol. Endocrinol., 16, 2462-74 2002).

Recent studies have suggested that overexpression of NUCB1 down-regulates the mRNA production of Amyloid precursor protein (APP) and inhibits its biosynthesis (Lin et al., J. Neurochem., 100, 1505-14, 2007). Aggregation of Aβ isoforms generated from the sequential proteolytic cleavage of APP by β-(Beta Amyloid Cleaving Enzyme-1) and γ-secretase has been well characterized in Alzheimer's disease. In addition, abnormal calcium homeostasis has also been observed in the brains of demented patients. One study indicated that: i) NUCB1 binds to APP in a calcium dependent manner where binding is inhibited by Ca+2; ii) NUCB1 co-localizes with APP in vivo; iii) NUCB1 regulates APP protein levels by affecting APP synthesis; and that iv) the expression level of NUCB1 is decreased in the brains of Alzheimer's disease patients by 50% (Lin et al., J. Neurochem., 100, 1505-14, 2007). Nonetheless, Lin et al., (J. Neurochem., 100, 1505-14, 2007) did not indicate that NUCB1 could disaggregate amyloid fibrils or inhibit amyloid fibril formation.

SUMMARY OF INVENTION

Provided herein are NUCB1 protein variants capable of disaggregating fibrillar deposits comprised of amyloid proteins in the presence of calcium. Also provided herein are NUCB1 protein variants capable of disaggregating fibrillar deposits comprised of amyloid proteins in any of either the absence of calcium or subphysiological levels of calcium. In addition to these NUCB1 protein variants, methods of making NUCB1 protein variants, pharmaceutical and veterinary compositions comprising NUCB1 protein variants, kits comprising NUCB1 protein variants, methods of treating amyloidosis, methods of disaggregating amyloid fibrils, and methods of inhibiting amyloid fibril formation are also provided.

In certain embodiments, a nucleobindin 1 (NUCB1) protein variant comprising an EF hand loop 1 domain, an intervening acidic region, an EF hand loop 2 domain, and wherein said protein variant displays amyloid fibril disaggregation activity and/or amyloid fibril formation inhibitory activity is provided. In other embodiments, the NUCB1 protein variant contains at least one mutation. In certain embodiments, NUCB1 protein variants of the invention can comprise at least one substitution mutation and/or deletion mutation of six amino acids or less in a single loop region of an EF hand domain of the NUCB1 protein variant. In other embodiments, isolated proteins comprising a nucleobindin 1 (NUCB1) protein variant that comprises at least one mutation in each loop region of each EF hand domain of the NUCB1 protein variant are provided, where the NUCB1 protein variant does not include a deletion of an entire 12 amino acid loop region of both EF-hand domains and intervening acidic region, and where the mutations in the loop regions inhibit calcium binding to the NUCB1 protein variant are provided. In other embodiments, isolated proteins comprising a nucleobindin 1 (NUCB1) protein variant that comprises at least one mutation in each loop region of each EF hand domain of the NUCB1 protein variant are provided, where the NUCB1 protein variant does not include a deletion of either or both entire 12 amino acid loop EF-hand domains and/or intervening acidic region, and where the mutations in the loop regions inhibit calcium binding to the NUCB1 protein variant are provided. NUCB1 protein variants can be a human NUCB1 protein variant or a humanized NUCB1 protein variant. In certain embodiments, the NUCB1 protein variant comprises any of at least one substitution mutation in a loop region of one or both EF hand domain(s) of the NUCB1 protein variant, at least one deletion of no more than 1 to 6 amino acids in loop region(s) of one or both EF hand domain(s) of the NUCB1 protein variant, or a combination of the substitution mutations and the deletion mutations. In still other embodiments, the substitution mutation in the NUCB1 protein variant comprises a non-conservative substitution of an aspartate residue at position 1 in one or both EF hand domain loop region(s). A NUCB1 variant of the invention can also comprise a deletion mutation that comprises a deletion of an aspartate residue at position 1 in one or both EF hand domain loop region(s). In still other embodiments, the mutation can comprise a non-conservative substitution of a glutamate residue at position 12 of one or both EF hand domain loop region(s) or a deletion of a glutamate residue at position 12 of one or both EF hand domain loop region(s). In other embodiments, the mutation can comprise a non-conservative substitution of an asparagine residue at position 3 in one or both EF hand domain loop region(s) or a deletion of an asparagine residue at position 3 of one or both EF hand domain loop region(s). In other embodiments, the mutation can comprise a non-conservative substitution of aspartate residue at position 5 in one or both of the EF hand domain loop region(s) or a deletion of an aspartate residue at position 5 in one or both EF hand domain loop region(s).

NUCB1 protein variants provided herein can also comprise a N-terminal proximal EF hand loop region of the SEQ ID NO:7 and/or a C-terminal proximal EF hand loop region of SEQ ID NO:8, wherein at least one residue in SEQ ID NO:7 is distinct from a corresponding residue of SEQ ID NO:9, and/or wherein at least one residue in SEQ ID NO:8 is distinct from a corresponding residue of SEQ ID NO:10. In certain embodiments, $Xaa_1$ of SEQ ID NO:7 and/or SEQ ID NO:8 is selected independently from alanine, serine, lysine, or arginine. In other embodiments, $Xaa_3$ of SEQ ID NO:7 and/or SEQ ID NO:8 is selected independently from lysine or arginine. In still other embodiments, $Xaa_5$ of SEQ ID NO:7 and SEQ ID NO:8 is selected independently from lysine or arginine. In still other embodiments, $Xaa_{12}$ of SEQ ID NO:7 and/or SEQ ID NO:8 is selected independently from alanine, serine, lysine, or arginine. The NUCB1 protein variant can also comprise a protein where $Xaa_1$ of SEQ ID NO:7 and/or SEQ ID NO:8 is selected independently from lysine or arginine, where $Xaa_3$ of SEQ ID NO:7 and/or SEQ ID NO:8 is selected independently from lysine or arginine, where $Xaa_5$ of SEQ ID NO:7 and/or SEQ ID NO:8 is selected independently from lysine or arginine, and wherein $Xaa_{12}$ of SEQ ID NO:7 and/or SEQ ID NO:8 is selected independently from alanine, lysine, or arginine. Also provided herein are NUCB1 protein variants where $Xaa_1$ of both SEQ ID NO:7 and SEQ ID NO:8 is lysine and wherein $Xaa_{12}$ of both SEQ ID NO:7 and SEQ ID NO:8 is alanine. Still other NUCB1 protein variants provided herein can comprise first N-terminal proximal EF hand loop region of SEQ ID NO: 11 and/or a second C-terminal proximal EF hand loop region of SEQ ID NO:12. In still other embodiments, NUCB1 protein variants provided herein comprise SEQ ID NO:6. In still other embodiments, NUCB1 protein variants provided herein comprise SEQ ID NO:1 and any of the aforementioned substitution or deletion mutations in residues of SEQ ID NO:1 that correspond to the EF hand loop domain of SEQ ID NO:7 and/or the EF hand loop domain of SEQ ID NO:8.

In certain distinct embodiments or in any of the aforementioned embodiments, a NUCB1 protein variant can have a C-terminal deletion of 1 to about 128 C-terminal amino acids of a NUCB1 protein. NUCB1 protein variants with C-terminal deletions can comprise the polypeptide of SEQ ID NO: 27, SEQ ID NO: 29, or SEQ ID:31.

In certain distinct embodiments or in any of the aforementioned embodiments, a NUCB1 protein variant can have: i) a C-terminal deletion of 1 to about 61 C-terminal amino acids of an NUCB1 protein and ii) a N-terminal deletion of about 1 to about 232 N-terminal amino acids of a NUCB1 protein. NUCB1 protein variants with N- and C-terminal deletions can comprise the polypeptide of SEQ ID NO: 33.

In certain distinct embodiments or in any of the aforementioned embodiments, a NUCB1 protein variant has a N-terminal deletion of about 31 to about 232 N-terminal amino acids of a NUCB1 protein. A NUCB1 protein variant with an N-terminal deletion can comprise the polypeptide of SEQ ID NO:25.

Any of the aforementioned NUCB1 protein variants provided herein can further comprise an operably linked protease cleavage site, purification tag, signal peptide, or combination thereof. Any of the NUCB1 protein variant provided herein can also further comprise a chemical modification selected from the group consisting of amidation, lipidation, glycosylation, pegylation, and combinations thereof. Any of the aforementioned NUCB1 variant proteins provided herein can display increased amyloid fibril disaggregation activity and/or increase amyloid fibril formation inhibitory activity relative to the naturally occurring NUCB1 protein when calcium is present at a concentration of 200 micromolar to at least 3 mM. Any of the aforementioned NUCB1 variant proteins provided herein can display peptidase activity. Any of the aforementioned NUCB1 variant proteins provided herein that displays peptidase activity can comprise at least one carboxypeptidase motif. In any of the aforementioned NUCB1 variant proteins provided herein that displays peptidase activity that contain a carboxypeptidase motif, the carboxypeptidase motif can comprise a NQHTFEARDLELL motif (SEQ ID NO:21), a GLDPNRFNP motif (SEQ ID NO:22), a DGHFREKLQAA motif (SEQ ID NO:22), or a motif comprising one or more conservative substitutions of SEQ ID NO:21, SEQ ID NO:22, or SEQ ID NO:23.

Also provided herein are isolated nucleic acids comprising a polynucleotide sequence encoding any of the aforementioned nucleobindin 1 (NUCB1) protein variants provided herein. In certain embodiments, the isolated nucleic acid can comprise a polynucleotide sequence encoding a human nucleobindin 1 (NUCB1) protein variant, wherein the NUCB1 protein variant comprises an EF hand loop 1 domain, an intervening acidic region, an EF hand loop 2 domain, and wherein said NUCB1 protein variant displays amyloid fibril disaggregation activity and/or amyloid fibril formation inhibitory activity. In still other embodiments, the isolated nucleic acid can comprise a polynucleotide sequence encoding a human nucleobindin 1 (NUCB1) protein variant, wherein the NUCB1 protein variant comprises an EF hand loop 1 domain, an intervening acidic region, an EF hand loop 2 domain, and wherein said NUCB1 protein variant displays amyloid fibril disaggregation activity and/or amyloid fibril formation inhibitory activity, wherein said variant contains at least one mutation. In certain embodiments, the isolated nucleic acid encodes NUCB1 protein variants that comprise at least one mutation in each loop region of each EF hand domain of the NUCB1 protein variant, where the NUCB1 protein variant does not include a deletion of an entire 12 amino acid loop region of both EF-hand domains and intervening acidic region, and where the mutations in the loop regions inhibit calcium binding to the NUCB1 protein variant. In certain embodiments, the isolated nucleic acid encodes NUCB1 protein variants that comprise at least one mutation in each loop region of each EF hand domain of the NUCB1 protein variant, where the NUCB1 protein variant does not include a deletion of either or both entire 12 amino acid loop EF-hand domains and/or intervening acidic region, and where the mutations in the loop regions inhibit calcium binding to the NUCB1 protein variant. Isolated nucleic acids provided herein can encode NUCB1 protein variants comprising at least one substitution mutation in a loop region of an EF hand domain of the NUCB1 protein variant, at least one deletion of no more than 1 to 6 amino acids in a loop region of each EF hand domain of the NUCB1 protein variant, or a combination of the substitution mutations and the deletion mutations. In certain embodiments, isolated nucleic acids provided herein encode NUCB1 protein variants comprising a first N-terminal proximal EF hand loop region of the SEQ ID NO:7 and a first N-terminal proximal EF hand loop region of SEQ ID NO:8, wherein at least one residue in SEQ ID NO:7 is distinct from a corresponding residue of SEQ ID NO:9, and wherein at least one residue in SEQ ID NO:8 is distinct from a corresponding residue of SEQ ID NO:10. In other embodiments of isolated nucleic acids encoding NUCB1 protein variants that comprise a first N-terminal proximal EF hand loop region of the SEQ ID NO:7 and a first N-terminal proximal EF hand loop region of SEQ ID NO:8, $Xaa_1$ of SEQ ID NO:7 and/or SEQ ID NO:8 can be selected independently from lysine or arginine and $Xaa_{12}$ of both SEQ ID NO:7 and/or SEQ ID NO:8 can be selected independently from alanine, lysine, or arginine. In other embodiments, such isolated nucleic acids can encode a NUCB1 protein variant where $Xaa_1$ of both SEQ ID NO:7 and SEQ ID NO:8 is lysine and wherein $Xaa_{12}$ of both SEQ ID NO:7 and SEQ ID NO:8 is alanine. In still other embodiments, such isolated nucleic acids can encode a NUCB1 protein variant where the first N-terminal proximal EF hand loop region is SEQ ID NO:11 and where the second C-terminal proximal EF hand loop region is SEQ ID NO:12. In still other embodiments, the isolated nucleic acid encodes a NUCB1 protein variant that comprises SEQ ID NO:6. In still other embodiments, isolated nucleic acids provided herein can encode NUCB1 protein variants that comprise SEQ ID NO:1 and any of the aforementioned substitution or deletion mutations in residues of SEQ ID NO:1 that correspond to the EF hand loop domain of SEQ ID NO:7 and/or the EF hand loop domain of SEQ ID NO:8.

In certain distinct embodiments or in any of the aforementioned embodiments, an isolated nucleic acid encoding a NUCB1 protein variant having a C-terminal deletion of 1 to about 128 C-terminal amino acids of a NUCB1 protein is provided. Isolated nucleic acids encoding NUCB1 protein variants with C-terminal deletions comprising the polypeptide of SEQ ID NO: 27, SEQ ID NO: 29, or SEQ ID:31 are also provided.

In certain distinct embodiments or in any of the aforementioned embodiments, an isolated nucleic acid encoding a NUCB1 protein variant having: i) a C-terminal deletion of 1 to about 61 C-terminal amino acids of an NUCB1 protein and ii) a N-terminal deletion of about 1 to about 232 N-terminal amino acids of a NUCB1 proteins provided. An isolated nucleic acid encoding NUCB1 protein variants with N- and C-terminal deletions comprising the polypeptide of SEQ ID NO: 33 are also provided.

In certain distinct embodiments or in any of the aforementioned embodiments, an isolated nucleic acid encoding a NUCB1 protein variant having a N-terminal deletion of about 31 to about 232 N-terminal amino acids of a NUCB1 protein are provided. An isolated nucleic acid encoding a NUCB1 protein variant with an N-terminal deletion comprising the polypeptide of SEQ ID NO:25 are also provided.

Any of the aforementioned isolated nucleic acids provided herein can also further comprise a polynucleotide sequence encoding at least one of a signal peptide, a protease cleavage site, and/or purification tag, wherein the signal peptide, the protease cleavage site, and/or the purification tag is operably linked to the polynucleotide sequence encoding a nucleobindin 1 (NUCB1) protein variant.

Any of the aforementioned isolated nucleic acids provided herein can also further comprise a polynucleotide sequence encoding a promoter that is operably linked to the polynucleotide sequence encoding any of the aforementioned nucleobindin 1 (NUCB1) protein variants provided herein. The promoter can be a promoter that is active in a mammalian cell, an insect cell, a yeast cell, or a bacterial cell.

Also provided herein are pharmaceutical or veterinary compositions comprising any of the aforementioned nucleobindin 1 (NUCB1) protein variants and a pharmaceutically or veterinarily acceptable carrier provided herein. In certain embodiments, a pharmaceutical or veterinary composition comprising (i) a nucleobindin 1 (NUCB1) protein variant, wherein the NUCB1 protein variant comprises at least one mutation in each loop region of each EF hand domain of the NUCB1 protein variant, wherein the NUCB1 protein variant does not include a deletion of an entire 12 amino acid loop region of both EF-hand domains and intervening acidic region, and wherein the mutations in the loop regions inhibit calcium binding to the NUCB1 protein variant and ii) a pharmaceutically or veterinarily acceptable carrier is provided. In certain embodiments, a pharmaceutical or veterinary composition comprising (i) a nucleobindin 1 (NUCB1) protein variant, wherein the NUCB1 protein variant comprises at least one mutation in each loop region of each EF hand domain of the NUCB1 protein variant, wherein the NUCB1 protein variant does not include a deletion of either or both entire 12 amino acid loop EF-hand domains and/or intervening acidic region, and wherein the mutations in the loop regions inhibit calcium binding to the NUCB1 protein variant and ii) a pharmaceutically or veterinarily acceptable carrier is provided. In other embodiments, pharmaceutical or veterinary compositions where a NUCB1 protein variant comprising at least one substitution mutation in a loop region of an EF hand domain of the NUCB1 protein variant, at least one deletion of no more than 1 to 6 amino acids in a loop region of an EF hand domain of the NUCB1 protein variant, or a combination of the substitution mutations and the deletion mutations is provided. In other embodiments, pharmaceutical or veterinary compositions where NUCB1 protein variants comprising a first N-terminal proximal EF hand loop region of the SEQ ID NO:7 and a first N-terminal proximal EF hand loop region of SEQ ID NO:8, wherein at least one residue in SEQ ID NO:7 is distinct from a corresponding residue of SEQ ID NO:9, and wherein at least one residue in SEQ ID NO:8 is distinct from a corresponding residue of SEQ ID NO:10 are provided. In such pharmaceutical or veterinary compositions where NUCB1 protein variants comprising a first N-terminal proximal EF hand loop region of the SEQ ID NO:7 and a first N-terminal proximal EF hand loop region of SEQ ID NO:8, $Xaa_1$ of SEQ ID NO:7 and/or SEQ ID NO:8 can be selected independently from lysine or arginine and $Xaa_{12}$ of SEQ ID NO:7 and/or SEQ ID NO:8 can be selected independently from alanine, lysine, or arginine. In other embodiments, the pharmaceutical or veterinary composition comprising a NUCB1 protein variant comprising a first N-terminal proximal EF hand loop region of the SEQ ID NO:7 and a first N-terminal proximal EF hand loop region of SEQ ID NO:8, $Xaa_1$ of both SEQ ID NO:7 and SEQ ID NO:8 is lysine and $Xaa_{12}$ of both SEQ ID NO:7 and SEQ ID NO:8 is alanine. In still other embodiments, the pharmaceutical or veterinary composition comprises an NUCB1 protein variant comprising the first N-terminal proximal EF hand loop region of SEQ ID NO:11 and the second C-terminal proximal EF hand loop region of SEQ ID NO:12. In still other embodiments, the pharmaceutical or veterinary composition can comprise a NUCB1 protein variant that comprises SEQ ID NO:6.

In any of the aforementioned pharmaceutical or veterinary compositions provided herein, the pharmaceutically or veterinarily acceptable carrier can comprise at least one polymer. In such embodiments where the pharmaceutical or veterinary composition comprises a polymer, the polymer can be selected from the group consisting of alginates, chitosan, collagen, fibrins, methoxy poly(ethylene glycol), polyanhydrides, poly(e-caprolactone), poly(ethylene oxide), poly(lactic acid), poly-lactide-co-glycolide (PLGA), poly(ortho esters), polyethylene vinyl-co-acetate (EVAc), polyethylene glycol (PEG), polyester-PEG triblock copolymers, polyphosphazenes, poly[(sebacic-co-(ricinoleic acid)], ricinoleic acid, silicone, and combinations thereof.

Also provided herein are methods of producing any of the aforementioned NUCB1 protein variants provided herein. In certain embodiments, methods of producing a nucleobindin 1 (NUCB1) protein variant comprising the steps of: a) culturing a cell comprising an expression vector that comprises a promoter that is operably linked to a polynucleotide encoding a NUCB1 protein variant, wherein the NUCB1 protein variant comprises at least one mutation in each loop region of each EF hand domain of the NUCB1 protein variant, wherein the NUCB1 protein variant does not include a deletion of an entire 12 amino acid loop region of both EF-hand domains and intervening acidic region, and wherein the mutations in the loop regions inhibit calcium binding to the NUCB1 protein variant; and b) recovering the NUCB1 protein variant from the cell or from a culture medium from step (a) are provided for producing a nucleobindin 1 (NUCB1) protein variant. In certain embodiments, methods of producing a nucleobindin 1 (NUCB1) protein variant comprising the steps of: a) culturing a cell comprising an expression vector that comprises a promoter that is operably linked to a polynucleotide encoding a NUCB1 protein variant, wherein the NUCB1 protein variant comprises at least one mutation in each loop region of each EF hand domain of the NUCB1 protein variant, wherein the NUCB1 protein variant does not include a deletion of either or both entire 12 amino acid loop EF-hand domains and/or intervening acidic region, and wherein the mutations in the loop regions inhibit calcium binding to the NUCB1 protein variant; and b) recovering the NUCB1 protein variant from the cell or from a culture medium from step (a) are provided for producing a nucleobindin 1 (NUCB1) protein variant. In other embodiments, methods for producing a NUCB1 protein variant that comprises at least one substitution mutation in a loop region of an EF hand domain of the NUCB1 protein variant, at least one deletion of no more than 1 to 6 amino acids in a loop region of an EF hand domain of the NUCB1 protein variant, or a combination of the substitution mutations and the deletion mutations are provided. In other embodiments, methods where the NUCB1 protein variant comprises a first N-terminal proximal EF hand loop region of the SEQ ID NO:7 and a first N-terminal proximal EF hand loop region of SEQ ID NO:8, wherein at least one residue in SEQ ID NO:7 is distinct from a corresponding residue of SEQ ID NO:9, and wherein at least one residue in SEQ ID NO:8 is distinct from a corresponding residue of SEQ ID NO:10 are provided. In certain embodiments of such methods, the NUCB1 protein variant comprises a protein where $Xaa_1$ of SEQ ID NO:7 and/or SEQ ID NO:8 is selected independently from lysine or arginine and wherein $Xaa_{12}$ of SEQ ID NO:7 and/or SEQ ID NO:8 is selected independently from alanine, lysine, or arginine. In still other embodiments of such methods, the NUCB1 protein variant comprises a protein where $Xaa_1$ of both SEQ ID NO:7 and SEQ ID NO:8 is lysine and where $Xaa_{12}$ of both SEQ ID NO:7 and SEQ ID NO:8 is alanine. In still other embodiments, a method of producing a NUCB1 protein variant where the first N-terminal proximal EF hand loop region is SEQ ID NO:11 and where the second C-terminal proximal EF hand loop region is SEQ ID NO:12 is provided. In alternative embodiments, methods of producing a NUCB1 protein variant comprising SEQ ID NO:6 are provided.

In any of the aforementioned methods of producing a NUCB1 protein variant, the cell can be a mammalian cell, a bacterial cell, an insect cell, or a yeast cell. Mammalian cells used in the methods of production can be human cells, monkey cells, mouse cells, or a hamster cells. A mammalian cell used in the methods of production can also be a Hela, CHO, Jurkat, HepG2, H1299, HEK293 cells or NIH 3T3 cell. A yeast cell used in the methods of production can be a *Pichia* cell, a *Saccharomyces* cell, a *Kluyveromyces* cell, a *Candida* cell, a *Torulopsis* cell, a *Hansenula* cell, or a *Yarrowia* cell. A bacterial cell used in the methods of production can be an *Escherichia* cell, a *Bacillus* cell, a *Salmonella* cell, a *Lactobacillus* cell, a *Lactococcus* cell, a *Streptomyces* cell, a Streptococcal cell, or a *Corynebacterium* cell.

Cells comprising any of the aforementioned nucleic acids that encode any of the aforementioned NUCB1 protein variants are also provided herein. In certain embodiments, a cell comprising a polynucleotide encoding promoter that is operably linked to a polynucleotide encoding a NUCB1 protein variant wherein the NUCB1 protein variant comprises at least one mutation in each loop region of each EF hand domain of the NUCB1 protein variant, wherein the NUCB1 protein variant does not include a deletion of an entire 12 amino acid loop region of both EF-hand domains and intervening acidic region, and wherein the mutations in the loop regions inhibit calcium binding to the NUCB1 protein variant is provided. In certain embodiments, a cell comprising a polynucleotide encoding promoter that is operably linked to a polynucleotide encoding a NUCB1 protein variant wherein the NUCB1 protein variant comprises at least one mutation in each loop region of each EF hand domain of the NUCB1 protein variant, wherein the NUCB1 protein variant does not include a deletion of either or both entire 12 amino acid loop EF-hand domains and/or intervening acidic region, and wherein the mutations in the loop regions inhibit calcium binding to the NUCB1 protein variant is provided. In other embodiments, a cell comprising a nucleic acid that encodes a NUCB1 protein variant comprising at least one substitution mutation in a loop region of an EF hand domain of the NUCB1 protein variant, at least one deletion of no more than 1 to 6 amino acids in a loop region of an EF hand domain of the NUCB1 protein variant, or a combination of the substitution mutations and the deletion mutations is provided. In other embodiments, a cell comprising a nucleic acid that encodes a NUCB1 protein variant that comprises a first N-terminal proximal EF hand loop region of the SEQ ID NO:7 and a first N-terminal proximal EF hand loop region of SEQ ID NO:8, wherein at least one residue in SEQ ID NO:7 is distinct from a corresponding residue of SEQ ID NO:9, and wherein at least one residue in SEQ ID NO:8 is distinct from a corresponding residue of SEQ ID NO:10 is provided. In still other embodiments, a cell comprising a nucleic acid that encodes a NUCB1 protein variant where $Xaa_1$ of SEQ ID NO:7 and/or SEQ ID NO:8 is selected independently from lysine or arginine and wherein $Xaa_{12}$ of SEQ ID NO:7 and/or SEQ ID NO:8 is selected independently from alanine, lysine, or arginine is provided. In still other embodiments, a cell comprising a nucleic acid that encodes a NUCB1 protein variant where $Xaa_1$ of both SEQ ID NO:7 and SEQ ID NO:8 is lysine and where $Xaa_{12}$ of both SEQ ID NO:7 and SEQ ID NO:8 is alanine is provided. In other embodiments, a cell comprising a nucleic acid that encodes a NUCB1 protein variant where the first N-terminal proximal EF hand loop region is SEQ ID NO:11 and wherein the second C-terminal proximal EF hand loop region is SEQ ID NO:12 is provided. In other embodiments, a cell comprising a nucleic acid that encodes a NUCB1 protein variant comprising SEQ ID NO:6 is provided.

Aforementioned cells comprising any of the aforementioned nucleic acids encoding any of the aforementioned NUCB1 protein variants can be a mammalian cell, a bacterial cell, an insect cell or a yeast cell. Such mammalian cells can be a human cell, a monkey cell, a mouse cell, or a hamster cell. Such mammalian cells can also be a Hela, CHO, Jurkat, HepG2, H1299, HEK293 cells or a NIH 3T3 cell. In other embodiments, such yeast cells can be a *Pichia* cell, a *Saccharomyces* cell, a *Kluyveromyces* cell, a *Candida* cell, a *Torulopsis* cell, a *Hansenula* cell, or a *Yarrowia* cell. In still other embodiments, such bacterial cells can be an *Escherichia* cell, a *Bacillus* cell, a *Salmonella* cell, a *Lactobacillus* cell, a *Lactococcus* cell, a *Streptomyces* cell, a Streptococcal cell, or a *Corynebacterium* cell.

Kits comprising any of the aforementioned pharmaceutical or veterinary compositions comprising any of the aforementioned NUCB1 protein variants are also provided herein. In certain embodiments, a kit comprising:

a) a pharmaceutical or veterinary composition comprising (i) a therapeutically effective amount of a nucleobindin 1 (NUCB1) protein variant, wherein the NUCB1 protein variant comprises at least one mutation in each loop region of each EF hand domain of the NUCB1 protein variant, wherein the NUCB1 protein variant does not include a deletion of an entire 12 amino acid loop region of both EF-hand domains and intervening acidic region, and wherein the mutations in the loop regions inhibit calcium binding to the NUCB1 protein variant; and (ii) a pharmaceutically acceptable carrier; and, b) one or more containers for the pharmaceutical or veterinary composition(s) is provided. In certain embodiments, a kit comprising: a) a pharmaceutical or veterinary composition comprising (i) a therapeutically effective amount of a nucleobindin 1 (NUCB1) protein variant, wherein the NUCB1 protein variant comprises at least one mutation in each loop region of each EF hand domain of the NUCB1 protein variant, wherein the NUCB1 protein variant does not include a deletion of either or both entire 12 amino acid loop EF-hand domains and/or intervening acidic region, and wherein the mutations in the loop regions inhibit calcium binding to the NUCB1 protein variant; and (ii) a pharmaceutically acceptable carrier; and, b) one or more containers for the pharmaceutical or veterinary composition(s) is provided. In other embodiments, the kit can further comprises a device that provides for administration of the pharmaceutical or veterinary composition to a subject in need thereof. In still other embodiments, the kit can further comprises instructions for use. In certain embodiments of such kits provided herein, the composition is a pharmaceutical composition and the subject is a human. In other embodiments of such kits provided herein, the composition is a veterinary composition and the subject is an animal other than a human. When the composition is a veterinary composition, the animal can be a non-human primate, horse, cow, pig, dog, or cat.

Methods of treating subjects suffering from amyloidosis with therapeutically effective amounts of any of the aforementioned pharmaceutical or veterinary compositions comprising any of the aforementioned NUCB1 protein variants is also provided herein. In certain embodiments, methods of treating a subject suffering from amyloidosis that comprise the step of administering a therapeutically effective amount of a pharmaceutical or veterinary composition comprising a nucleobindin 1 (NUCB1) protein variant, wherein the NUCB1 protein variant comprises at least one mutation in each loop region of each EF hand domain of the NUCB1 protein variant, wherein the NUCB1 protein variant does not include a deletion of an entire 12 amino acid loop region of both EF-hand domains and intervening acidic region, and wherein the mutations in the loop regions inhibit calcium binding to the NUCB1 protein variant, are provided. In certain embodiments, methods of treating a subject suffering from amyloidosis that comprise the step of administering a therapeutically effective amount of a pharmaceutical or veterinary composition comprising a nucleobindin 1 (NUCB1) protein variant, wherein the NUCB1 protein variant comprises at least one mutation in each loop region of each EF hand domain of the NUCB1 protein variant, wherein the NUCB1 protein variant does not include a deletion of either or both entire 12 amino acid loop EF-hand domains and/or intervening acidic region, and wherein the mutations in the loop regions inhibit calcium binding to the NUCB1 protein variant, are provided. In certain embodiments, the subject is a human suffering from amyloidosis of the brain. In such subjects, amyloidosis of the brain can comprise an accumulation of amyloid beta fibrils. In still other embodiments, the subject is a human suffering from amyloidosis of the pancreas. In such human subjects, the amyloidosis of the pancreas can comprise an accumulation of amylin fibrils. In certain embodiments where the subject is a human, the human can be suffering from an amyloid associated disease selected form the group consisting of Alzheimer's, Parkinson's, Huntington's, Prion diseases, Type 2 Diabetes Mellitus, Dialysis-related amyloidosis, Amyotrophic lateral sclerosis, Pick's Disease, Senile systemic amyloidosis, Machado-Joseph Disease, Gelsolin Amyloid Disease, Primary systemic amyloidosis, Secondary systemic amyloidosis, Familial non-neuropathic amyloidosis, Familial subepithelial corneal amyloid, Hereditary renal amyloidosis, Pituitary-gland amyloidosis, Injection-localized amyloidosis, Atrial amyloidosis, Familial British dementia, Hereditary cerebral amyloid angiopathy, Familial amyloid polyneuropathy III, and Chronic obstructive pulmonary disease.

In other embodiments where the composition is a veterinary composition, the subject can be an animal that is not a human. Such animals can be a non-human primate, horse, cow, pig, dog, or cat. In certain embodiments, the animal is suffering from renal or hepatic amyloidosis.

In certain embodiments of the aforementioned methods of use, a therapeutically effective amount of a pharmaceutical composition is administered by parenteral injection, by injection into an organ, intrathecal injection, implantation of a pump, stereotactic delivery, implantation of a cannula, implantation of a three-dimensional implant, or implantation of microspheres.

Methods of treating subjects suffering from amyloidosis with NUCB1 variant proteins comprising at least one mutation in a single loop region of an EF hand domain of the NUCB1 variant protein are also provided. In certain embodiments, a method of treating a subject suffering from amyloidosis, comprising the step of administering a therapeutically effective amount of a pharmaceutical composition comprising a nucleobindin 1 (NUCB1) variant protein, wherein the NUCB1 variant protein comprises at least one mutation in a single loop region of an EF hand domain of the NUCB1 mutant protein that inhibits calcium binding to the NUCB1 mutant protein and wherein the NUCB1 mutant protein has amyloid fibril disaggregating activity and/or inhibits amyloid fibril formation, thereby treating a subject suffering from amyloidosis is provided.

Also provided herein are pharmaceutical or veterinary compositions comprising any of the aforementioned nucleic acids that encode any of the aforementioned NUCB1 protein variants. In certain embodiments, a pharmaceutical or veterinary composition comprising (i) a nucleic acid that encodes a nucleobindin 1 (NUCB1) protein variant, wherein the NUCB1 protein variant comprises at least one mutation in each loop region of each EF hand domain of the NUCB1 protein variant, wherein the NUCB1 protein variant does not include a deletion of an entire 12 amino acid loop region of both EF-hand domains and intervening acidic region, and wherein the mutations in the loop regions inhibit calcium binding to the NUCB1 protein variant; and a pharmaceutically or veterinarily acceptable carrier is provided. In certain embodiments, a pharmaceutical or veterinary composition comprising (i) a nucleic acid that encodes a nucleobindin 1 (NUCB1) protein variant, wherein the NUCB1 protein variant comprises at least one mutation in each loop region of each EF hand domain of the NUCB1 protein variant, wherein the NUCB1 protein variant does not include a deletion of either or both entire 12 amino acid loop EF-hand domains and/or intervening acidic region, and wherein the mutations in the loop regions inhibit calcium binding to the NUCB1 protein variant; and a pharmaceutically or veterinarily acceptable carrier is provided. Methods of making such pharmaceutical or veterinary compositions are provided. Methods of using therapeutically effective amounts of such pharmaceutical or veterinary compositions to treat a subject suffering from amyloidosis are also provided.

Methods for disaggregating amyloid fibrils comprising the step of contacting said fibrils with an exogenously provided NUCB1 protein or NUCB1 protein variant are also provided. In certain embodiments of these methods, the NUCB1 protein or NUCB1 protein variant is provided to a cell comprising amyloid fibrils or to an cell-free composition comprising amyloid fibrils. In certain embodiments of these methods, the fibrils are selected from the group consisting of amylin fibrils and Aβ fibrils.

Methods for inhibiting amyloid fibril formation, comprising the step of contacting a peptide capable of forming amyloid fibrils with an exogenously provided NUCB1 protein or NUCB1 protein variant are also provided. In certain embodiments of these methods, the NUCB1 protein or NUCB1 protein variant is provided to a cell comprising a peptide capable of forming amyloid fibrils or to an cell-free composition comprising a peptide capable of forming amyloid fibrils. In certain embodiments of these methods, the peptide is selected from the group consisting of amyloid β, amyloid tau, and amylin,

BRIEF DESCRIPTION OF THE DRAWINGS

The accompanying drawings, which are incorporated in and form a part of the specification, illustrate the embodiments of the present invention and together with the description, serve to explain the principles of the invention.

In the drawings:

FIG. 7. Sequence alignment of the 2 EF hand loop regions of NUCB1 with 4 EF hand loop regions in Calmodulin. Residues at positions 1 and 12 in the loop region are highly conserved acidic residues. Aspartic acid 253 and 305 along with glutamic acid 264 and 316 were mutated to lysine and alanine respectively in sNUCBI(tetramutant). NUCB1, EF1/1-12 is residue 253 to 264 of SEQ ID NO:2, NUCB1EF1/1-12 is residue 305 to 316 of SEQ ID NO:2, CaMEF4/1-12 is SEQ ID NO: 13, CaMEF2/1-12 is SEQ ID NO: 14, CaMEF3/1-12 is SEQ ID NO: 15, and CaMEF1/1-12 is SEQ ID NO: 16.

sNUCBI(tetramutant) is NUCB1 Δ1-31; D253K, E264A, D305K, E316A (SEQ ID NO:6).

Figure 17:
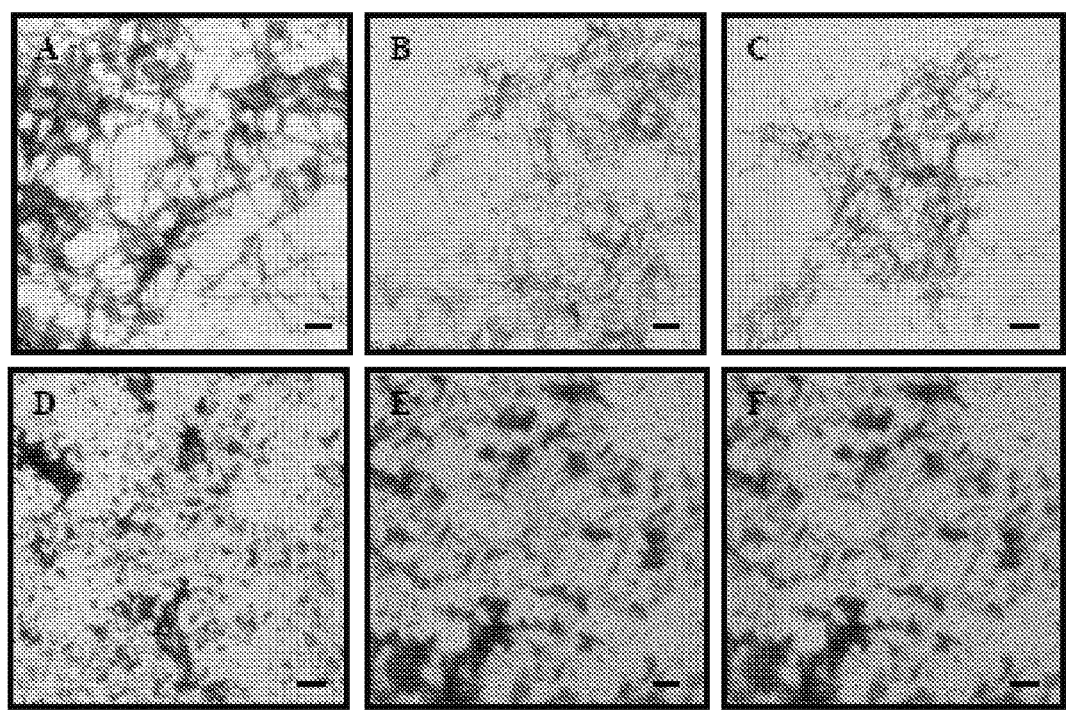

FIG. 17. Disaggregation of wt Aβ42 fibrils by the sNUCBI (tetramutant) in the absence of calcium in 100 mM Tris at pH 7.5. Aβ42 fibrils [A-C] were incubated with sNUCBI(tetramutant) and samples were withdrawn for TEM analysis after 30 mins [D-F]. Scale bar in the images represents 200 nm. sNUCBI(tetramutant) is NUCB1 Δ1-31; D253K, E264A, D305K, E316A (SEQ ID NO:6).

Figure 18:
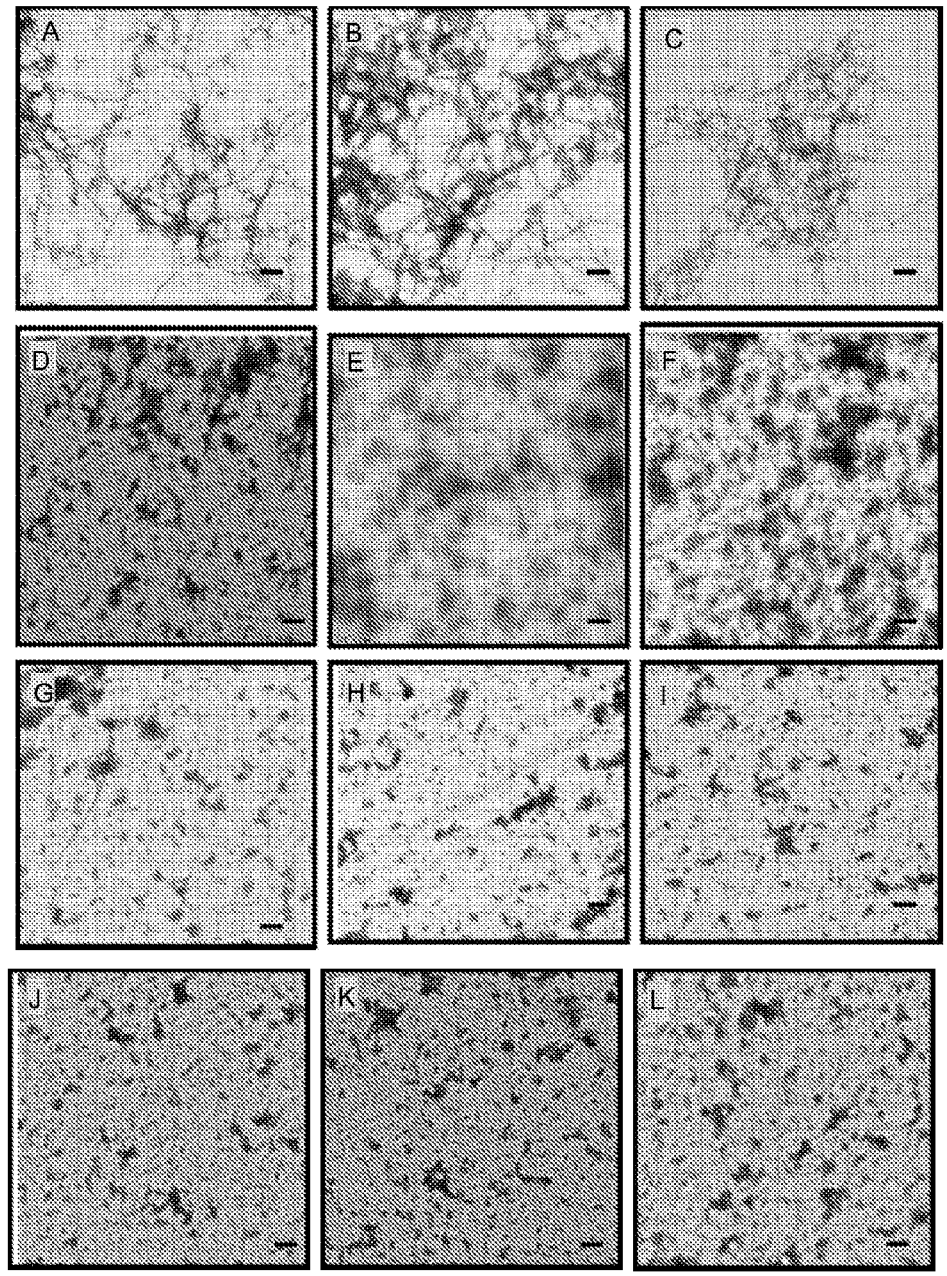

FIG. 18. Disaggregation of Aβ42 fibrils by sNUCBI(tetramutant) pre-incubated with calcium in 100 mM Tris at pH 7.5. Aβ42 fibrils [A-C] are incubated with sNUCBI(tetramutant) and 1 mM Ca2+ and disaggregation is monitored at 5 mins [D-F]. 15 mins [G-I] and 30 mins [J-L]. Scale bar in the images represents 200 nm. sNUCBI(tetramutant) is NUCB1 Δ1-31; D253K, E264A, D305K, E316A (SEQ ID NO:6).

Figure 19:
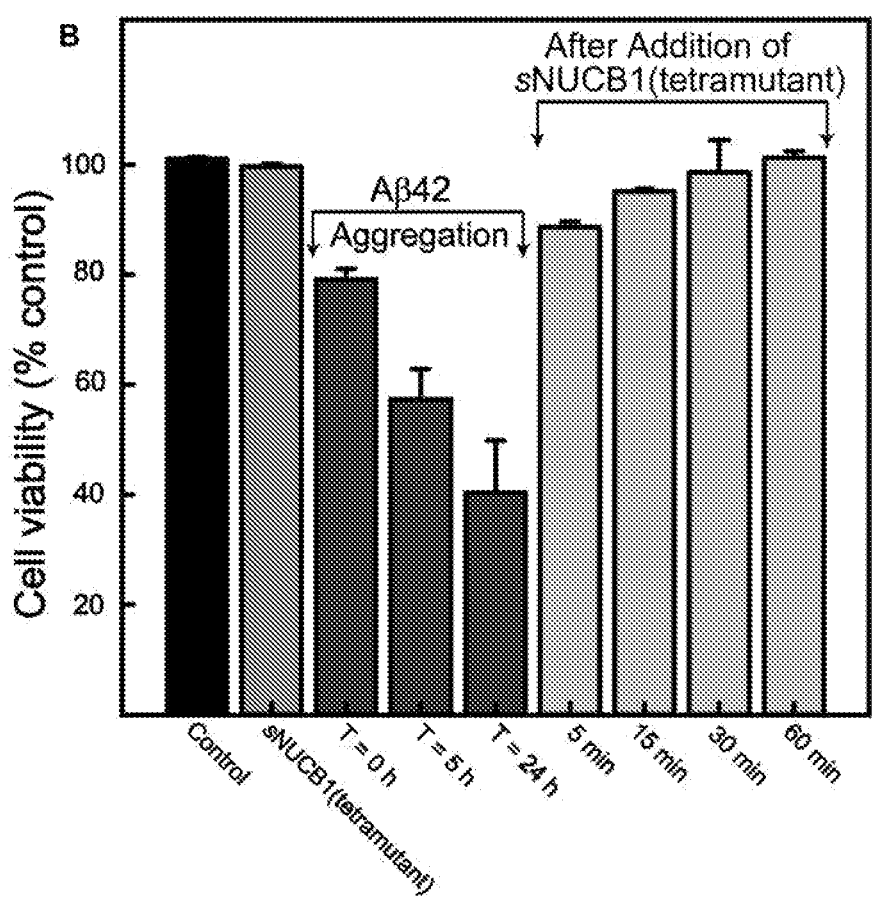

FIG. 19. MTT assay results on PC12 cells showing the cell viability in the presence of Aβ42 monomers, oligomers and fibrils. The cell viability was increased on disaggregation of these fibrils when incubated with Ca2+ free sNUCBI(tetramutant). Monomer samples are Aβ peptide taken from initial aggregation reaction in 10 mM Tris at pH 7.5 and 25 degrees C. Oligomer samples were withdrawn at 5 hours and fibrils were withdrawn after 24 hours. All samples were incubated with cells for 4 hours before addition of MTT. sNUCBI(tetramutant) is NUCB1 Δ1-31; D253K, E264A, D305K, E316A (SEQ ID NO:6).

Figure 20:
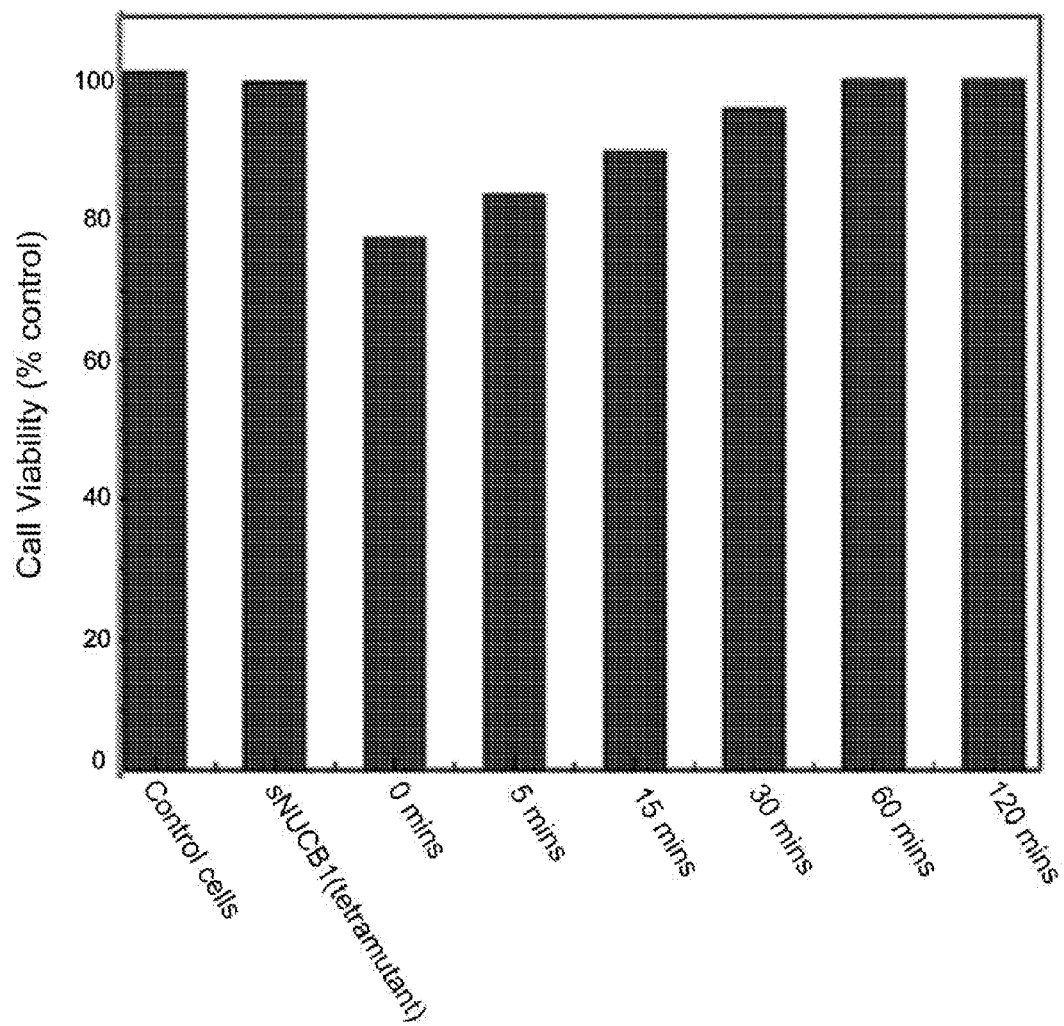

FIG. 20. MTT assay results on PC12 cells showing the cell viability in the presence of Aβ42 monomers. The cell viability was increased on inhibition of aggregation of Aβ42 monomers when incubated with Ca2+ free sNUCBI(tetramutant) as compared to the control cells. Monomer samples are Aβ peptide taken from initial aggregation reaction in 10 mM Tris at pH 7.5 and 25 degrees C. All samples were incubated with cells for 4 hours before addition of MTT. sNUCBI(tetramutant) is NUCB1 Δ1-31; D253K, E264A, D305K, E316A (SEQ ID NO:6).

Figure 21:
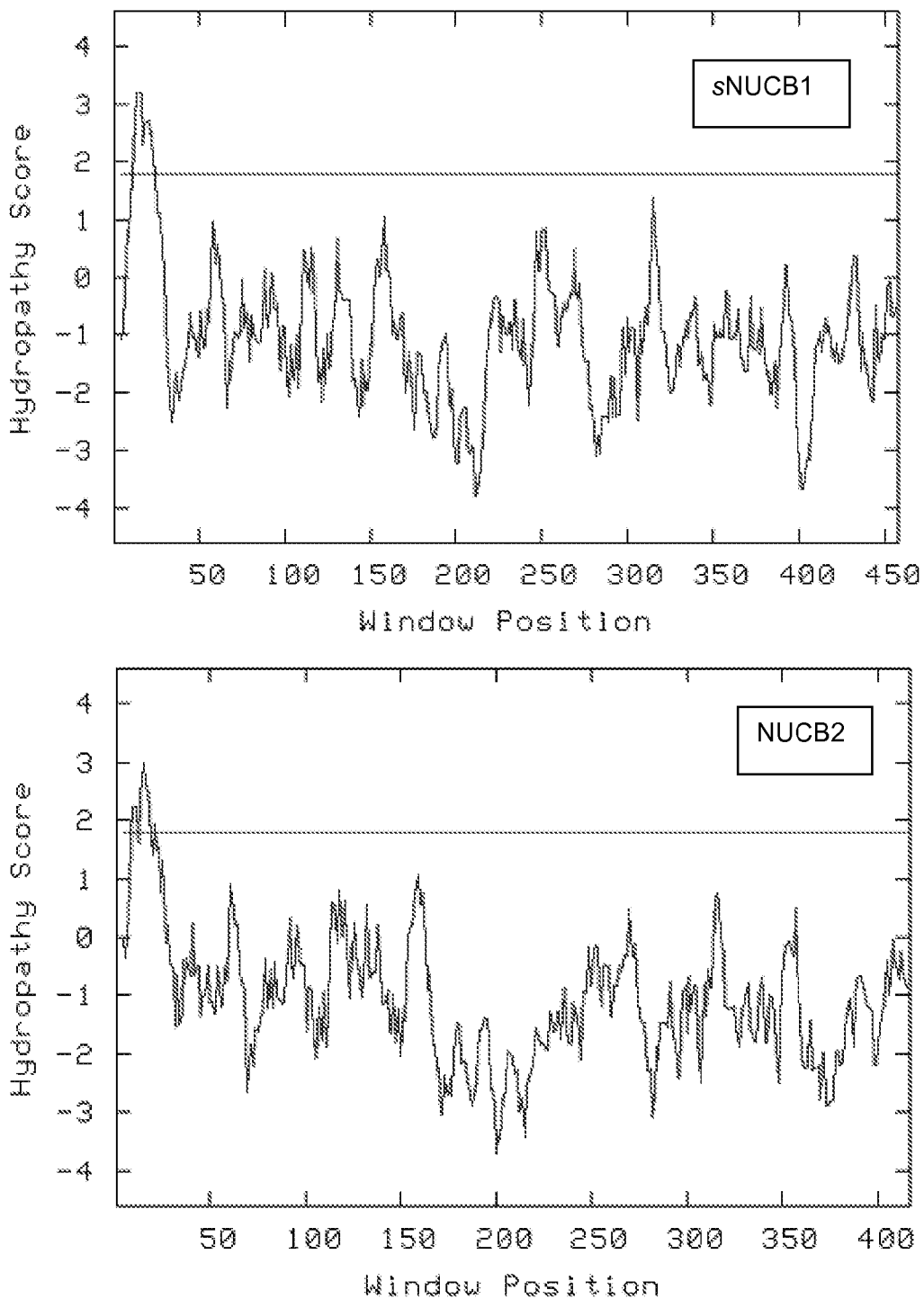

FIG. 21. Hydropathy plots of the NUCB1 protein (top panel) and the NUCB2 protein (bottom panel). Hydrophobic amino acids in the region above the red line were deleted from both NUCB1 and NUCB2 as described.

Figure 22:
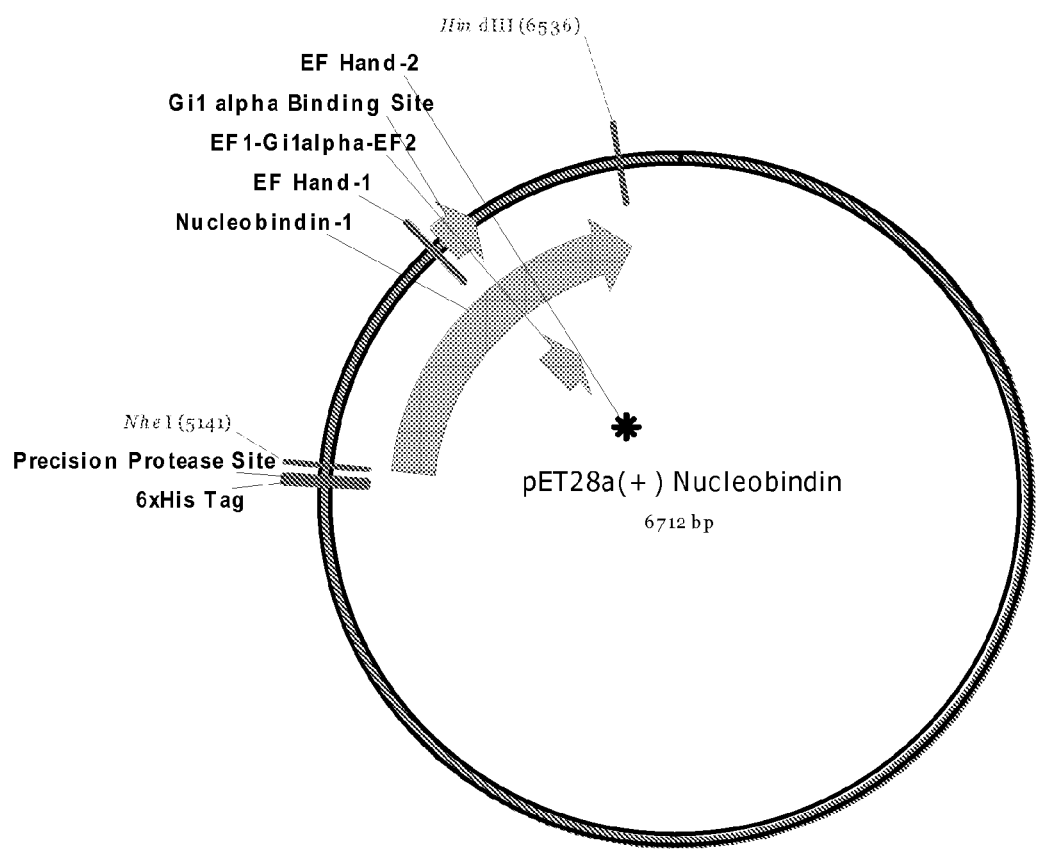

FIG. 22. Map of the modified pET28a(+) vector used for expression of NUCB1.

Figure 23:
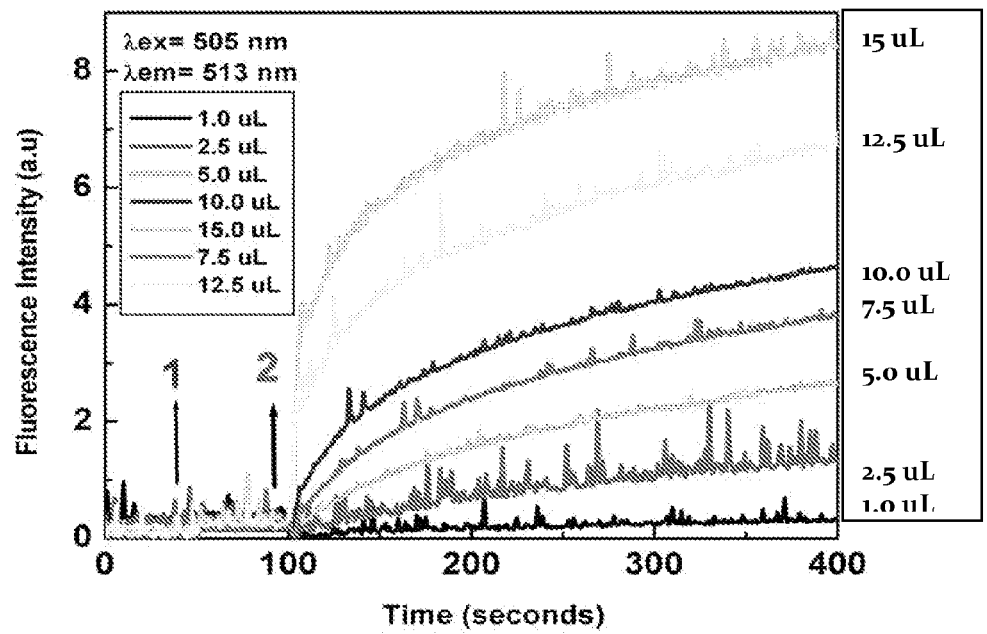

FIG. 23. A peptidase activity assay of the NUCB1 tetramutant. The NUCB1 tetramutant is NUCB1 Δ1-31; D253K, E264A, D305K, E316A (SEQ ID NO:6). Injection of the varying concentrations of protein is indicated by the arrow "1" (at 50 sec's) and the injection of Zn2+ to a final concentration of 83 micromolar is indicated as arrow "2" (at 100 sec's).

Figure 24:
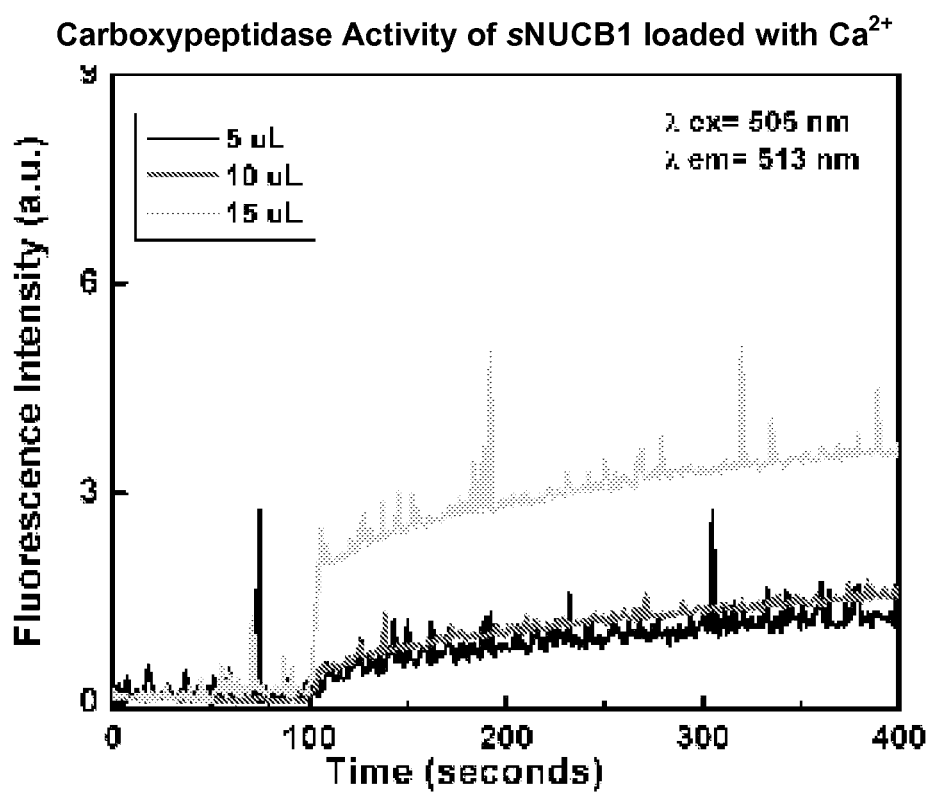

FIG. 24. A peptidase activity assay of NUCB1 loaded with Calcium. "1" in the figure is time of NUCB1 injection and "2" is time of zinc injection. NUCB1 is SEQ ID NO:3 (NUCB1 with a deletion of residues 1-31). Injection of the varying concentrations of protein is indicated by the arrow "1" (at 50 sec's) and the injection of Zn2+ to a final concentration of 83 micromolar is indicated as arrow "2" (at 100 sec's).

Figure 25:
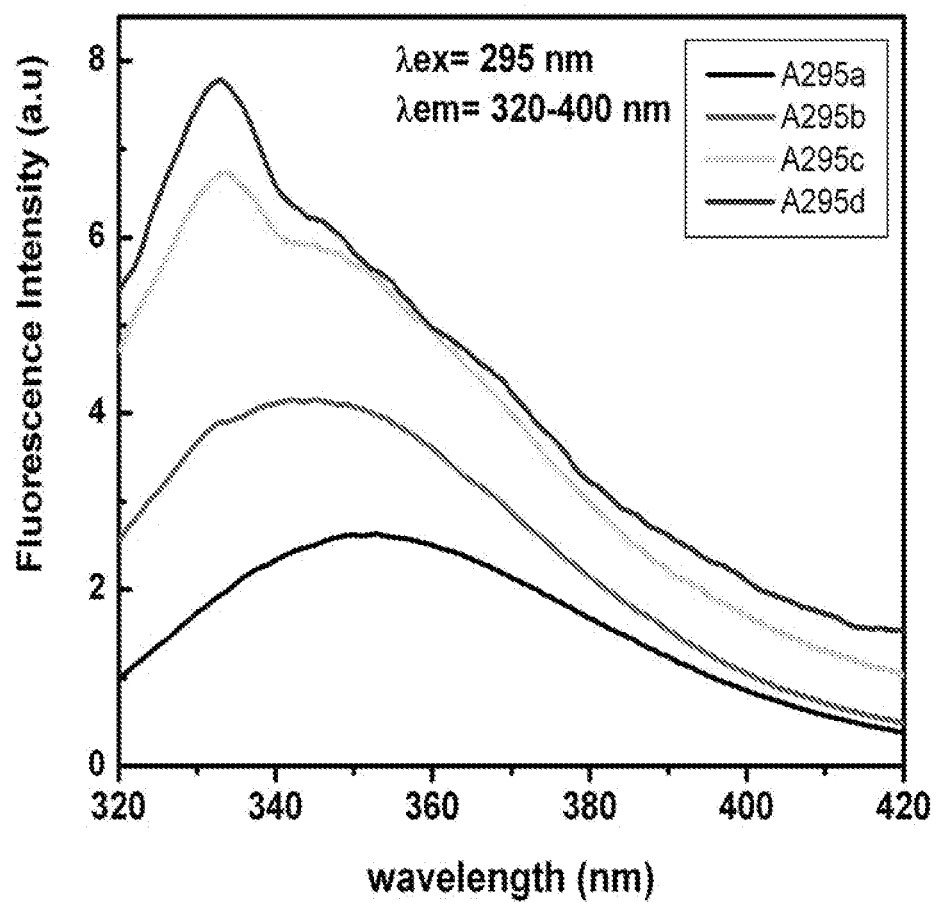

FIG. 25. Changes in the W233 and W333 fluorescence of NUCB-1 (Tetramutant). The zinc concentration varied between 166 micromolar to 2.6 millimolar. The NUCB1 tetramutant is NUCB1 Δ1-31; D253K, E264A, D305K, E316A (SEQ ID NO:6).

FIG. 26. Conformational Changes in the aromatic residues of NUCB-1 (tetra) on Binding to Zinc. The NUCB1 tetramutant is NUCB1 Δ1-31; D253K, E264A, D305K, E316A (SEQ ID NO:6). Panel (A) at top shows spectral changes of Bis-ANS monitored as a function of different zinc concentrations. Panel (b) at bottom shows overall changes monitored for Bis-ANS for the protein, NUCB-1 (Tetramutant) as a function of zinc binding.

Figure 27:
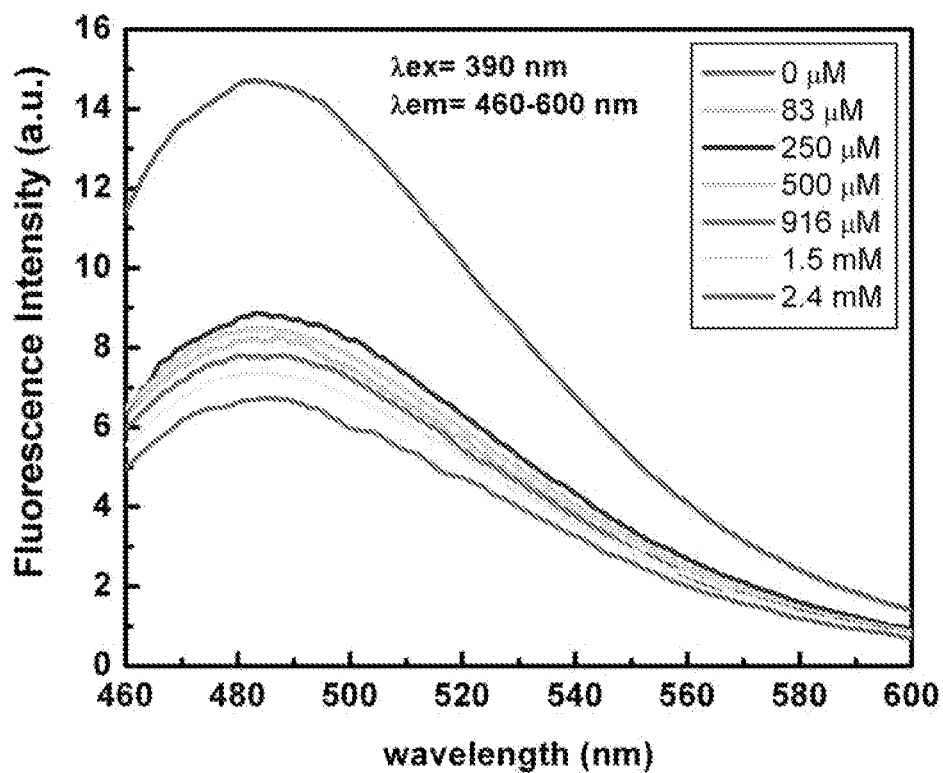

FIG. 27. NUCB1 (Tetra) has Intrinsic Zinc Bound to the Protein. The NUCB1 tetramutant is NUCB1 Δ1-31; D253K, E264A, D305K, E316A (SEQ ID NO:6).

Figure 28:
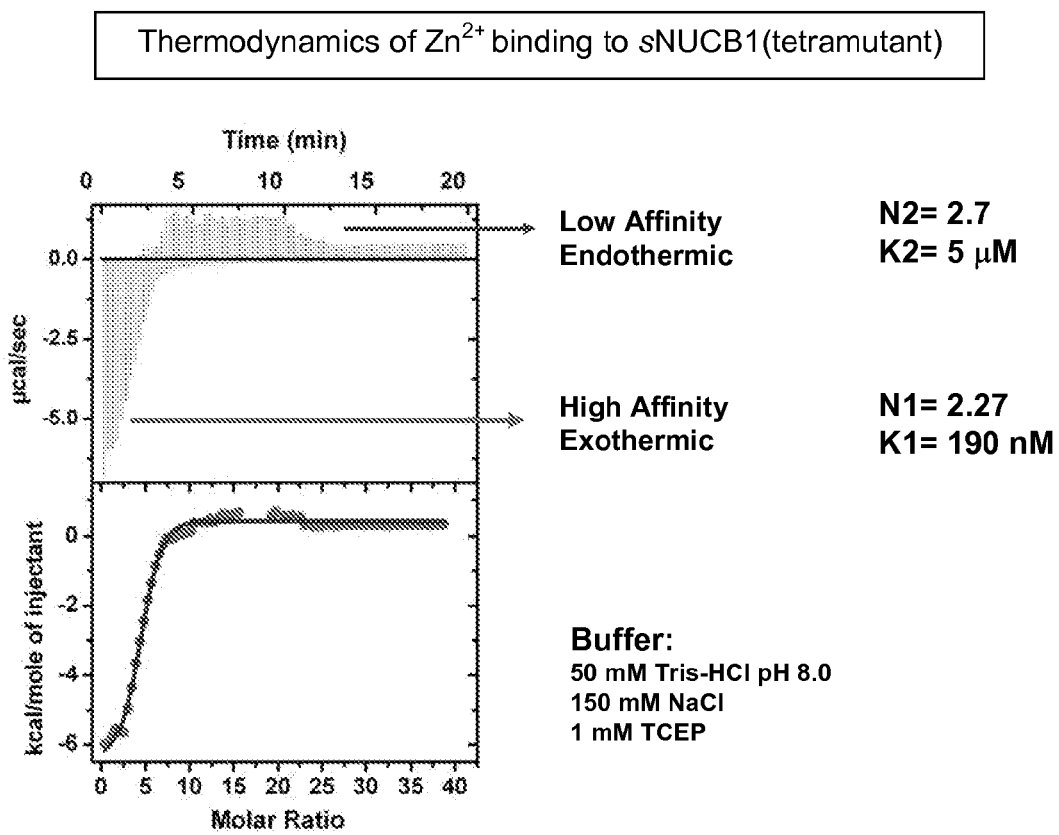

FIG. 28. Thermodynamics of $Zn^{2+}$ Binding to NUCB-1 (Tetramutant). The NUCB1 tetramutant is NUCB1 Δ1-31; D253K, E264A, D305K, E316A (SEQ ID NO:6).

Figure 29:
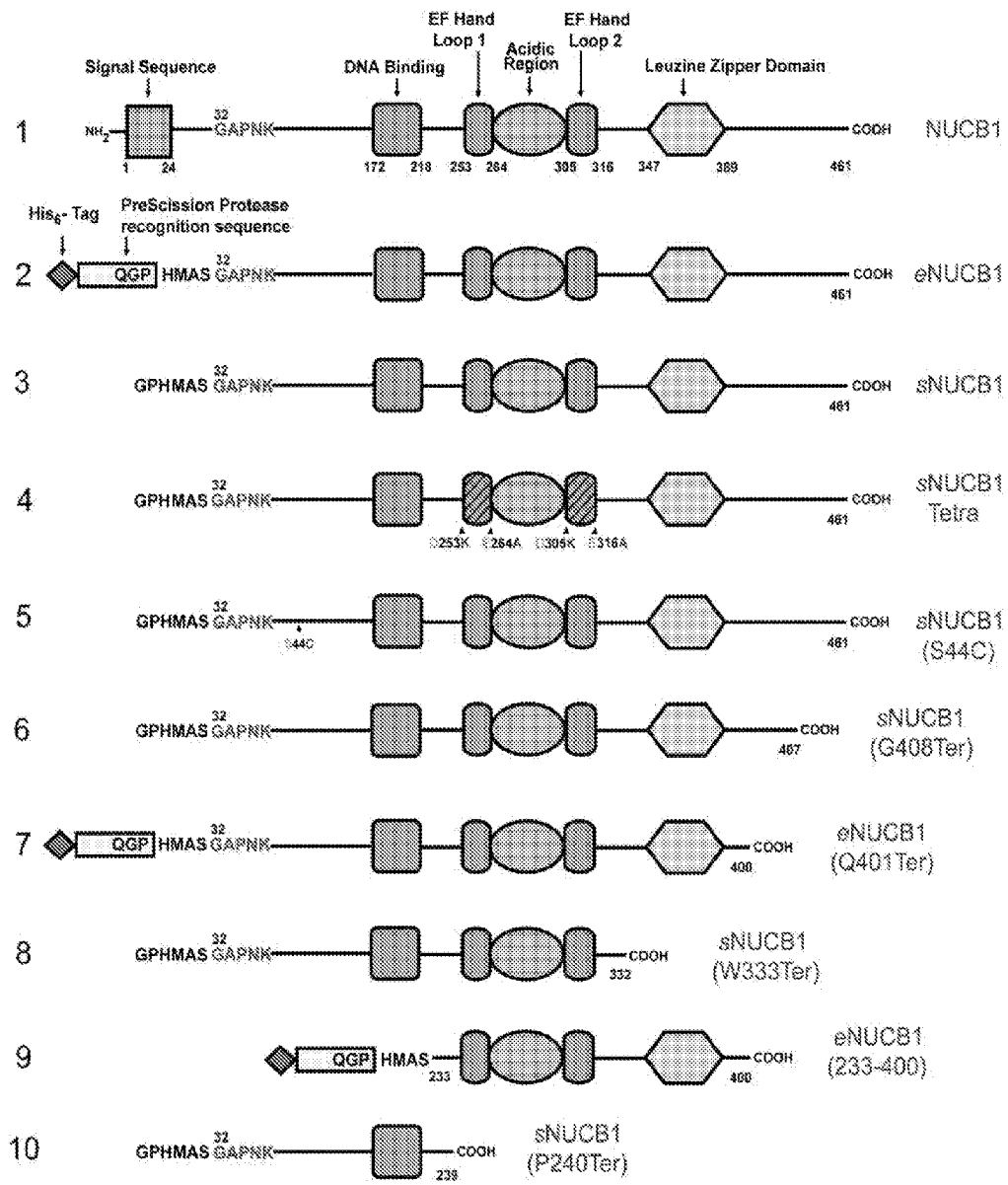

FIG. 29. Diagram of NUCB1 wild-type and NUCB1 variant proteins. In the figure, NUCB1 is SEQ ID NO:2, sNUCB1 (Pro) is provided as SEQ ID NO: 39 and comprises the Hisx6 tag, the PreScission Protease Recognition Sequence™ (SEQ ID NO: 36), and NUCB1 sequences as shown, sNUCB1 comprises SEQ ID NO:3, sNUCB1 Tetra comprises SEQ ID NO:6, sNUCB1(S44C) comprises the N-terminal sequence GPHMAS (SEQ ID NO:37) and SEQ ID NO:25 as shown, sNUCB1(G408Ter) comprises the N-terminal sequence GPHMAS (SEQ ID NO:37) and SEQ ID NO:27 as shown, eNUCB1(Q401 Ter) comprises the Hisx6 tag, two serine residues, a glycine residue, PreScission Protease Recognition Sequence™ followed by a histidine, a methionine, an alanine, and a serine (SEQ ID NO: 38) and SEQ ID NO:29 as shown, sNUCB1 (W333Ter) comprises the N-terminal sequence GPHMAS (SEQ ID NO:37) and SEQ ID NO:31 as shown, eNUCB1(233-400) comprises the Hisx6 tag, two serine residues, a glycine residue, PreScission Protease Recognition Sequence™ followed by a histidine, a methionine, an alanine, and a serine (SEQ ID NO: 38) and SEQ ID NO:33 as shown, and sNUCB1 (P240Ter) comprises the N-terminal sequence GPHMAS (SEQ ID NO:37) and SEQ ID NO:35 as shown.

DETAILED DESCRIPTION OF THE INVENTION

In view of the foregoing, it will be seen that the several advantages of the invention are achieved and attained.

Definitions

As used herein, the phrase "NUCB1 protein variant" refers to any non-naturally occurring form of an NUCB1 protein that displays amyloid fibril disaggregation activity and/or amyloid fibril formation inhibitory activity.

As used herein, the term "sNUCBI(tetramutant)" is used to describe one NUCB1 protein variant comprising: a deletion of amino acid residues 1-31, a substitution of aspartate 253 for lysine, a substitution of glutamate 264 for alanine, a substitution of aspartate 305 for lysine, and a substitution of glutamate 316 for alanine as shown in SEQ ID NO:6. In U.S. Provisional Patent Application No. 61/081,589, the term "Calnull" is used to identify the sNUCBI(tetramutant) protein variant.

As used herein, the phrase "conservative amino acid substitutions" refers to one or more changes in an amino acid sequence where one or more amino acid(s) are replaced with another amino acid(s), the size, charge, and/or polarity of which is similar to that of the native amino acid. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; (4) neutral non-polar (hydrophobic) amino acids such as alanine, leucine, isoleucine, valine, proline, phenylalanine, tryptophan, and methionine. Conservative amino acid changes can in certain instances be made by substituting one amino acid within one of these groups with another amino acid within the same group.

As used herein, the term "Calnuc" is used interchangeably with the term "NUCB1" to refer to both the naturally occurring forms of proteins encoded by the NUCB1 gene of a given organism or derivatives of that naturally occurring NUCB1 protein where the naturally occurring forms of both EF hand loop domains are present. For "Calnuc" or "NUCB1" proteins from humans, these terms thus refer to the naturally occurring forms of the proteins encoded by the NUCB1 gene located on human chromosome 19 or derivatives of that naturally occurring human NUCB1 protein where the naturally occurring forms of both EF hand loop domains are present. Derivatives of that naturally occurring human NUCB1 protein where the naturally occurring forms of both EF hand loop domains are present include, but are not limited to, an NUCB1 protein comprising a deletion of residues 1-31 as shown in SEQ ID NO:3.

As used herein, the term "corresponding", when used in the context of comparing, aligning, or identifying equivalent amino acids in one polypeptide sequence with another polypeptide sequence, refers to the comparison or alignment that will yield the highest percent identity when aligned with the other polypeptide sequence.

As used herein, the phrase "inhibits calcium binding" refers to any mutation in an NUCB1 protein that results in a decrease in calcium binding ability relative to that of a control NUCB1 protein that does not comprise the mutation.

As used herein, the phrase "non-conservative amino acid substitutions" refers to one or more changes in an amino acid sequence where one or more amino acid(s) are replaced with another amino acid(s), the size, charge, and/or polarity of which is dissimilar to that of the native amino acid. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; (4) neutral non-polar (hydrophobic) amino acids such as alanine, leucine, isoleucine, valine, proline, phenylalanine, tryptophan, and methionine. Non-conservative amino acid changes can be made by substituting one amino acid that is within one of these groups with another amino acid within a distinct group.

As used herein, the phrase "NUCB1 protein variant" to refers to a non-naturally occurring form of the NUCB1 protein that comprises at least one mutation that inhibits calcium binding to the NUCB1 protein variant and that exhibits amyloid fibril disaggregation activity in the presence of calcium.

As used herein, the phrase "NUCB1 protein mutant" refers to a non-naturally occurring form of the NUCB1 protein.

As used herein, the phrase "operably linked" refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter and is linked such that the resulting translation product is in frame with the translational open reading frame that encodes the desired protein. Nucleic acid sequences that can be operably linked may be, for example, sequences that provide gene expression functions (i.e., gene expression elements such as promoters, 5' untranslated regions, introns, protein coding regions, 3' untranslated regions, polyadenylation sites, and/or transcriptional terminators), sequences that provide DNA transfer and/or integration functions, sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, site specific recombination sequences) and sequences that provide replication functions (i.e., bacterial origins of replication, autonomous replication sequences, centromeric sequences).

To the extent to which any of the preceding definitions is inconsistent with definitions provided in any patent or non-patent reference incorporated herein or in any reference found elsewhere, it is understood that the preceding definition will be used herein.

NUCB1 Protein Variants

NUCB1 protein variants can comprise any of i) truncated forms of NUCB1; ii) mutations that inhibit calcium binding; or ii) a combination of a truncated form of NUCB1 with mutations that inhibit calcium. NUCB1 variants capable of disaggregating amyloid fibrils are provided herein. Certain NUCB1 variants capable of inhibiting amyloid fibrils in the presence of calcium are also provided herein. Calcium is one of the most abundant mineral ions present in the body. The level of Ca2+ can vary from 100 nM in the cytosol to 500 nM in the ER (Paschen, Cell Calcium 29, 1-11, 2001). Extracellular concentrations of Ca2+ can vary between 1-1.25 mM and can increase up to 2 mM during Ca2+ flux (Irnius et al., Mendeleev Communications, 17, 216-217, 2007). Since the estimated disassociation constants ($K_D$) for Ca2+ binding to naturally occurring NUCB1 are 7 µM (for the N-terminal proximal EF hand domain) and 70 µM (for the C-terminal proximal EF hand domain), extracellular NUCB1 in its naturally occurring form is expected to bind calcium under most physiological conditions. In contrast, NUCB1 protein variants capable of disaggregating amyloid fibrils in the presence of physiological levels of calcium are provided herein. NUCB1 protein variants provided herein are capable of disaggregating amyloid fibrils in the presence of calcium at calcium concentrations from 200 micromolar to at least about 3 mM. In contrast, naturally occurring forms of the NUCB1 protein display significantly reduced amyloid fibril disaggregating activity in the presence of calcium at a concentration of 200 micromolar to at least 3 mM relative to the amyloid fibril disaggregating activity observed at those same calcium concentrations for the NUCB1 protein variants provided herein.

Another feature of the NUCB1 protein variants of the invention is that they comprise mutations that inhibit calcium binding. Calcium binding inhibition in the mutants is reflected in an increase in the dissociation constant ($K_D$) for calcium observed in the NUCB1 protein variant relative to that observed in a control NUCB1 protein that does not contain the mutation. NUCB1 protein variants can thus be identified by comparing the calcium binding activity of the variant to that of a control protein. Suitable calcium binding assays for identifying NUCB1 protein variants include, but are not limited to, assays where radioisotopic calcium binding to protein in solution or immobilized to a solid phase is determined. Competitive binding assays where displacement of the radioisotopic calcium by calcium can also be used to identify NUCB1 protein variants. Alternatively, calcium binding can be assayed in isothermal calorimetric titration experiments where changes in enthalpy associated with increasing concentrations of calcium are measured.

In certain embodiments, NUCB1 protein variants of the invention can comprise at least one substitution mutation and/or deletion mutation of six amino acids or less in a single loop region of an EF hand domain of the NUCB1 protein variant. Certain NUCB1 protein variant embodiments that comprise at least one substitution mutation and/or deletion mutation of six amino acids or less in a single loop region of an EF hand domain are thus structurally distinguished from other NUCB1 protein variants with any one of: i) a deletion of both EF hand domains or of both EF hand loop domains in their entireties; ii) a deletion of both EF hand domains or of both EF hand loop domains and the intervening acidic region in their entireties, iii) a deletion of the C-terminal proximal EF hand domain or C-terminal EF hand loop domains in their entireties, or iv) a deletion of the entire 12 amino acid loop domain of the first N-terminal proximal EF hand domain. In certain embodiments, a single loop region of the NUCB1 protein variant is mutated such that the variant can disaggregate fibrils in the presence of physiological levels of calcium at an increased rate relative to naturally occurring NUCB1 proteins. In preferred embodiments, the one substitution mutation and/or deletion mutation of six amino acids or less can be in a single loop region of an N-terminal proximal EF hand domain of the NUCB1 protein variant.

In certain embodiments, NUCB1 protein variants of the invention can comprise at least one mutation in each loop region of each EF hand domain of the NUCB1 protein variant. These particular NUCB1 protein variants that comprise at least one mutation in each loop region of each EF hand domain of the NUCB1 protein are thus structurally distinguished from other NUCB1 protein variants with any one of: i) a mutation in only one EF hand loop domain; ii) a deletion of both EF hand domains; iii) a deletion of both EF hand loop domains and the intervening acidic region, iv) a deletion of the C-terminal proximal EF hand domain, or v) a deletion of the entire 12 amino acid loop domain of the first N-terminal proximal EF hand domain. In certain embodiments, both loop regions of the NUCB1 protein variant are mutated such that the variant can disaggregate fibrils in the presence of physiological levels of calcium at an increased rate relative to naturally occurring NUCB1 proteins or to an NUCB1 variant protein with any one of: i) a mutation in only one EF hand loop domain; ii) a deletion of both EF hand domains; iii) a deletion of both EF hand domains and the intervening acidic region, iv) a deletion of the C-terminal proximal EF hand domain, or v) a deletion of the entire 12 amino acid loop domain of the first N-terminal proximal EF hand domain. Mutations in the loop regions can comprise substitution mutations of one or more amino acid residues within one or both loops, deletion mutations of any of 1, 2, 3, 4, 5 or 6 amino acid residues within the loop region residues of one or both loops, various combinations of such substitutions and deletions either within each individual loop region, or various combinations of substitutions/and or deletions within both loop regions.

Mutations in the 12 amino acid loop region of the first N-terminal proximal EF hand loop domain that can be used in a NUCB1 protein variants of the invention are provided as $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ (SEQ ID NO:7) wherein at least one residue in SEQ ID NO:7 is distinct from a corresponding residue of the 12 amino acid loop region of the first N-terminal proximal EF hand loop domain of NUCB1 (SEQ ID NO:9). In particular embodiments, residues $Xaa_1$, $Xaa_3$, $Xaa_5$, $Xaa_9$, and/or $Xaa_{12}$ of SEQ ID NO:7 in a NUCB1 protein variant can comprise a non-conservative substitutions in the corresponding residue of SEQ ID NO:9. Alternatively, residues $Xaa_1$, $Xaa_3$, $Xaa_5$, $Xaa_9$, and/or $Xaa_{12}$ of SEQ ID NO:7 in a NUCB1 protein variant can be deleted in certain embodiments. In certain embodiments, the corresponding 12 amino acid residues in a NUCB1 protein variant of SEQ ID NO:7 are:

$Xaa_1$ is alanine, serine, lysine, arginine, or aspartate;
$Xaa_2$ is isoleucine, leucine, valine; or alanine;
$Xaa_3$ is lysine, arginine, or asparagine;
$Xaa_4$ is serine or threonine;
$Xaa_5$ is lysine, arginine, or aspartate;
$Xaa_6$ is glycine, alanine, valine, leucine, or isoleucine;
$Xaa_7$ is glycine, alanine, valine, leucine, or isoleucine;
$Xaa_8$ is glycine, alanine, valine, leucine, or isoleucine;
$Xaa_9$ is lysine, arginine, aspartate or glutamate;
$Xaa_{10}$ is lysine, arginine, glutamate or aspartate;
$Xaa_{11}$ glutamine or asparagine;
$Xaa_{12}$ is alanine, serine, lysine, arginine, or glutamate;
wherein at least one residue in SEQ ID NO:7 is distinct from a corresponding residue of the 12 amino acid loop region of the first N-terminal proximal EF hand loop domain of NUCB1 (SEQ ID NO:9).

Mutations in the 12 amino acid loop region of a C-terminal proximal EF hand loop domain that can be used in a NUCB1 protein variant of the invention are provided as $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ (SEQ ID NO:8) wherein at least one residue in SEQ ID NO:8 is distinct from a corresponding residue of the 12 amino acid loop region of the second C-terminal proximal EF hand loop domain of NUCB1 (SEQ ID NO:10). In particular embodiments, residues $Xaa_1$, $Xaa_3$, $Xaa_5$, and/or $Xaa_{12}$ of SEQ ID NO:8 in a NUCB1 protein variant can comprise a non-conservative substitutions in the corresponding residue of SEQ ID NO:10. Alternatively, residues $Xaa_1$, $Xaa_3$, $Xaa_5$, and/or $Xaa_{12}$ of the corresponding residues of SEQ ID NO:8 in a NUCB1 protein variant can be deleted. In certain embodiments, the corresponding 12 amino acid residues in a NUCB1 protein variant of SEQ ID NO:8 are:

$Xaa_1$ is alanine, serine, lysine, arginine, or aspartate;
$Xaa_2$ is threonine or serine;
$Xaa_3$ is lysine, arginine, or asparagine;
$Xaa_4$ is glutamine or asparagine;
$Xaa_5$ is lysine, arginine, or aspartate;
$Xaa_6$ is arginine, lysine, alanine, glycine, valine, leucine, or isoleucine;
$Xaa_7$ is glycine, alanine, valine, leucine, or isoleucine;
$Xaa_8$ is glycine, alanine, valine, leucine, or isoleucine;
$Xaa_9$ is threonine or serine;
$Xaa_{10}$ is glycine, alanine, valine, leucine, or isoleucine;
$Xaa_{11}$ glutamate or aspartate; and
$Xaa_{12}$ is alanine, serine, lysine, arginine, or glutamate;
wherein at least one residue in SEQ ID NO:8 is distinct from a corresponding residue of the 12 amino acid loop region of the second C-terminal proximal EF hand loop domain of NUCB1 (SEQ ID NO:10).

Without seeking to be limited by theory, the $Xaa_1$, $Xaa_3$, $Xaa_5$, $Xaa_9$, and/or $Xaa_{12}$ residues of the loop domains of EF hand regions (i.e. SEQ ID NO:9 and SEQ ID NO:10) are typically acidic residues (aspartate or glutamate) or residues with amidic side chains such as asparagine, either of which can provide oxygen atoms that interact with positively charged calcium ions by attractive electrostatic interactions. Thus non-conservative substitutions at $Xaa_1$, $Xaa_3$, $Xaa_5$, $Xaa_9$, and/or $Xaa_{12}$ residues with positively charged basic residues (i.e. lysine or arginine) in the loop regions of the EF hand domains of the NUCB1 protein variants of the invention can provide repulsive electrostatic interactions that inhibit binding of positively charged calcium ions. Non-conservative substitutions at $Xaa_1$, $Xaa_3$, $Xaa_5$, $Xaa_9$, and/or $Xaa_{12}$ residues with non-polar residues (alanine, valine, leucine, or isoleucine) in either one or both loop region(s) of the EF hand domains in a NUCB1 protein variants of the invention can eliminate or reduce the number of attractive interactions with positively charged calcium ions. Residue $Xaa_6$ is typically a glycine that accommodates loop conformations that facilitate calcium ion binding. Consequently, the residue corresponding to $Xaa_6$ in either one or both EF hand loop region(s) of a NUCB1 protein variant can in certain embodiments be substituted with a non-polar amino acid with a bulkier side chain such as alanine, valine, or isoleucine.

In certain embodiments, NUCB1 protein variants of the invention comprise a single non-conservative amino acid substitution in a residue of the N-terminal EF hand loop domain (SEQ ID NO:7) and/or in a residue of the C-terminal EF hand loop domain (SEQ ID NO:8). In a certain embodiments, non-conservative substitutions of an acidic residues at $Xaa_1$, $Xaa_5$, and/or $Xaa_{12}$ of SEQ ID NO:7 and/or SEQ ID NO:8 are preferably with a basic residue (lysine or arginine), a non-polar residue, or a non-conservative residue that is not asparagine or glutamine. In other embodiments, non-conservative substitutions of a residue with an amidic side chain at $Xaa_3$ of SEQ ID NO:7 and/or SEQ ID NO:8 are preferably with a basic residue (lysine or arginine), a non-polar residue, or a non-conservative residue that is not an acidic residue (glutamate or aspartate). In still other embodiments, non-conservative substitutions of an acidic residue at $Xaa_9$ in SEQ ID NO:7 and/or SEQ ID NO:9 are preferably with a basic residue (lysine or arginine), a non-polar residue, or a non-conservative residue other than asparagine or glutamine. In certain preferred embodiments, the non-conservative substitution at position $Xaa_1$, $Xaa_3$, and $Xaa_5$ of both the N- and C-terminal EF hand loop domains are lysine or arginine. In certain preferred embodiments, the non-conservative substitution at position $Xaa_{12}$ of both the N- and C-terminal EF hand loop domains are alanine, lysine, or arginine. In still other preferred embodiments, $Xaa_1$ of both the N- and C-terminal EF hand loop domains is substituted with lysine and $Xaa_{12}$ of both the N- and C-terminal EF hand loop domains is substituted with alanine.

In other embodiments, NUCB1 protein variants of the invention can comprise two, three, four, or five non-conservative amino acid substitutions in residues in the N-terminal proximal EF hand loop domain (SEQ ID NO:7) and/or in residues in the C-terminal proximal EF hand loop domain (SEQ ID NO: 8). Non-conservative substitution of two, three, four, or five non-conservative amino acid substitutions in $Xaa_1$, $Xaa_3$, $Xaa_5$, $Xaa_9$, and/or $Xaa_{12}$ of the N-terminal proximal loop region (SEQ ID NO:7) and/or $Xaa_1$, $Xaa_3$, $Xaa_5$, and/or $Xaa_{12}$ of the C-terminal proximal domain (SEQ ID NO:8) are provided herein. In a certain embodiments, non-conservative substitutions of more than one of the acidic residues at $Xaa_1$, $Xaa_5$, and/or $Xaa_{12}$ are made, where the substitutions preferably comprise non-conservative substitutions of a basic residue (lysine or arginine), a non-polar residue, or a non-conservative residue that is not asparagine or glutamine. In other embodiments, the substitutions of multiple residues within one or both EF hand loops comprise a non-conservative substitutions of a residue with an amidic side chain at $Xaa_3$ are made, where the substitutions preferably comprise non-conservative substitutions of a basic residue (lysine or arginine), a non-polar residue, or a non-conservative residue that is not an acidic residue (glutamate or aspartate). In still other embodiments, the substitutions of multiple residues within one or both EF hand loop(s) comprise non-conservative substitutions of an acidic residue at $Xaa_9$ in SEQ ID NO:7 or SEQ ID NO:9, where the substitutions preferably comprise non-conservative substitutions of a basic residue (lysine or arginine), a non-polar residue, or a non-conservative residue other than asparagine or glutamine. In certain preferred embodiments, the non-conservative substitutions at positions $Xaa_1$, $Xaa_3$, and $Xaa_5$ of both the N- and C-terminal EF hand loop domains (i.e. SEQ ID NO:7 and SEQ ID NO:8, respectively) are lysine or arginine. In certain preferred embodiments, the non-conservative substitutions at position $Xaa_{12}$ of both the N- and C-terminal EF hand loop domains are alanine, lysine, or arginine. In another preferred embodiment, double non-conservative substitutions of SEQ ID NO:7 and/or SEQ ID NO:8 in a NUCB1 protein variant can comprise non-conservative substitutions of residues $Xaa_1$ and $Xaa_{12}$. In still other preferred embodiments, double non-conservative substitutions of SEQ ID NO:7 and/or SEQ ID NO:8 in a NUCB1 protein variant comprise a substitution of $Xaa_1$ with lysine and a substitution of $Xaa_{12}$ with alanine.

In certain embodiments, amino acid substitutions of both the $Xaa_1$ and $Xaa_{12}$ residues of a loop domain of one or both EF hand regions of a NUCB1 protein variant can be paired such that when a large amino acid residue is substituted at one of $Xaa_1$ or $Xaa_{12}$, a smaller amino acid residue is substituted at the other position (i.e at $Xaa_1$ if a large residue is substituted at $Xaa_{12}$ or at $Xaa_{12}$ if a large residue is substituted at $Xaa_1$). Thus, a substitution of lysine or arginine at $Xaa_1$ can be paired with a substitution of an alanine or a serine at $Xaa_{12}$. Alternatively, a substitution of an alanine or a serine at $Xaa_1$ can be paired with a substitution of lysine or arginine at $Xaa_{12}$.

NUCB1 protein variants comprising any of the combinations of deletion or substitution mutations in one or both loop regions of NUCB1 can be made in the context of various NUCB1 proteins or NUCB1 mutant proteins. In certain embodiments, NUCB1 protein variants that comprise deletion or substitution mutations in one or both loop regions provided herein can also comprise an N-terminal deletion of NUCB1 that does not encompass both EF hand loop domains. Deletions of NUCB1 protein variants where about 1 to about 64 amino acids are deleted from the N-terminus of the protein and that comprise deletion or substitution mutations in one or both loop regions are provided. In other embodiments, NUCB1 variant proteins can comprise proteins where about 64, about 32, about 31, about 26, about 24, or about 20 amino acids are removed from the N-terminus of the NUCB1 protein variant and that comprise deletion or substitution mutations in one or both loop regions are provided. In still other embodiments, the NUCB1 protein variants provided herein that comprise deletion or substitution mutations in one or both loop regions can also comprise a C-terminal deletion of NUCB1 that does not encompass both EF hand loop domains. Deletions of NUCB1 protein variants that comprise deletion or substitution mutations in one or both loop regions and wherein about 1 to about 130 amino acids are deleted from the C-terminus of the protein are provided. In other embodiments, NUCB1 variant proteins that comprise deletion or substitution mutations in one or both loop regions and can also comprise proteins where about 128, about 100, about 54, about 30, about 10, about 5, about 2 amino acids or 1 amino acid are/is removed from the C-terminus of the NUCB1 protein variant. NUCB1 protein variants comprising combinations of N- and C-terminal deletions that do not encompass deletions of both EF hand loop domains are also provided.

NUCB1 protein variants comprising a combination of: i) a deletion of either the N-terminal or C-terminal EF hand loop domain in its entirety with ii) one or more substitution mutation(s) and/or deletions of six amino acids or less of the other EF hand loop domain are also provided. In certain embodiments, NUCB1 protein variants that comprise an N-terminal or internal deletion of the N-terminal EF hand loop domain, where the deletion comprises the loop domain in either in its entirety or in part, are combined with one or more substitution mutation(s) and/or deletions of six amino acids or less of the C-terminal EF hand loop domain. Thus, a NUCB1 protein variant can in certain embodiments comprise: i) an N-terminal deletion of residues 1-264, an internal deletion of residues 253 to 264, or an internal deletion from any residue between 246 to 253 and residue 264, where residue numbers refer to SEQ ID NO:2, a corresponding sequence in SEQ ID NO:1 or other equivalent NUCB1 protein and ii) one or more substitution mutation(s) and/or deletions of six amino acids or less of the C-terminal EF hand loop domain. In certain embodiments, NUCB1 protein variants that comprise a C-terminal or an internal deletion of the C-terminal EF hand loop domain, where the deletion comprises the loop domain in either in its entirety or in part, are combined with one or more substitution mutation(s) and/or deletions of six amino acids or less of the N-terminal EF hand loop domain. Thus, a NUCB1 protein variant can in certain embodiments comprise: i) a C-terminal deletion of residues 305 to 461, an internal deletion of residues 305 to 316, or an internal deletion from residue 305 to any residue between 317 to 461, where residue numbers refer to SEQ ID NO:2, a corresponding sequence in SEQ ID NO:1 or other equivalent NUCB1 protein and ii) one or more substitution mutation(s) and/or deletions of six amino acids or less of the N-terminal EF hand loop domain.

Certain NUCB1 protein variants provided herein have also been shown herein to exhibit peptidase activity. Without seeking to be limited by theory, such peptidase activity potentially provides in part for either one or both of the amyloid fibril disaggregation and/or amyloid fibril formation inhibition activities observed by NUCB1 protein variants provided herein. In certain embodiments, the NUCB1 protein variants comprise one or more motifs characteristic of carboxypeptidases that include NQHTFEARDLELL (SEQ ID NO:21), GLDPNRFNP (SEQ ID NO:22), and DGHFREKLQAA (SEQ ID NO:23). Such motifs are present in NUCB1 (SEQ ID NO:2) at residues 145 to 157 (for SEQ ID NO:21), residues 237 to 245 (for SEQ ID NO:22), and residues 65 to 75 (for SEQ ID NO:23). The carboxypeptidase motifs are also present in the corresponding positions of certain NUCB1 protein variants embodied by SEQ ID NO:1 and SEQ ID NO:6. However, NUCB1 protein variants comprising one or more carboxypeptidase motifs that comprise one or more amino acid substitutions in residues corresponding to those of SEQ ID NO:21, SEQ ID NO:22, or SEQ ID NO:23 are also provided herein. Such substitutions are preferably conservative amino acid substitutions. In certain embodiments, non-conservative substitutions in one or more carboxypeptidase motifs can be tolerated. Maintenance of peptidase activity in such variants comprising substitutions in carboxypeptidase motifs of SEQ ID NO:21, SEQ ID NO:22, or SEQ ID NO:23 can be determined by a peptidase assay.

NUCB1 protein variants provided herein have also been shown herein to exhibit zinc binding activity. Without seeking to be limited by theory, such zinc binding activity potentially provides in part for either one or both of the amyloid fibril disaggregation and/or amyloid fibril formation inhibition activities observed by NUCB1 protein variants provided herein. Zinc binding activity of NUCB1 protein variants can be categorized as either a) high affinity zinc binding or b) low affinity zinc binding. In certain embodiments, NUCB1 protein variants can thus be characterized by the presence of high or low affinity zinc binding. Zinc binding of NUCB1 protein variants can be determined by any appropriate assay, including but not limited to assays that: a) monitor enhanced tyrosine or phenylalanine fluorescence as zinc concentration is increased; b) monitor enhanced BIS-ANS Fluorescence of the NUCB1 protein variant in the presence of increasing 1,10-phenanthroline; and/or c) microcalorimetry experiments where effects of increasing the molar ratios of zinc to the NUCB1 protein variant are determined.

NUCB1 protein variants provided herein have also been shown herein to exhibit the ability to bind to Amylin "protofibrils" or pre-fibrillar species. Such binding may prevent the pre-fibrillar species from assembly into fibrils and might reduce the cellular toxicity of the pre-fibrillar species by capping their growing ends.

NUCB1 protein variants comprising any of the combinations of deletion or substitution mutations in one or both loop regions of NUCB1 can be made in the context of various NUCB1 proteins or NUCB1 mutant proteins that comprise variant amino acid residues in regions outside of the EF hand loop regions of NUCB1 or deletions of one or more N-terminal, C-terminal, or internal amino acid residue(s). In certain embodiments, NUCB1 protein variants can be derived from naturally occurring NUCB1 sequences that include SEQ ID NO:2 (Gen Bank accession NP_006175.2) or naturally occurring NUCB1 proteins that comprise a substitution of leucine at residue 12 for proline, a substitution of tyrosine at residue 190 for asparagine, a substitution of arginine at residue 199 for lysine, a substitution of methionine at residue 338 for valine, or a substitution of glutamine at residue 385 for lysine. In certain embodiments, these NUCB1 protein variants can comprise conservative or non-conservative substitutions of residues in one of the naturally occurring NUCB1 sequences that are in regions outside of the EF hand loop regions of NUCB1.

In certain embodiments, a NUCB1 protein variant comprising at least one mutation(s) and/or deletion(s) in one or both EF hand loop domains can be made in the context of the NUCB1 protein variant sequence of SEQ ID NO:1. NUCB1 proteins variants of SEQ ID NO:1 that comprise the aforementioned substitutions or deletions of one or more EF hand loop domain residues corresponding to those of SEQ ID NO:7 and/or SEQ ID NO:8 are also provided. In certain embodiments that comprise a NUCB1 protein variant of SEQ ID NO:1, EF hand loop domain residues corresponding to those of SEQ ID NO:7 and/or SEQ ID NO:8 are distinct from the corresponding EF hand loop domain residues of SEQ ID NO:9 and SEQ ID NO:10, respectively. In other embodiments, NUCB1 protein variants that that comprise the aforementioned substitutions or deletions of one or more EF hand loop domain can have at least 85%, 90%, 95%, 98%, or 99% sequence identity to SEQ ID NO:1.

Isolated Nucleic Acids Encoding NUCB1 Protein Variants

Isolated nucleic acids that encode the NUCB1 protein variants are also provided herein. Isolated nucleic acids that encode NUCB1 protein variants can further comprise an operably linked nucleic acid that encodes a signal peptide that provides for secretion of the NUCB1 protein variant in a host cell. Such signal peptides are typically selected based on their ability to support secretion in a selected host cell. Operable linkage of the nucleic acid encoding the NUCB1 protein variant with signal peptides that provide for secretion of the NUCB1 protein variant in mammalian, insect, yeast, or bacterial cells is thus contemplated.

In other embodiments, the isolated nucleic acids that encode NUCB1 protein variants can further comprise an operably linked nucleic acid that encodes a purification tag. A purification tag can be operably linked to either the N- or C-terminus of the NUCB1 protein variant. A purification tag is any peptide sequence that provides for facilitated purification of the linked NUCB1 protein variant. Purification tags include, but are not limited to, a histidine tag, a heavy chain of protein C tag, a streptavidin tag, a calmodulin binding protein tag, covalent yet dissociable NorpD tags, GST tags, epitope tags, and maltose binding protein tags. The use of affinity tags in protein purification is described by Lichty et al., in Protein Expr Purif. 2005 May; 41(1):98-105.

In other embodiments, the isolated nucleic acids that encode NUCB1 protein variants can further comprise an operably linked nucleic acid that encodes a protease cleavage site. In certain embodiments, the protease cleavage site is operably linked to a purification tag such that the purification tag can be cleaved from either the N- or C-terminus of the NUCB1 protein variant by treating the fusion protein with protease after purification. Useful protease cleavage sites include, but are not limited to, the PreScission™ Protease recognition sequence that can be cleaved with a rhinovirus 3C protease (GE Healthcare, Inc., Piscataway, N.J.), thrombin cleavage sites that can be cleaved with thrombin, and the like.

It is further understood that the isolated nucleic acids that encode NUCB1 protein variants can further comprise an operably linked nucleic acids that provide for expression in a host cell. Thus, operable linkage of the isolated nucleic acids that encode NUCB1 protein variants to promoters, 5' untranslated leader sequences, ribosome binding sites, transcriptional termination sequences, and/or polyadenylation sequences that provide for expression of the NUCB1 protein in various host cells is contemplated herein.

Isolated nucleic acids that encode NUCB1 protein variants can also comprise operably linked vector sequences including, but not limited to sequences that provide for autonomous replication in a host cell, sequences that provide for integration in a host cell, sequences that encode selectable marker encoding genes that provide for selection of a transformed host cell, and the like.

Isolated nucleic acids provided herein also comprise a variety of distinct nucleic acid sequences that encode NUCB1 protein variants due to the degeneracy of the genetic code. Such nucleic acids can be derived either by mutagenesis of naturally occurring NUCB1 nucleic acid sequences or by de novo synthesis. Embodiments where the codons of the isolated nucleic acid are changed to reflect the A+T content of a host organism are also contemplated herein.

Cells Comprising Nucleic Acids that Encode NUCB1 Protein Variants

The invention also provides cells that comprise nucleic acids that encode NUCB1 protein variants. It is understood that this terms refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation techniques. As used herein, the terms "transformation" includes any method whereby an exogenous nucleic acid is introduced into a cell. Transformation methods thus include, but are not limited to, calcium phosphate or calcium chloride co-precipitation, DEAE-dextran-mediated transfection, lipofection, particle mediated delivery, or electroporation.

To obtain transformed cells, a gene that encodes a selectable marker is generally introduced into the host cells along with the gene of interest. For prokaryotic cells, selectable markers include, but are not limited to, genes that confer resistance to antibiotics, genes that confer the ability to grow in the absence of otherwise required nutrients and the like. For eukaryotic cells, selectable markers that confer resistance to drugs including, but not limited to, G418, hygromycin, zeocin and methotrexate can be used.

Methods of Producing NUCB1 Protein Variants

Further provided are vectors comprising any of the nucleic acids of the invention or host cells engineered to express the nucleic acids of the invention. In specific embodiments, the vectors comprise a nucleotide sequence which regulate the expression of the protein encoded by the nucleic acid of the invention. For example, the nucleotide sequence encoding the protein of the invention can be operably linked to a inducible promoter.

Host cells comprising the nucleic acids and vectors of the invention are also provided. In certain embodiments, the vector or nucleic acid is integrated into the host cell genome; in other embodiments, the vector or nucleic acid is extrachromosomal. A host cell can be a mammalian cell, a yeast cell, and insect cell or a bacterial cell. The bacterial host cell can be an *E. coli* cell.

In considering all of the various host systems for expression of NUCB1 protein variants, it is appreciated that host-appropriate systems that provide for either intracellular or extracellular expression of the NUCB1 protein variants can be used. In this regard, it is understood that about the first 24 to 26 amino acids of the naturally occurring form of NUCB1 (SEQ ID NO:2) comprise a signal peptide sequence that is cleaved from the mature, extracellular form of NUCB1 upon expression and secretion in mammalian host cells. Thus, NUCB1 variant proteins can be expressed intracellularly by construction of vectors encoding NUCB1 protein variants where about 1 to about 32 amino acids are deleted from the N-terminus of the expressed protein. In other embodiments, NUCB1 variant proteins can be expressed intracellularly by construction of vectors encoding NUCB1 protein variants where about 32, about 31, about 26, about 24, or about 20 amino acids are removed from the N-terminus of the NUCB1 protein variant. N-terminal deletion mutants of NUCB1 can be N-terminally fused to other proteins or peptide sequences that provide for other desired characteristics including, but not limited to, improved stability, affinity purification, improved pharmacokinetic properties, and/or improved delivery to a target organ. In certain embodiments, N-terminal fusions to the NUCB1 protein variant are operably linked by a protease recognition site that can facilitate removal of the N-terminal fusion protein or peptide either in vivo or in vitro.

In considering all of the various host systems for expression of NUCB1 protein variants, it is also appreciated that host-appropriate systems that provide for extracellular expression of the NUCB1 protein variants can be used. In such vectors, secretion signal sequences that provide for secretion of NUCB1 variant proteins in the desired host cell are operably linked to the N-terminus of the NUCB1 variant protein. Mammalian secretion signals include, but are not limited to, a native NUCB1 signal sequence, a tPA signal peptide, a mammalian alkaline phosphatase signal peptide and the like. Yeast secretion signals include, but are not limited to, a yeast alpha mating type signal peptide, a yeast invertase signal peptide, or yeast alkaline phosphatase signal peptide and the like. Insect cell secretion signals include, but are not limited to, an egt signal peptide, a p67 signal peptide, or other signal peptides useful for expression of heterologous proteins as disclosed in U.S. Pat. No. 5,516,657.

The recombinant expression vectors of the invention comprise nucleotide sequence encoding a NUCB1 protein variant of the invention in a form suitable for expression in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, ribosome binding sites, transcriptional terminators, and other expression control elements (e.g., polyadenylation signals). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of NUCB1 protein variant desired, etc. The expression vectors of the invention can be introduced into host cells to thereby produce NUCB1 protein variants encoded by nucleic acids as described herein.

The recombinant expression vectors of the invention can be designed for expression of a NUCB1 protein variant of the invention in prokaryotic (e.g., E. coli) or eukaryotic cells (e.g., insect cells (using baculovirus expression vectors), yeast cells or mammalian cells). Alternatively, the recombinant expression vector can be transcribed and translated in vitro, for example using T7 promoter regulatory sequences and T7 polymerase and an in vitro translation system.

Expression of NUCB1 variant proteins in prokaryotes can be carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of the recombinant NUCB1 protein variant protein; 2) to increase the solubility of the recombinant NUCB1 protein variant protein; and 3) to aid in the purification of the recombinant NUCB1 protein variant protein by acting as a ligand in affinity purification. Often, in fusion expression vectors, a proteolytic cleavage domain is introduced at the junction of the fusion moiety and the recombinant protein to enable separation of the recombinant protein from the fusion moiety subsequent to purification of the fusion protein. Thus, the fusion moiety and proteolytic cleavage domain together can act as an activation sequence, including a protease recognition site, for recombinant expression of an NUCB1 protein variant protein. Such enzymes, and their cognate recognition sequences, include Factor Xa, thrombin, rhinovirus 3C protease and enterokinase. Typical fusion expression vectors include pGEX (Pharmacia Biotech Inc; Smith and Johnson (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. N-terminal fusions of a "Hisx6" tag to the N-terminus of NUCB1 protein variants can provide for efficient purification of NUCB1 protein variants via NI-NTI chromatography. Illustrative examples of vectors that provide for N-terminal Hisx6 fusions include, but are not limited to, pET28 vectors (Novagen, Inc., Madison, Wis., USA) and modifications thereof. The pET vector system and appropriate host cells are described in (Studier et al., Gene Expression Technology: Methods in Enzymology 185, Academic Press, San Diego, Calif. (1990) 60-89).

Examples of suitable inducible non-fusion E. coli expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant NUCB1 variant protein expression in E. coli is to express the protein in a host bacteria with an impaired capacity to proteolytically cleave the recombinant protein (Gottesman, Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast S. cerevisiae or P. pastoris include pYepSec1 (Baldari et al., (1987) EMBO J. 6:229-234), pMFa (Kurjan and Herskowitz, (1982) Cell 30:933-943), pJRY88 (Schultz et al., (1987) Gene 54:113-123), pYES2 (Life Technologies Corporation, San Diego, Calif.), and pPicZ (Life Technologies Corp, San Diego, Calif.). For expression in Pichia, a methanol-inducible promoter is preferably used. Alteration of the nucleic acid sequence of the nucleic acid to be inserted into an expression vector so that the individual codons for each amino acid are those preferentially utilized in yeast is also contemplated herein.

Alternatively, the expression vector is a baculovirus expression vector. Baculovirus vectors available for expression of proteins in cultured insect cells (e.g., Sf 9 cells) include the pAc series (Smith et al. (1983) Mol. Cell Biol. 3:2156-2165) and the pVL series (Luckow and Summers (1989) Virology 170:31-39). Another strategy is to alter the nucleic acid sequence of the nucleic acid to be inserted into an expression vector so that the individual codons for each amino acid are those preferentially utilized in insect cells.

In yet another embodiment, an NUCB1 protein variant protein is expressed in mammalian cells using a mammalian expression vector. Examples of mammalian expression vectors include pCDM8 (Seed (1987) Nature 329:840) and pMT2PC (Kaufman et al., (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra. It is also anticipated that either the pcDNA3™ vector or pIND™ vector (both from Life Technologies, Carlsbad, Calif., USA) could be used to express NUCB1 protein variants in mammalian cells as Lin et al., used these vectors to express various NUCB1 proteins, including those where one or both EF hand loop regions are deleted (Lin et al., J Cell Biol. 1999 Apr. 19; 145(2):279-89). Mammalian expression systems are thus contemplated to be particularly useful for expression of NUCB1 protein variants that comprise deletions in one or more EF hand loop domains.

Pharmaceutical and Veterinary Compositions Comprising NUCB1 Protein Variants and Methods of Administration In practicing any of the above referenced methods involving administration of amyloidosis treatment agents to a subject, it is contemplated that a variety of pharmaceutical or veterinary compositions comprising these active agents can be administered by a variety of techniques. Such pharmaceutical or veterinary compositions may be formulated in various ways known in the art for administration purposes. To prepare the pharmaceutical or veterinary NUCB1 protein variant compositions, an effective amount of the NUCB1 protein variant as the active ingredient is combined with one or more pharmaceutically acceptable carriers and delivery vehicles. Numerous pharmaceutically acceptable carriers and delivery vehicles exist that are readily accessible and well known in the art, which may be employed to generate the preparation desired (i.e., that permit administration of the pharmaceutical composition orally, topically, rectally, percutaneously, by parenteral injection, by intrathecal injection, targeted organ injection, intranasally or by inhalation). Representative examples of pharmaceutically acceptable carriers and delivery vehicles include aluminum stearate, lecithin, serum proteins, such as human serum albumin; buffer substances such as the various phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, and zinc salts, colloidal silica, magnesium trisilicate, polyvinyl pyrrolidone, cellulose-based substances, polyethylene glycol, sodium carboxymethylcellulose, polyacrylates, waxes, polyethylene, polyoxypropylene-block polymers, polyethylene glycol and wool fat, and the like. The pharmacologic compositions described herein may further be prepared in unitary dosage form suitable for administration orally, percutaneously, by parenteral injection (including subcutaneous, intramuscular, intravenous and intradermal), by intrathecal injection, targeted organ injection, topically, intranasally, by inhalation, or for application to a medical device, such as an implant, catheter, or other device. In preparing the compositions that permit administration of an oral dosage, for example, any of the pharmaceutically acceptable carriers known in the art may be used, such as water, glycols, oils, alcohols and the like in the case of carriers that permit oral delivery of liquid preparations such as suspensions, syrups, elixirs and solutions. When solid pharmaceutically acceptable carriers are desired that permit oral or rectal administration, starches, sugars, kaolin, lubricants, binders, cellulose and its derivatives, and disintegrating agents and the like may be used to prepare, for example, powders, pills, capsules and tablets. For pharmaceutically acceptable carriers that permit parenteral administration, the pharmaceutically acceptable carriers often comprise sterile water, which may be supplemented with various solutes to, for example, increase solubility. Injectable solutions may be prepared in which the pharmaceutically acceptable carrier comprises saline solution, glucose solution, or a mixture thereof, which may include certain well-known anti-oxidants, buffers, bacteriostats, and other solutes that render the formulation isotonic with the blood of the intended patient.

Supplementary active compounds can also be incorporated into the pharmaceutical or veterinary compositions disclosed herein. Compositions, formulations, and methods of delivering protein therapeutics to subjects are described by Pawar et al., Expert Opin Biol Ther. August; 4(8):1203-12, 2004, which is hereby incorporated by reference in its entirety.

Given that certain amyloid based diseases are associated with certain organs, it is further contemplated that pharmaceutical compositions for use in treating those disease will be tailored to use in the affected organs. Embodiments for treatment of amyloidosis of the brain associated with amyloid beta fibrils will comprise pharmaceutically acceptable carriers and formulations suited for delivery to the brains of subjects suffering from such disease. In certain embodiments, the NUCB1 protein variant will be combined with a polymer. This polymer can provide for sustained and/or controlled release of the NUCB1 protein variant. Polymers suitable for delivery of NUCB1 to the brain and other organs include, but are not limited to, alginates, chitosan, collagen, fibrins, methoxy poly(ethylene glycol), polyanhydrides, poly(e-caprolactone), poly(ethylene oxide), poly(lactic acid), poly-lactide-co-glycolide (PLGA), poly(ortho esters), polyethylene vinyl-co-acetate (EVAc), polyethylene glycol (PEG), polyester-PEG triblock copolymers, polyphosphazenes, poly[(sebacic-co-(ricinoleic acid)], ricinoleic acid, silicone, and combinations thereof. Formulation of polymers with pharmaceutically active proteins into microspheres and three-dimensional implants that are suitable for delivery of pharmaceutically active polymers to the Central Nervous System is described by Whittlesey and Shea in Exp Neurol. 190:1-16, 2004, which is hereby incorporated by reference in its entirety. Descriptions of polymeric formulations appropriate for delivery of pharmaceutically active agents including proteins to various organs is also described by in Chitkara Macromol Biosci. 8; 6(12):977-90, 2006, which is hereby incorporated by reference in its entirety. Therapeutically effective amounts of a pharmaceutical composition comprising the NUCB1 protein variant can be administered by parenteral injection, by injection into an organ, implantation of a pump, stereotactic delivery, implantation of a cannula, implantation of a three-dimensional implant, or implantation of microspheres.

Given the rapid action of the NUCB1 protein variants on amyloid fibrils, it is further contemplated that pharmaceutical compositions provided herein can be directly applied to regions within an affected organ of a subject that comprise amyloid fibril deposits. Such direct applications could be accomplished in conjunction with imaging methods that indicate regions comprising the amyloid fibril deposits.

Methods of Treating Amyloidosis

Methods of treating subjects afflicted by amyloidosis with pharmaceutical or veterinary compositions are also provided herein. In certain embodiments, the pharmaceutical or veterinary compositions used in the methods of treatment can comprise a NUCB1 variant protein comprising a mutation in both loop regions of the N-terminal EF hand domain and the C-terminal EF hand domain of the protein wherein the mutations inhibits calcium binding. NUCB1 protein variants exhibit the capability of disaggregating fibrillar deposits formed by entirely distinct amyloid proteins that include, but are not limited to, amylin and amyloid beta 42 (Aβ42), it is believed that the NUCB1 protein variants are capable of treating a wide variety of amyloid-based diseases. Without seeking to be limited by theory, it is possible that the ability of the NUCB1 protein variants to disaggregate fibrils derived from entirely distinct amyloid proteins is due to recognition of a common structural feature of the aggregated fibrils by the NUCB1 protein variants rather than to recognition of an amino acid sequence motif associated with just one amyloid protein.

In certain embodiments, the pharmaceutical or veterinary compositions used in the methods of treatment can comprise a NUCB1 variant protein comprising a substitution or a deletion mutation in either the N-terminal EF hand domain or the C-terminal EF hand domain of the protein wherein the mutation inhibits calcium binding to the NUCB1 variant protein and wherein the NUCB1 variant protein has amyloid fibril disaggregating activity.

The use of NUCB1 protein variants in treatment of certain specific amyloid associated diseases is contemplated. In one embodiment, the use of NUCB1 protein variants to treat type 2 diabetes associated with accumulation of amylin fibrils is provided. Such treatments would comprise administration of therapeutically effective amount of a NUCB1 protein variant to a subject suffering from amylin fibril-mediated type 2 diabetes, preferably targeting delivery to the pancreas or regions within the pancreas with accumulations of amylin fibrils.

In other embodiments, the use of NUCB1 protein variants to treat Alzheimers disease, dementia, memory loss or other manifestations of CNS disease associated with accumulation of amyloid beta 42 (Aβ42) fibrils and/or amyloid beta 40 fibrils in the CNS is provided. In certain embodiments, such treatments would comprise administration of therapeutically effective amount of a NUCB1 protein variant to a subject suffering from amyloid beta 42 (Aβ42) fibril related neurological disorders comprising Alzheimer's disease, dementia, memory loss, and the like. In certain embodiments, it is anticipated that a NUCB1 protein variant would be delivered directly to the CNS by injection. In still other embodiments, a NUCB1 protein variant would be delivered directly to certain regions of the CNS by stereotactic techniques.

In addition to methods of treatments that provide for slowing the progression of Alzheimers disease in afflicted subjects, it is also contemplated that the NUCB1 protein variants can be used in methods whereby Alzheimer's disease symptoms are at least partially reversed. In certain embodiments, the methods can comprise treatments that result in a reduction in the severity of disease. Such reductions in disease severity can be measured according to a clinical scale. Clinical scales used to establish reductions in disease severity include, but are not limited to, the Global Deterioration Scale (Reisberg et al., Am J Psychiatry. 1982 September; 139(9):1136-9), the Clinical Dementia Rating, the Functional Assessment Staging procedure, and the like (Reisberg et al., Int Psychogeriatr. 2007 June; 19(3):421-56).

A list of the amyloid disease of humans that may be treated with a NUCB1 protein variants or with nucleic acids encoding the NUCB1 protein variants is provided below.

TABLE 1

Amyloid associated diseases treatable with NUCB1 Protein Variants.

| Disease | Protein(s) Involved | Clinical Feature | GenBank Accession (protein) |
| --- | --- | --- | --- |
| Alzheimer's | Amyloid β and tau | Progressive dementia | Tau: S66627 APP: P05067 |
| Parkinson's | α-Synuclein | Movement Disorder | AAS83394 |
| Huntington's | Huntingtin | Dementia, motor and psychiatric problems | P42858 |
| Prion Diseases | Mutant isoforms of the wt PrP protein | dementia, ataxia, insomnia, paraplegia, paresthesias, and deviant behavior. | AAB35416 |
| Type 2 Diabetes Mellitus | Amylin or hIAPP | Amyloid deposits if amylin causing loss of Ister of Langerhans | P10997 |
| Dialysis-related amyloidosis (DRA) | β₂-microglobulin | Numbness or tingling associated with muscle weakness, in fingers and hands | NP_004039 |
| Amyotrophic lateral sclerosis | Superoxide dismutase | Movement Disorder | P00441 |
| Pick's Disease | tau | Atrophy of the frontal and temporal lobes of the brain | AAI14949 |
| Senile systemic amyloidosis | TTR (Transthyretin) | Peripheral Neuropathy | NP_000362 |
| Machado-Joseph Disease | Ataxin-3 | Lack of muscle control | NP_001019802 |
| Gelsolin Amyloid Disease | Gelsolin | Severe ataxia with neuropathy | NP_000168 |

TABLE 1-continued

Amyloid associated diseases treatable with NUCB1 Protein Variants.

| Disease | Protein(s) Involved | Clinical Feature | GenBank Accession (protein) |
|---|---|---|---|
| Primary systemic amyloidosis | Immunoglobulin (Ig) light chain | Cutaneous findings as evidence of underlying plasma cell dyserasia | CAA6153 CAA6155 CAA6157 |
| Secondary systemic amyloidosis | Serum Amyloid A | Chronic inflammatory condition like rheumatoid | NP_000322 |
| Familial non-neuropathic amyloidosis | Lysozyme | Arthritis, sarcoidosis, crohn's disease etc | CAA32175 |
| Familial subepithelial corneal amyloid | Lactotransferrin | Severe photophobia, tearing and an ocular foreign body sensation | NP_002334 |
| Hereditary renal amyloidosis | Fibrinogen | Sicca syndrome and renal disease | NP_000499 |
| Pituitary-gland amyloidosis | Prolactin | Mass arising from the pituitary gland with suprasellar extension | NP_000939 |
| Injection-localized amyloidosis | insulin | Histological analysis of the injection sites demonstrated foreign body type granulomas surround areas of amyloidogenesis | AAN39451 |
| Atrial amyloidosis | Atrial natriuretic factor | Isolated atrial Amyloid deposits, highly prevalent in elderly people with long-standing congestive heart failure | NP_006163 |
| Familial British dementia | BriL | Autosomal dominant condition characterized by dementia, progressive spastic tetraparesis and cerebellar ataxis | NP_001020466 |
| Hereditary cerebral amyloid angiopathy | Cystatin-c | Repeated hemorrhages leading to paralysis | CAA36497 CAA43856 |
| Familial amyloid polyneuropathy III | Apolipoprotein A1 | Peripheral polyneuropathies including multiple cranial nerves, corneal dystrophy and skin changes | NP_000030 |
| Chronic obstructive pulmonary disease | α1-antichymotrypsin | Cough, sputum production | NP_001076 |

It is further contemplated that amyloidosis in various animals can be treated with veterinary compositions comprising a NUCB1 variant protein or nucleic acids encoding the same. Veterinary amyloidoses including but not limited to those of the hepatic or renal system can be treated with the veterinary compositions of the invention. Veterinary amyloidoses including but not limited to those resulting of formation of serum amyloid A fibrils or AA fibrils can be treated with the veterinary compositions of the invention. It is further anticipated that veterinary subjects including but not limited to non-human primates, cattle, pigs, horses, goats, sheep, and companion animals such as cats and dogs suffering from amyloidosis can be treated with the veterinary compositions of the invention. The use of NUCB1 protein variants derived from the native NUCB1 protein of the subject to be treated is also contemplated.

Pharmaceutical compositions comprising nucleic acids that encode the NUCB1 protein variants of the invention is also provided. In certain embodiments, such nucleic acids would comprise lentiviral vectors that could be introduced into the brains or other afflicted organs of subjects suffering from amyloidosis. Delivery of potentially therapeutic proteins to the brains of afflicted subjects has been described (J Neurosci. 2003 Mar. 15; 23(6):1992-6).

Kits

In certain embodiments contemplated herein, the kits comprising a pharmaceutical or veterinary composition with a therapeutically effective amount of a nucleobindin 1 (NUCB1) protein variant and a pharmaceutically acceptable carrier as well as one or more containers are provided.

The composition(s) of the kit may be provided as a liquid solution or as a dried powder. In certain embodiments, the composition(s) are provided in a liquid solution. The liquid solution that can be an aqueous solution. When the composition(s) provided are a dry powder, the powder can be reconstituted by the addition of a suitable solvent, that may also be provided.

The container will generally include a vial into which the pharmaceutical or veterinary composition may be placed, and preferably suitably aliquoted. The kits of the present invention will also typically include a means for containing the recombinant protein, recombinant vector and/or cells in a container in close confinement for commercial sale. Such containers may include injection or blow-molded plastic containers into which the desired vials are retained.

The kit can also comprise a device or a component of a device for performing the methods of the invention. Devices, or components of devices, include, but are not limited to, syringes and other implements useful for delivery of the composition to the blood stream, a specific organ, or the CNS. In certain embodiments, the compositions of the invention can be provided in unit dose form. In addition or in the alternative, the kits of the invention can provide an instructional material which describes performance of one or more methods of the invention, or a notice in the form prescribed by a governmental agency regulating the manufacture, use or sale of pharmaceuticals or biological products, which notice reflects approval by the agency of manufacture, use or sale for human administration. Instructions can also be provided as a fixed, fully detachable, or partially detachable label that is associated with one or more containers in the kit. The instructions associated with the kit can provide directions for preparing the pharmaceutical or veterinary composition for administration and/or instructions for administration of the pharmaceutical or veterinary composition to a subject in need thereof.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

EXAMPLES

The following disclosed embodiments are merely representative of the invention, which may be embodied in various forms. Thus, specific structural and functional details disclosed herein are not to be interpreted as limiting.

Example 1

Calcium Sensitive Inhibition of Amyloid Fibril Formation by NUCB1 and Disaggregation of Amyloid Fibrils by NUCB1

Materials and Methods
Protein Synthesis

Wild type human IAPP (Amylin) was synthesized on a 0.25 mmol scale using 9-fluorenylmethoxycarbonyl (Fmoc) chemistry on an Applied Biosystems 433A Peptide Synthesizer. 5-(4'-Fmoc-aminomethyl-3',5-dimethoxyphenol) valeric acid (PAL-PEG) resin was used to generate an amidated C-terminus. Pseudoproline dipeptide derivatives were employed as described (Abedini and Raleigh, Org Lett. 7, 693-696, 2005). Fmoc-protected pseudoproline (oxazolidine) dipeptide derivatives were purchased from Novabiochem. All other reagents were purchased from Advanced Chemtech, Fischer Scientific, PE Biosystems and Sigma Aldrich (St. Louis, Mo., USA). All solvents used were of A.C.S. grade. Standard Fmoc reaction cycles were used. The first residue added to the resin, pseudoproline dipeptide derivatives, all β-branched residues and all residues following the β-branched residue were double coupled. The peptide was cleaved from the resin using standard trifluoroacetic acid (TFA) methods. The crude peptide was treated with 20% (v/v) acetic acid and lyophilized. The disulfide bond was formed via DMSO induced oxidation of the crude peptide. The oxidized peptide was purified via reverse-phase HPLC using a Vydac C-1 8 preparative column. A two-buffer system utilizing HCl as an ion-pairing agent was used for the purification. Buffer A consisted of 0.045% (v/v) HCl in distilled de-ionized (DDI) water. Buffer B consisted of 80% (v/v) acetonitrile, 20% (v/v) DDI water and 0.045% (v/v) HCl. The purity of the peptide was checked by HPLC and was 99%.

The purified peptide was analyzed by matrix-assisted laser desorption/ionization time-of-flight (MALDI-TOF) mass spectroscopy. The observed molecular weight was 3903.4 Da and the expected molecular weight was 3903.3 Da.

NUCB1 Expression and Purification

The expression and purification of NUCB1 was accomplished by expressing the protein in a recombinant *E. coli* as described in Example 3 (below).

Circular Dichroism Spectroscopy

Wavelength scan: All CD experiments were performed using an Aviv 62A DS CD spectrophotometer. Spectra were recorded over the wavelength range of 1 90-250 nm at 1 nm intervals with an averaging time of 3 s using a 0.1 cm path length cell. Background spectrum was subtracted from each of the collected data sets. Each spectrum obtained was an average of 3 scans.

Thermal unfolding: The unfolding of the protein with temperature was monitored using CD at a wavelength of 222 nm, which is characteristic of an α-helix. The data points were averaged over 30 seconds for every unit increment in temperature. A plot of CD signal versus temperature was fit to equation (1):

$$f(T) = \frac{\alpha_N + \beta_N * T + (\alpha_D + \beta_D * T) * e^{\frac{-\Delta G°_{D-N}(T)}{RT}}}{1 + e^{\frac{-\Delta G°_{D-N}(T)}{RT}}} \quad (1)$$

where, $$\Delta G°_{D-N}(T) = \qquad \text{(equation 2)}$$
$$\Delta H°_{D-N}(T_m) * \left(1 - \frac{T}{T_m}\right) - \Delta C°_p * \left\{(T_m - T) + T * \ln\left(\frac{T}{T_m}\right)\right\}$$

and where f(T) is the signal as a function of temperature, T is the temperature, R is the gas constant, $\alpha_N$ defines the intercept and $\beta_N$ is the slope of the post-transition region of the curve, $\alpha_D$ defines the intercept and $\beta_D$ is the slope of the pre-transition region of the curve, $\Delta G_o$ is the free energy change for the unfolding reaction, $\Delta H°_{D-N}$ is the change in enthalpy for unfolding at the $T_m$ and $\Delta C_p°$ is the change in heat capacity.

Using the above expressions $T_m$, the mid-point transition temperature was estimated, along with the change in enthalpy $\Delta H°_{D-N}$, for the unfolding reaction at that $T_m$.

Analytical Ultracentrifugation

Sedimentation equilibrium studies were carried out at different centrifugation speed values and at different protein concentrations. The samples were run for sufficiently long periods of time to reach equilibrium. The speeds were decided based on the molecular weight of the protein. Under no net transport conditions, the following correlation should be observed between concentration and the radial distance (Van Holde, 1985):

$$C_r = C_{r_0} * e^{\frac{(\sigma * r)}{2}(r^2 - r_o^2)} \quad (3)$$

where, $$\sigma = M(1 - v\rho) * \frac{\omega^2}{RT} \quad (4)$$

and where $C_r$ is the concentration of macrosolute at any radial distance r, $C_{r_0}$ is the concentration of the macrosolute at the reference radial distance r0, v is the partial specific volume, ω is the angular velocity, ρ is the density, R is the gas constant, T is the absolute temperature and M is the molecular mass. The data was analyzed using Optima™ XL-A/XL-I Data Analysis Software (Beckman, 2001).

Amyloid Beta Fibrillization Reaction Protocol

Aβ40 was synthesized on a 0.25 mmol scale using 9-fluorenylmethoxycarbonyl (Fmoc) chemistry on an Applied Biosystems 433A. Valine coupled Wang resin was used to generate a free C-terminus. Pseudoproline dipeptide derivatives were employed as described (Johnson et al. J. Chem. Soc.; Chem. Commun., 369-372., 1993, Wohr et al., J. Am. Chem. Soc., 118, 9218-9227, 1996). Fmoc-protected pseudoproline (oxazolidine) dipeptide derivatives were purchased from Novabiochem. All other reagents were purchased from Advanced Chemtech, Fischer Scientific, PE Biosystems and Sigma Aldrich. All solvents used were of A.C.S. grade. Standard Fmoc reaction cycles were used. The first residue added to the resin, pseudoproline dipeptide derivatives, all β-branched residues and all residues following the β-branched residue were double coupled. The peptide was cleaved from the resin using standard trifluoroacetic acid (TFA) methods. The crude peptide was treated with 20% (v/v) acetic acid and lyophilized. The dry peptide was then dissolved in DMSO and purified via reverse-phase HPLC using a Vydac C-18 preparative column. A two-buffer system utilizing HCl as an ion-pairing agent was used for the purification. Buffer A consisted of 0.045% (v/v) HCl in distilled de-ionized (DDI) water. Buffer B consisted of 80% (v/v) acetonitrile, 20% (v/v) DDI water and 0.045% (v/v) HCl. HCl was used as the ion pairing agent in anticipation of IR studies. The purity of the peptide was checked by HPLC and was 99%. The purified peptide was analyzed by matrix-assisted laser desorption/ionization time-of-flight (MALDI-TOF) mass spectroscopy. The expected molecular mass of Aβ40 is 4329.8 Da. The observed mass was 4.3 kDa. Purified Aβ42 was purchased from Keck facility at Yale University.

The dry peptide was weighed and 0.4-0.5 mg was added to 200 microliters of DDI water. The sample was vortexed briefly for 20 s followed by the addition of 200 microliters of 200 mM Tris buffer at pH 7.4. The solution was vortexed again for 20 s and then centrifuged at 17,200 g for 3.5 min. The supernatant fraction was immediately withdrawn and its concentration was calculated using UV-Vis at 280 nm. This Aβ solution was then used for a fibrillization reaction at the needed concentration in 100 mM Tris buffer at pH 7.4.

The protocol described above was used to set up Aβ fibrillization reactions at a high concentration of 130-150 micromolar. Aliquots were withdrawn at different time points and diluted into 100 micromolar Thio-T (thioflavin-T) in 100 mM Tris buffer at pH 7.4 to give a final Aβ concentration of 15 micromolar. The emission scan of each aliquot was recorded from 462 nm to 600 nm. The intensity of Thio-T fluorescence at 485 nm was then plotted with time to obtain the kinetic curve. The curve was fit using a 5 parameter sigmoidal equation (Equation. 5), $$y(t) = y(t_0) + \frac{a}{\left[1 + e^{\left(\frac{t_0 - t}{b}\right)}\right]^c} \quad (5)$$

where, y(t) is the observed fluorescence at time t, b is the slope of the growth phase, a is the final fluorescence intensity and c is the lag phase.

Aβ is a hydrophobic peptide with a high tendency to self-aggregate. The aggregation can either result in well-ordered β-sheet amyloid fibrils or can also lead to formation of amorphous aggregates. Carefully designed protocols have been developed to allow Aβ aggregation to selectively result in amyloid fibrils. These homogenous fibrils are a necessity for structural studies. The protocol outlined here was initially used for formation of Aβ42 fibrils starting at monomer concentration of 64 micromolar. The progress of the reaction was monitored through TEM (transmission electron microscopy) images. In 5 hours small protofilaments were seen all over the TEM sample grid. In 12 hours the images showed the presence of long fibrils as well as protofibrils. However, only well resolved fibrils were present in the 24 hour images. Aliquots at time points after 24 hours did not show any further change in the formation of fibrils. The protocol was further tested on lower concentration of Aβ42. TEM confirmed that even at 32 micromolar concentration, highly resolved fibrils were formed within 24 hours.

The protocol was also applied on Aβ40 to check for fibril formation. TEM images showed extensive fibrils being formed in 24 hours. The kinetics of Aβ40 fibrillization was measured using thioflavin-T binding assay. The kinetic curve reaches the plateau indicating completion of aggregation within 24 hours of initiation. This was much faster as compared to 12-18 days reported for Aβ40 fibrillization (2001, 2007). The protocol was found to be applicable to both Aβ40 and Aβ42 fibrillization. The thioflavin-T kinetic curve for Aβ42 shows the fibrillization was complete within 16 hours. All TEM images collected showed only fibrillar or pre-fibrillar species. There were no amorphous aggregates to disrupt the homogeneity of the formed fibrils.

Figure 14:
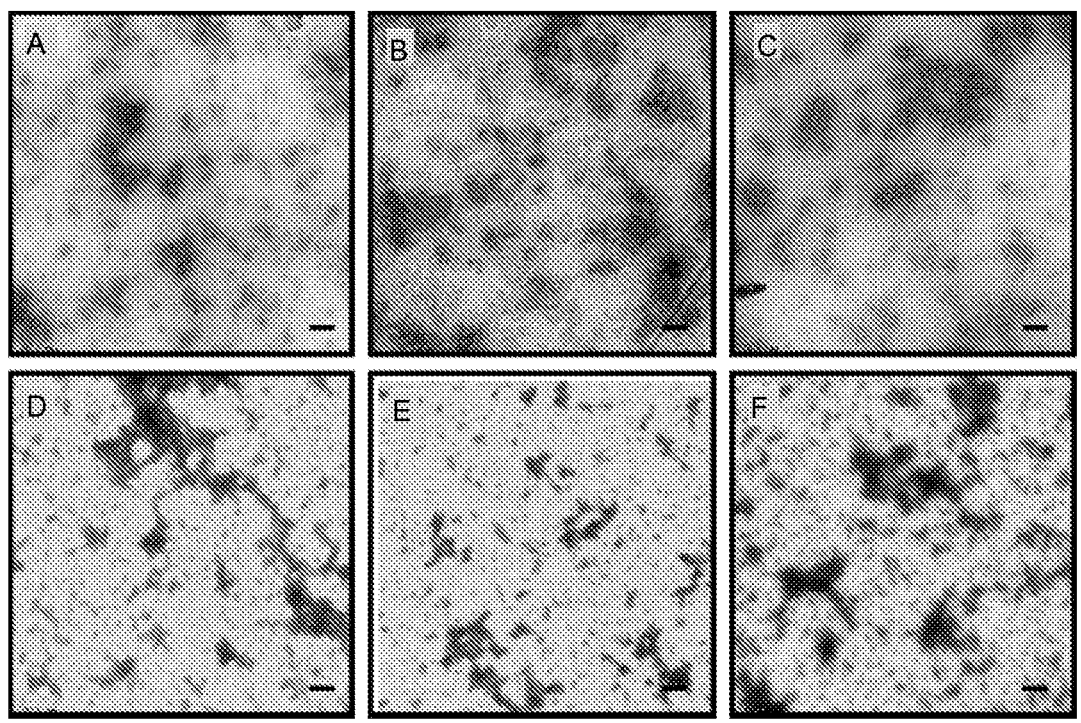
FIG. 14. Inhibition of fibril formation by Aβ42 in presence of sNUCBI(tetramutant) with 1 mM calcium in 100 mM Tris at pH 7.5. Aβ42 peptide was incubated with sNUCBI(tetramutant) and samples were withdrawn for TEM analysis after [A-C] 7 hrs and [D-F] 24 hrs. Scale bar in the images represents 200 nm. sNUCBI(tetramutant) is NUCB1 Δ1-31; D253K, E264A, D305K, E316A (SEQ ID NO:6).
Figure 15:
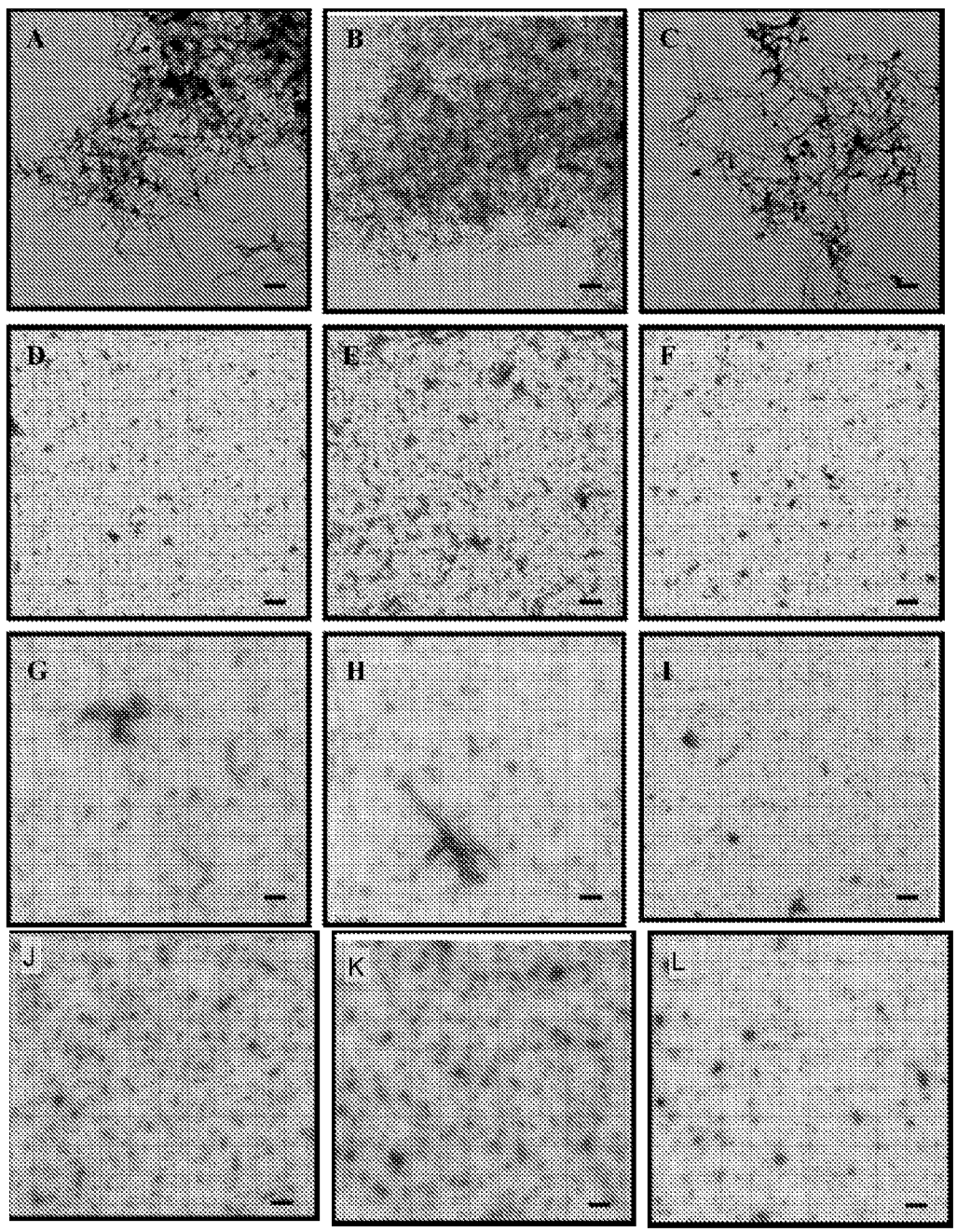
FIG. 15. Disaggregation of Amylin fibrils by Ca2+ free sNUCBI(tetramutant) at stoichiometric ratio to Amylin in 20 mM Tris at pH 7.5. [A-C] Amylin fibrils, [D-F] Disaggregation for 5 mins, [G-I] Disaggregation for 30 mins and [J-L] Disaggregation for 45 mins. Scale bar in the images represents 200 nm. sNUCBI(tetramutant) is NUCB1 Δ1-31; D253K, E264A, D305K, E316A (SEQ ID NO:6).
Figure 16:
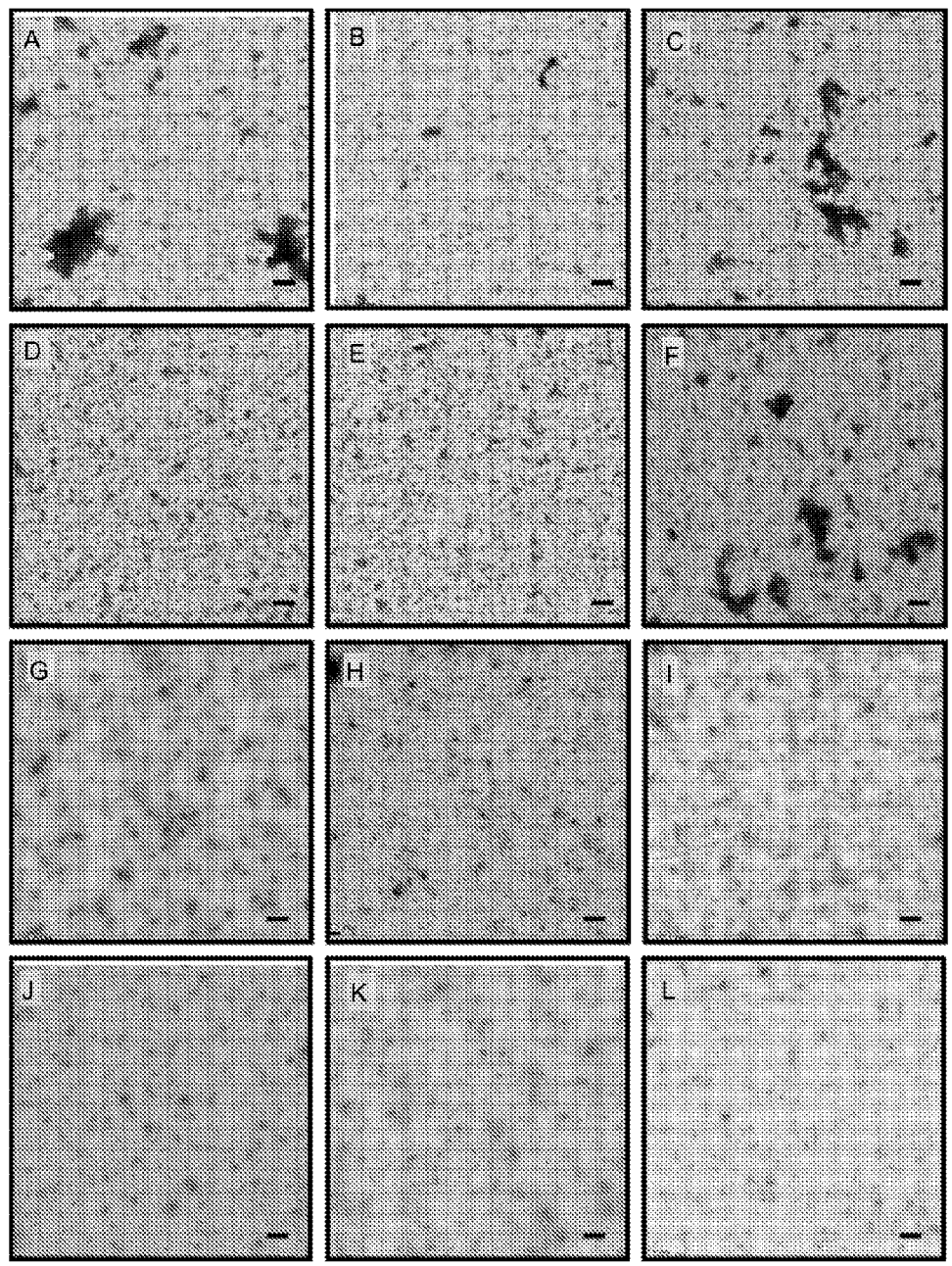
FIG. 16. Disaggregation of Amylin fibrils by sNUCBI (tetramutant) pre-incubated with calcium and then added at stoichiometric ratio to Amylin fibrils in 20 mM Tris at pH 7.5. [A-C] Disaggregation in presence of 200 μM Ca2+ for 15 mins and disaggregation in the presence of 3 mM Ca2+ for 5 mins [D-F], 15 mins [G-I] and 30 mins [J-L] respectively.

We examined the effect of omitting steps in the protocol. Aβ42 fibrillization was performed according to the aforementioned protocol but the centrifugation step was omitted. Aliquots were withdrawn at different time intervals and analyzed through TEM. The fibrils were formed within 24 hours but the images showed presence of both amorphous and fibrillar aggregates (FIGS. 14-16). As the fibrillization was allowed to proceed further, amorphous aggregates and fibrillar aggregates continued to co-exist. Hence, the centrifugation step precipitated the amorphous aggregates allowing the soluble Aβ to form amyloid fibrils. The initial agitation of the solution through vortexing accelerated the nucleation process there by shortening the lag phase. The oligomers formed were small enough to escape precipitation during the centrifugation step. These oligomers then proceeded through a shorter lag phase followed by a rapid growth phase of amyloidogenesis.

Transmission Electron Microscopy

TEM was performed at the Microscopy imaging center at Rockefeller University in New York. Samples were prepared by placing 15 ml of solution onto formvar coated 300 mesh copper grids and counterstained with 2% aqueous uranyl acetate. Samples were viewed with a FEI Tecnai 12 BioTwinG2 transmission electron microscope (FEI, Inc., Hillsboro, Oreg., USA) at 80 kV. Digital images were acquired with an AMT XR-60 CCD Digital Camera System and compiled using the software ImageJ (available on the world wide web at http://rsb.info.nih.gov/ij/).

MTT Assay 7000 to 9000 undifferentiated PC12 cells were plated in each well per 100 µl of culture medium. Cells were grown for an additional 12-16 hrs at 37 degrees C. in an incubator with 5% $CO_2$ supply. Samples to be tested for toxicity were added to the cells at a concentration of 10 µM/well and the cells were incubated for an additional 4 hours. After 4 hours, 10 µl of the MTT stock solution was added to the cells, which were incubated for another 4-6 hours. After this, the media was withdrawn and 200 µl of DMSO was added to each well to dissolve the reduced MTT (formazan) crystals. Spectrophotometric measurement of the absorbance at 570 nm was done for each well and cell viability was calculated based on the measured absorbance with respect to the vehicle absorbance.

Right Angle Light Scattering Experiment

Amylin aggregation and formation of amyloid fibrils was monitored by right angle light scattering on a Jobin Yvon Horiba fluorescence spectrophotometer using an excitation and emission wavelength of 500 nm. The samples were prepared in 20 mM Tris at pH 7.4 and light scattering was monitored as a function of time.

Results

Figure 2:
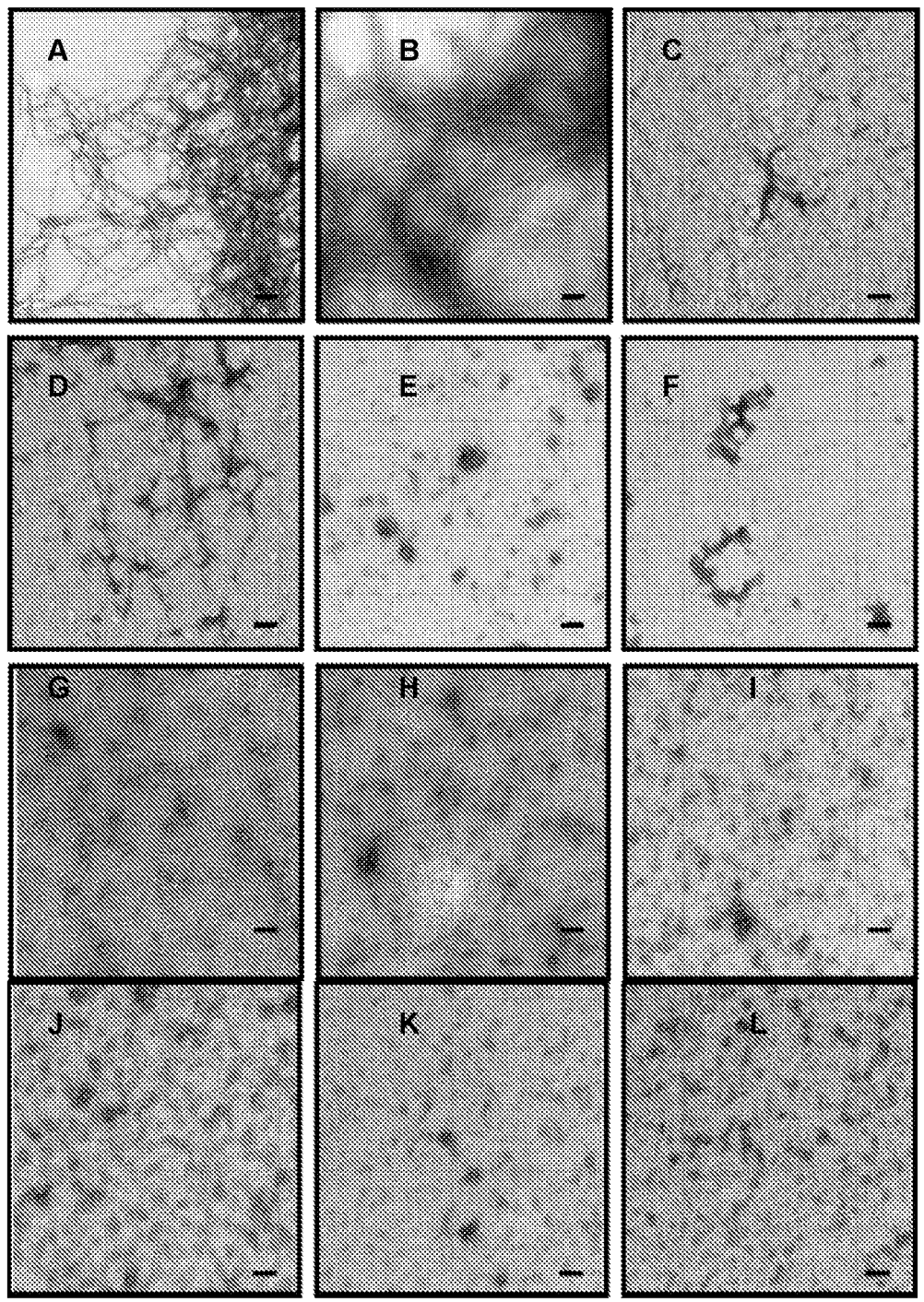
FIG. 2. Disaggregation of Amylin fibrils by calcium free NUCB1. Amylin fibrils (panel A-B) were incubated with Ca2+ free NUCB1 in a 1:1 stoichiometric ratio at 25 degrees C. and 20 mM Tris pH 7.4. Samples were withdrawn at different time points to monitor disaggregation. Panel C-D (t=1 min), panel E-F (t=2 min), panel G-H (t=2 min 37 sec), panel I-J (t=8 min) and panel K-L (t=80). Scale bar in the images represents 200 nm. NUCB1 is SEQ ID NO:3 (NUCB1 with a deletion of residues 1-31).
Figure 3:
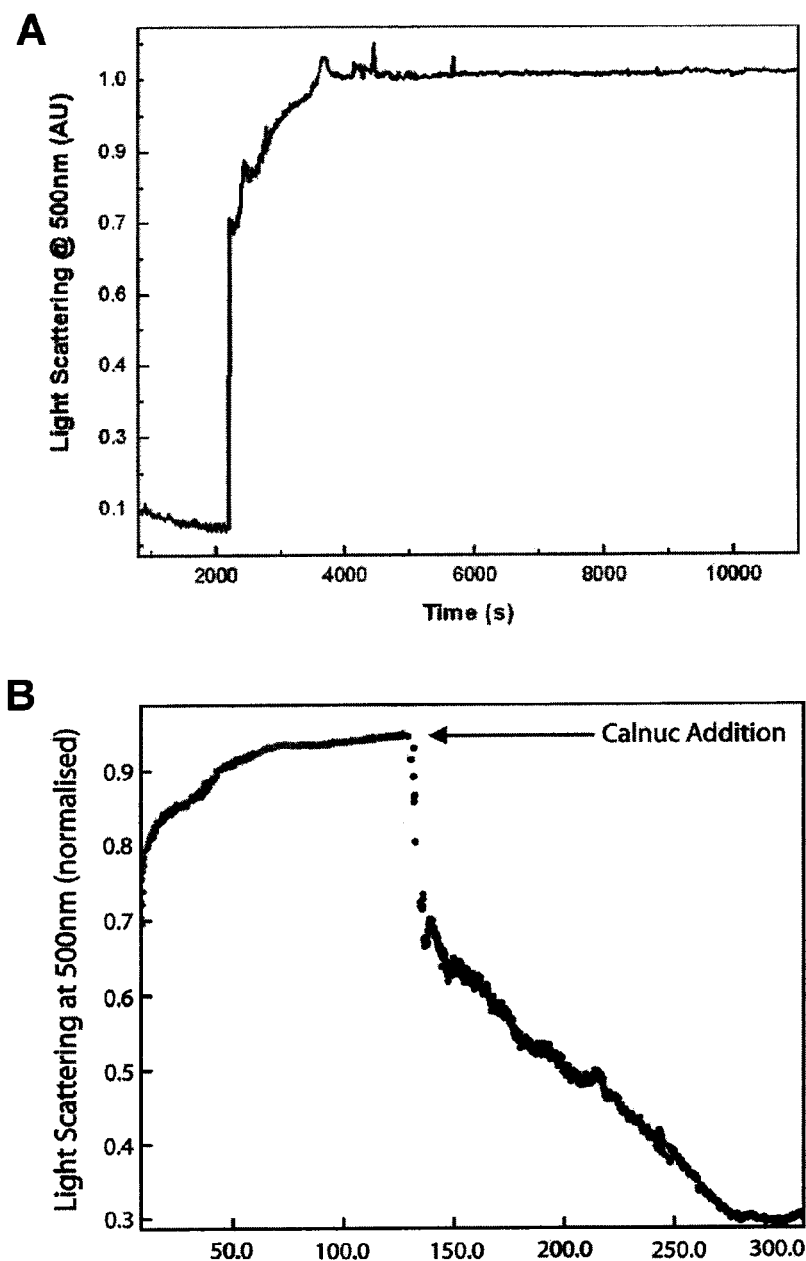
FIG. 3A, B. Right Angle Light scattering shows (A) aggregation of amylin peptide and (B) disaggregation of amylin fibrils once NUCB1 is injected into a reaction volume containing amylin fibrils. The vertical scale is individual normalized on each plot. Thus absolute intensities are not comparable in different panels. NUCB1 is SEQ ID NO:3 (NUCB1 with a deletion of residues 1-31).
Figure 4:
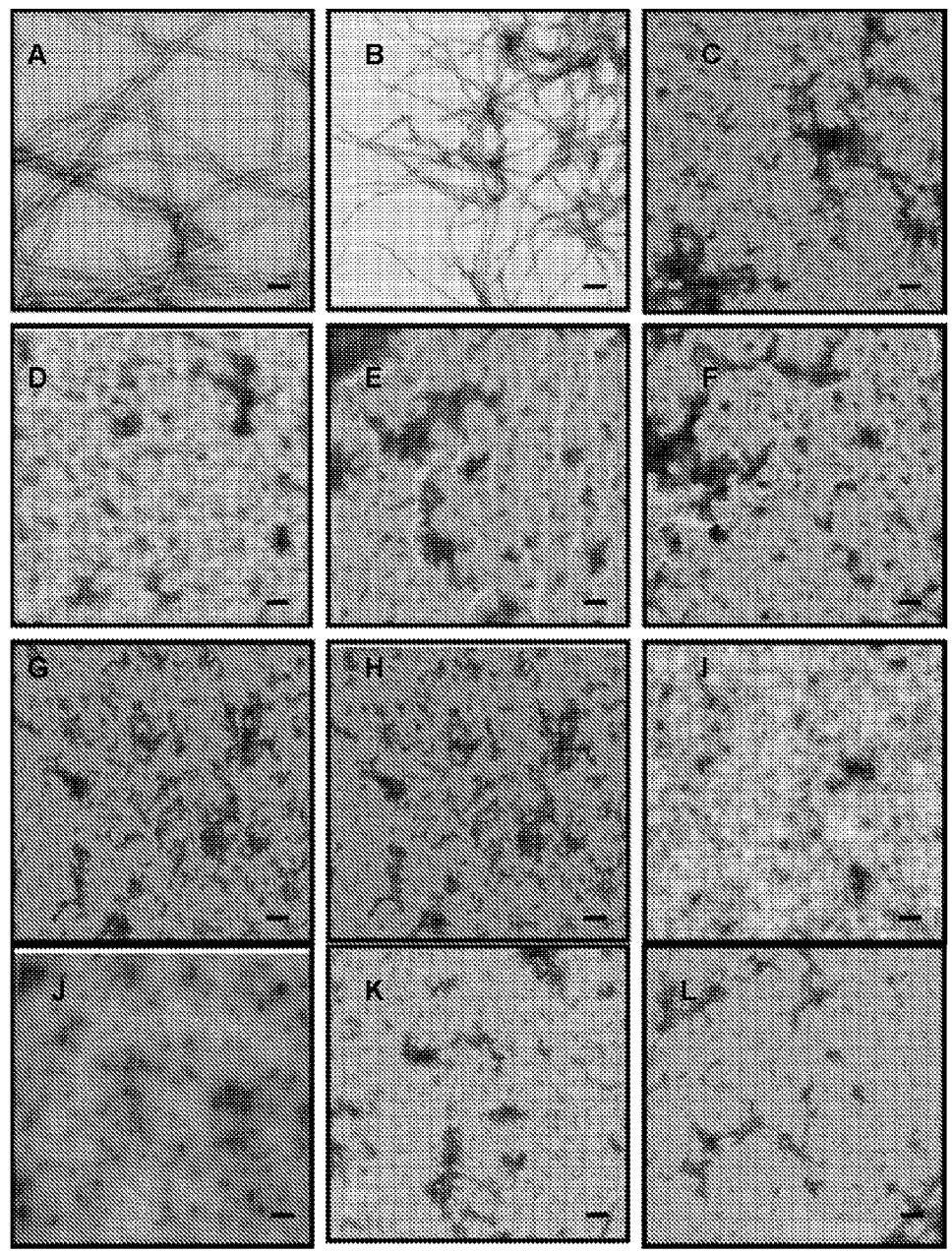
FIG. 4. Disaggregation of Aβ42 fibrils by NUCB1 in the absence of calcium. Aβ42 fibrils (panel A-B) were incubated with Ca2+ free NUCB1 in a 1:1 stoichiometric ratio in 100 mM Tris at pH 7.5 and 25 degrees C. and samples were withdrawn at different time points to monitor disaggregation. Panel C-D (t=5 min), panel E-F (t=15 min), panel G-H (t=30 min), panel I-J (t=1 hr 30 min) and panel K-L (t=20 hr). Scale bar in the images represents 200 nm except for image A where the scale bar represents 100 nm. NUCB1 is SEQ ID NO:3 (NUCB1 with a deletion of residues 1-31).

Amylin in aqueous solution readily aggregates to form extensive β-sheet fibrils. These fibrillar masses show characteristic β-sheet structure by CD and criss-cross long fibrils, which are spread all over the grid in TEM images (FIG. 2). The fibrils once formed are stable with no trace of disaggregation over several months and show strong resistance to any dilution conditions. However, incubation of these fibrillar deposits with $Ca^{2+}$ free NUCB1 triggered complete disassociation of fibrils. Aliquots of the reaction mixture analyzed through TEM showed gradual dissolution of the fibrils into species that lacked fibrillar morphology (FIG. 2). No reappearance of fibrillization was observed even after hours of incubation. Amylin aggregation monitored by light scattering generally shows a characteristic sigmoidal growth curve (FIG. 3A). However when $Ca^{2+}$ free NUCB1 was added after completion of the fibril formation, the light scattering intensity gradually decreased reaching values corresponding to the species present at the start of the reaction (FIG. 3B). The disaggregation of fibrils by NUCB1 was reversed when 5 mM $Ca^{2+}$ was added to the disaggregation reaction. Binding of $Ca^{2+}$ to NUCB1 seemed to mask the ability of NUCB1 to interact with Amylin fibrils and initiate their disaggregation. The disaggregation experiments conducted with $Ca^{2+}$ bound NUCB1 showed fibrils under TEM imaging.

In a similar set of experiments, $Ca^{2+}$ free NUCB1 when incubated with Amylin in a 1:1 ratio showed a remarkable ability to inhibit aggregation. TEM images of the samples withdrawn from the reaction mixture at various time points showed no signs of fibrils. However, a control experiment of Amylin alone in 20 mM Tris at pH 7.4 showed extensive fibrillization with time. Right angle light scattering measurement of the kinetics of Amylin aggregation in the presence of $Ca^{2+}$ free NUCB1 showed no enhancement in the particle size over hours of incubation. The inhibition of Amylin aggregation by NUCB1 was also $Ca^{2+}$ sensitive. Addition of 5 mM $Ca^{2+}$ to the inhibition reaction triggered fibril formation as assessed by TEM.

NUCB1 is a 461 amino acid protein, which is about 12 times the size of Amylin (Petersson et al. Bone, 34, 949-60, 2004). The presence of such large protein molecules in solution might impede the association of Amylin monomers. In order to test the specificity of NUCB1 in inhibiting aggregation and disaggregating fibrils, control experiments were done with bovine serum albumin (BSA). Incubation of Amylin with BSA in stoichiometric ratio of 1:5 did not inhibit the amyloid formation and extensive fibrillar deposits could be seen spread all over the TEM grid through TEM. Hence, the inhibition and disaggregation ability was indeed a functional activity of $Ca^{2+}$ free NUCB1. The inhibition was found to be dependent on the concentration of NUCB1. $Ca^{2+}$ free NUCB1 when present in equimolar amount with Amylin was very effective in keeping Amylin soluble in solution. As the ratio of NUCB1 was decreased to one-third with respect to Amylin, the inhibition was still effective. No significant fibrillization was seen until the ratio was reduced to ⅕th of NUCB1 in comparison to Amylin. However, as the concentration of $Ca^{2+}$ free NUCB1 was decreased further, fibrils were observed. The extent of fibril formation was thus correlated to the molar ratio of NUCB1 and Amylin in the reaction mixture.

Aggregation of Amylin involves an initial lag phase, which is associated with the formation of a nucleus. This nucleation phase is followed by the growth phase where monomers/oligomers add on to the nucleus converting the protofibrillar species into mature fibrils (Merlini and Bellotti, N. Engl. J. Med. 349, 583-596, 2003). Inhibitors of amyloidogenesis, known to date, either prolong the lag phase or slow down the growth phase. To understand the inhibition of amyloid by NUCB1, $Ca^{2+}$ free NUCB1 was added at different time points of the Amylin fibril formation reaction in stoichiometric ratio of 1:1. NUCB1 when added to Amylin at the start of the reaction (t=0) resulted in complete inhibition of fibril formation (FIG. 2). In the second reaction, Amylin oligomerization was allowed to proceed for 2 min into the reaction after which equimolar amount of NUCB1 was added. TEM images showed complete inhibition of fibril formation. In the third reaction, NUCB1 was added after the nucleation phase of Amylin aggregation was complete (t=7 min). TEM analysis convincingly showed that $Ca^{2+}$ free NUCB1 was able to inhibit fibrillization even after nucleation of Amylin. In the fourth experiment, the fibrillization reaction was allowed to proceed to the growth phase and NUCB1 was added during the elongation phase (t=1 5 min). The samples were withdrawn 60 min after the addition of NUCB1 and TEM analysis showed inhibition of fibrillization. This summarizes and supports the observation that $Ca^{2+}$ free NUCB1 can inhibit the aggregation of Amylin at any stage during the fibrillization reaction. This result is important because physiologically Amylin could be present in a wide range of forms varying from monomers to oligomers to fibrils. The results show that NUCB1 can interact with monomers, oligomers as well as protofibrils and prevent their progression to fibril formation.

The next aim was to test the generality of this function of NUCB1 on other amyloidogenic proteins. The pathogenesis in Alzheimer's disease has been shown to be strongly correlated with the aggregation of Aβ peptide (Loo et al. Proc. Natl.

Figure 5:
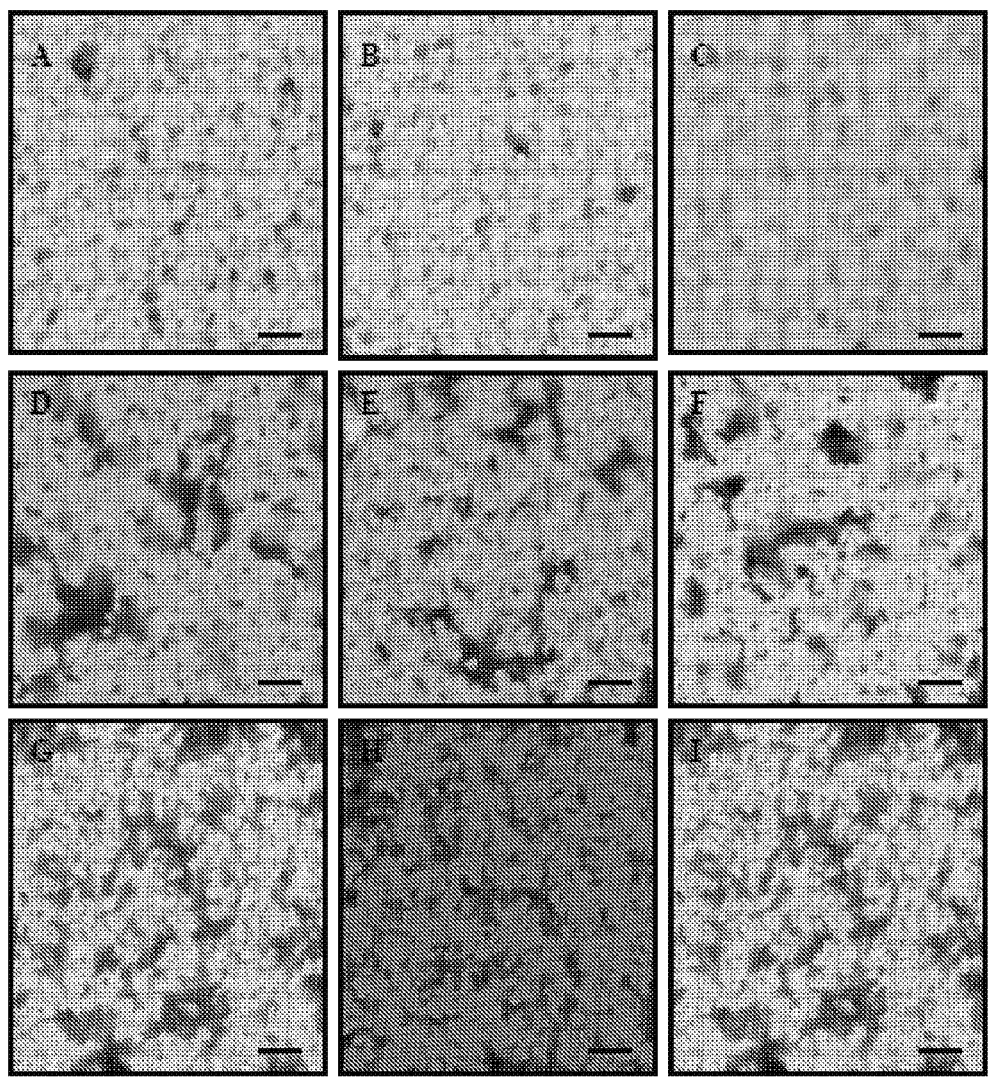
FIG. 5. Inhibition of Aβ42 fibril formation by calcium free NUCB1. Aβ42 peptide was incubated with Ca2+ free NUCB1 in a 1:1 stoichiometric ratio in 20 mM Tris at pH 7.5 and 25 degrees C. and samples were withdrawn at different time points. Panel A-C (t=1 hr), panel D-F (t=5 hr) and panel G-I (t=30 hr). Scale bar in the images represents 200 nm. NUCB1 is SEQ ID NO:3 (NUCB1 with a deletion of residues 1-31).

Acad. Sci., 90, 7951-7955, 1993, Howlett et al. Neurodegeneration. 4, 23-32., 1995). Aβ is produced in two different isoforms in the body, namely Aβ40 and Aβ42. Aβ42 has been shown to aggregate much more aggressively than Aβ40 (Glenner and Wong, Biochem. Biophys. Res. Commun., 120, 855-890, 1984). Thus Aβ42 was chosen to test the functional ability of NUCB1. The aggregation of Aβ42 generally takes at least 6 days with constant stirring at room temperature (Teplow, Methods Enzymol., 413, 20-33, 2006). The stability of NUCB1 over this time period in a test tube at room temperature could affect the interpretation of the observed results. Thus, a new protocol was developed to accomplish Aβ42 aggregation within 24 hours (refer to preceding Materials and Methods). Ca2+ free NUCB1 was added in equimolar ratio at the end of fibrillization reaction. TEM images of the samples withdrawn at different time points after the addition of NUCB1 showed complete dissociation of fibrils (FIG. 5). Rigorous analysis of the grid showed no trace of fibrils in any of the samples withdrawn. Similarly, when Ca2+ free NUCB1 was added in stoichiometric ratio at the start of Aβ42 fibrillization reaction, no fibril formation was observed. TEM images of the samples withdrawn from the reaction mixture at various time points showed no progression of fibrillization. Grids showed no fibril formation in any of the samples withdrawn at different time periods. Thus, the ability of Ca2+ free NUCB1 to disaggregate formed fibrils and to inhibit aggregation appears to be general or at least to be applicable to Amylin and Aβ42.

Figure 6:
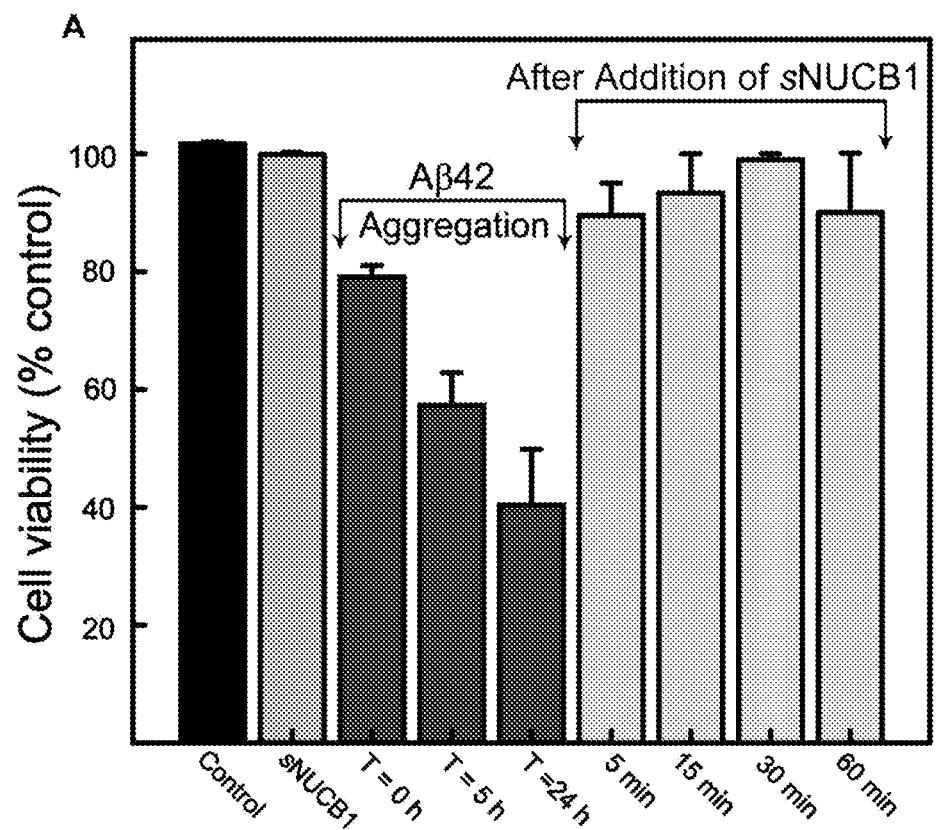
FIG. 6 MTT assay results on PC12 cells showing the cell viability in the presence of Aβ42 monomers, oligomers and fibrils. The cell viability was increased on disaggregation of these fibrils when incubated with Ca2+ free NUCB1 as compared to the control cells. Monomer samples are Aβ peptide taken from initial aggregation reaction in 10 mM Tris at pH 7.5 and 25° C. Oligomer samples were withdrawn at 5 hours and fibrils were withdrawn after 24 hours. All samples were incubated with cells for 4 hours before addition of MTT. NUCB1 is SEQ ID NO:3 (NUCB1 with a deletion of residues 1-31).

The formation of extracellular amyloid deposits by Aβ has been shown to be cytotoxic to neuronal cells. Amyloid aggregation progresses through the formation of various low molecular weight oligomers, which associate to form protofibrils whose 3-dimensional organization further leads to amyloid fibril formation (Kayed et al., Science, 300, 486-489, 2003). Tissue culture based MTT assays provide evidence of the cytotoxicity of both pre-fibrillar and fibrillar species (Lambert et al., Proc. Natl. Acad. Sci., 95, 6448-6453, 1998, Hartley et al., J. Neurosci., 19, 8876-8884, 1999, Hoshi et al., Proc. Natl. Acad. Sci., 100, 6370-6375, 2003). The inhibition and disaggregation of Aβ42 fibrils by Ca2+ free NUCB1 prevented the formation of fibrillar architecture. However, generation of pre-fibrillar species could not be ruled out by TEM analysis. Thus, it was probable that Aβ42 monomers could associate into oligomers in the presence of NUCB1. If oligomeric species is indeed cytotoxic, interaction of NUCB1 with Aβ could enhance cytotoxicity towards neuronal cells. To decipher the nature of species resulting from the disaggregation of Aβ42 fibrils by Ca2+ free NUCB1, MTT assays were conducted with PC12 cells. In the first set of experiments, samples were withdrawn at different time points of Aβ42 fibril formation reaction at t=0, t=5 hr and t=24 hour. Each sample was analyzed using TEM before administration to the cells. The morphology of the samples corresponded to the TEM images of Aβ42 aggregation (FIG. 16). These aliquots were then administered to undifferentiated PC12 cells and their cytotoxicity was assayed through reduction of MIT. The cytotoxicity was found to increase with the progression of fibril formation. In the presence of monomers, neuronal cells showed 80% viability. As the monomers assembled into prefibrillar species, the viability decreased to 60%. The formation of fibrils further reduced the cell viability to 40%. In the next set of experiments, these fibrils were incubated with Ca2+ free NUCB1 for various time periods and the toxicity of the samples withdrawn was assayed through MTT reduction by PC12 cells. The cell viability corresponding to NUCB1 disaggregated species was found to be about 90% after 5 minutes of incubation. The samples withdrawn after 15 to 60 min of NUCB1 incubation increased cell survival rate to at least 90% (FIG. 6). Thus, the results of the cell based assays show promising effects of NUCB1 in disaggregation of neurotoxic fibrils. In each of the cell based experiments, the cells were incubated with the samples for an additional 4 hours before addition of MTT in the 96-well plate. This might cause further aggregation of the samples. However, the rate of aggregation would be slow since the plate was not stirred or agitated. Similarly, PC12 cells were also assayed for cell viability in the presence of Aβ42 monomers. In the presence of Aβ monomers, the cell viability was increased when incubated with Ca2+ free NUCB1 as compared to the control cells that were incubated in the absence of NUCB1.

Figure 1:
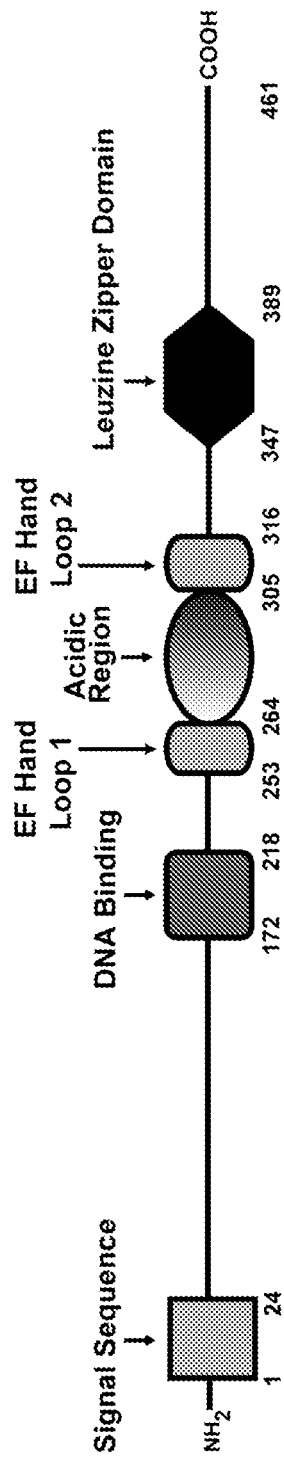
FIG. 1. The domain map of NUCB1 shows the N-terminal signal sequence (residues 1-24), DNA binding region (residues 172-218), 2 EF Hand Loop Domains (residues 253-264 and residues 305-316), an intervening Acidic Region (between residues 264 and 305), and the Leucine Zipper domain (347-389). The numbered residues in the sequence correspond to the residues of the NUCB1 sequence of SEQ ID NO:2 (GenBank Accession No. NP_006175.2).

In all of the above experiments, the role of NUCB1 against amyloidogenesis was effective only in the absence of calcium. Binding of Ca2+ to NUCB1 may thus induce some conformational changes in NUCB1. The resulting structure was unable to prevent the fibril formation or cause the disaggregation of existing fibrils. The domain architecture of NUCB1 shows 2 EF hand regions sandwiched between DNA binding domain and leucine zipper at its C-terminus (Alba and Tjandra, Biochemistry 43(31):10039-49, 2004) (FIG. 1). EF hand regions are known to be a characteristic feature of calcium binding proteins. The formation of an octahedral co-ordination sphere on binding of calcium causes structural rearrangement in the protein (Cates et al., Structure, 7, 1269-1278, 1999). Thus, circular dichroism was employed to monitor any secondary structural rearrangement in NUCB1 on binding to calcium. The comparison of the spectra obtained in the presence and absence of calcium showed no significant structural change in NUCB1 on calcium binding. However, CD data collected at increasing concentrations of NUCB1 showed a smooth structural transition from a α-helix at lower concentrations to β-sheet morphology at concentrations higher than 32 μM. The concentration dependent structural change was found to proceed both in the absence and presence of calcium. A plot of mean residue ellipticity at 222 nm showed an increase with increase in concentration of NUCB1. This data might argue in favor of some concentration dependent association. Furthermore, the thermal unfolding data of NUCB1 showed an increase in Tm of 4 degrees C. on binding of calcium to NUCB1. The folding of NUCB1 was observed to be irreversible both in the absence and presence of calcium in the sense that the CD signal after heating and re cooling differed from the initial value. The increase in stabilization on binding to calcium suggests some structural ordering on Ca2+ binding. However, the rearrangement was not visible through CD spectra. This may not be surprising given the size of the protein and the small number of residues, which would become ordered in the EF hand regions.

The C-terminus of NUCB1 also has a leucine zipper motif (FIG. 1), which are helices with a leucine at every seventh position. This structural motif is a common dimerization domain where dimerization proceeds through hydrophobic interactions among stacked leucine residues (Landschulz et al., Science, 240, 1759-1764, 1988). Analytical Ultra Centrifugation (AUC) studies on NUCB1 revealed that NUCB1 preferentially exists as a dimer irrespective of the presence of calcium. The data analysis for NUCB1 concentrations varying from 50 μM to 150 μM gave a molecular mass corresponding to a dimer. Non-specific association was ruled out by repeating the experiment at several different rotor speeds. CD spectra at 50 μM NUCB1 concentration corresponded to a β-sheet structure. Thus, it might be possible that the structural transition as observed in CD might be related to the dimerization of NUCB1.

AUC experiments were also conducted on a homolog of NUCB1 called NUCB2. NUCB2 is 421 amino acid protein which lacks the 40 residues at the C-terminus found in NUCB1. It shares 65% sequence homology with NUCB1 and has a similar domain architecture to NUCB1 (Oh-I et al. 2006). Molecular weight analysis from AUC data shows that NUCB2 also exists as a dimer both in the presence and absence of calcium ions. This can be explained by the presence of a characteristic leucine zipper motif at its C-terminus similar to NUCB1. NUCB2 when incubated with Amylin monomers in a 1:1 ratio during the amyloid formation reaction was efficient in inhibiting fibrillization. However, Amylin fibrils when incubated with NUCB2 showed no signs of dissociation. The inhibition of amyloidogenesis by NUCB2 like NUCB1 was also calcium sensitive. Thus, NUCB2 was effective in inhibiting fibril formation but could not disaggregate fibrils. It is thus possible that either the absence of the C-terminal region, the absence of homology to the N-terminus of NUCB1, or a combination of those factors could result in the absence of fibrillar disaggregation activity observed for NUCB2.

Amylin fibril disassociation experiments were also conducted on a C-terminal deletion mutant of NUCB1 where residues 333-461 of the C-terminus of NUCB1 (SEQ ID NO:2) were removed. This C-terminal deletion mutant was effective at disaggregating Amylin fibrils but did not inhibit aggregation of Amylin when added in 1:1 stoichiometry at t=0.

Example 2

Inhibition of Amyloid Fibril Formation and Disaggregation of Amyloid Fibrils by a NUCB1 Protein Variant in the Presence of Calcium Materials and Methods
Protein Synthesis and Purification
Wild type human IAPP (Amylin) was synthesized on a 0.25 mmol scale using 9-fluorenylmethoxycarbonyl (Fmoc) chemistry on an Applied Biosystems 433A Peptide Synthesizer. 5-(4'-Fmoc-aminomethyl-3',5-dimethoxyphenol) valeric acid (PAL-PEG) resin was used to generate an amidated C-terminus. Pseudoproline dipeptide derivatives were employed as described above. Fmoc-protected pseudoproline (oxazolidine) dipeptide derivatives were purchased from Novabiochem. All other reagents were purchased from Advanced Chemtech, Fischer Scientific, PE Biosystems and Sigma. All solvents used were of A.C.S. grade. Standard Fmoc reaction cycles were used. The first residue added to the resin, pseudoproline dipeptide derivatives, all n-branched residues and all residues following the β-branched residue were double coupled. The peptide was cleaved from the resin using standard trifluoroacetic acid (TFA) methods. The crude peptide was treated with 20% (v/v) acetic acid and lyophilized. The disulfide bond was formed via DMSO induced oxidation of the crude peptide as described. The oxidized peptide was purified via reverse-phase HPLC using a Vydac C-18 preparative column. A two-buffer system utilizing HCl as an ion-pairing agent was used for the purification. Buffer A consisted of 0.045% (v/v) HCl in distilled de-ionized (DDI) water. Buffer B consisted of 80% (v/v) acetonitrile, 20% (v/v) DDI water and 0.045% (v/v) HCl. The purity of the peptide was checked by HPLC and was 99%.

The purified peptide was analyzed by matrix-assisted laser desorption/ionization time-of-flight (MALDI-TOF) mass spectroscopy. The observed molecular weight was 3903.4 Da and the expected molecular weight was 3903.3 Da. Synthesized and purified Aβ42 was purchased from Keck facility at Yale University.

sNUCBI(tetramutant) Expression and Purification
The expression and purification of sNUCBI(tetramutant) was accomplished by expression in a recombinant $E.$ $coli$ host as described in Example 3. The yield obtained was approximately 7 mg/L.

Protocol for Fibril formation
The dry peptide was weighed and added to 200 µl of DDI water. The sample was vortexed briefly for 20 s followed by the addition of 200 µL of 200 mM Tris buffer at pH 7.4. The solution was vortexed again for 20 s and then centrifuged at 17,200 g for 3.5 min. The supernatant fraction was immediately withdrawn and its concentration was calculated using UV-Vis. This Aβ solution was then used for a fibrillization reaction at the needed concentration in 100 mM Tris buffer at pH 7.4.

Circular Dichroism Spectroscopy
Wavelength scan: All CD experiments were performed using an Aviv 62A DS CD spectrophotometer. Far-UV CD spectra were recorded at the end of each kinetic run. Spectra were recorded over the wavelength range of 190-250 nm at 1 nm intervals with an averaging time of 3 s using a 0.1 cm path length cell. Background spectrum was subtracted from each of the collected data sets. Each spectrum obtained was an average of 3 scans.

Thermal unfolding: The unfolding of the protein with temperature was monitored using CD spectrophotometer at a wavelength of 222 nm, which is characteristic of an I-helix. The data points were averaged over 30 seconds for every unit increment in temperature. A plot of CD signal versus temperature was fit to equation (1):

$$f(T) = \frac{\alpha_N|\beta_N * T|(\alpha_D | \beta_D * T) * e^{\frac{-\Delta G^o_{D-N}(T)}{RT}}}{1 + e^{\frac{-\Delta G^o_{D-N}(T)}{RT}}} \quad (1)$$

where, $$\Delta G^o_{D-N}(T) = \Delta H^o_{D-N}(T_m) * \left(1 - \frac{T}{T_m}\right) - \Delta C^o_p * \left\{(T_m - T) + T * \ln\left(\frac{T}{T_m}\right)\right\}, \quad (2)$$

f(T) is the signal as a function of temperature, T is the temperature, R is the gas constant, $\alpha_N$ defines the intercept and $\beta_N$ is the slope of the post-transition region of the curve, $\alpha_D$ defines the intercept and $\beta_D$ is the slope of the pre-transition region of the curve, $\Delta G_o$ is the free energy change for the unfolding reaction, $\Delta H^o$ is the change in enthalpy and $\Delta C_p^o$ is the change in heat capacity.

Using the above expressions $T_m$, the mid-point transition temperature was estimated, along with the change in enthalpy $\Delta H^o_{D-N}$, for the unfolding reaction at that $T_m$.

Isothermal Calorimetry
Isothermal calorimetry experiments were performed as described in Example 1.

Transmission Electron Microscopy
TEM was performed at the microscopy imaging center at the State University of New York at Stony Brook. Samples were prepared by placing 15 ul of solution onto formvar coated 300 mesh copper grids and counterstained with 2% aqueous uranyl acetate. Samples were viewed with a FEI Tecnail2 BioTwinG$^2$ transmission electron microscope at 80 kV. Digital images were acquired with an AMT XR-60 CCD Digital Camera System.

MTT Assay

In a 96 well plate, 7000 to 9000 undifferentiated PC12 cells were plated in each well per 100 μl of culture medium. Cells were grown for additional 12-16 hrs at 37 degree C. in an incubator with 5% CO2 supply. Samples to be tested for toxicity were added to the cells at a concentration of 10 μM/well and cells were incubated for additional 4 hours. After 4 hours, 10 μl of the MTT stock was added to the cells and incubated for another 4-6 hours. After this, the media was withdrawn and 200 μl of DMSO was added to each well to dissolve the reduced MTT (formazan) crystals. Spectrophotometric measurement of absorbance at 570 nm was done for each well and cell viability was calculated with respect to the vehicle absorbance.

Results

The EF hand domain is a well-characterized motif for Ca2+ binding consisting of a helix-turn-helix structural motif and is found in a large number of calcium binding proteins. The two helices are linked by a short loop region (around 12 amino acids) and are oriented perpendicular to each other. The binding of Ca2+ ions to this loop involves protein backbone atoms and conserved acidic residues like glutamic acid and aspartic acid. The negatively charged oxygen in these residues form electrostatic interactions with the positively charged Ca2+. The majority of the Ca2+ binding residues (5 out of 12) in the loop show a preference and strong conservance for aspartic acid and glutamic acid. The sixth residue is usually a glycine for conformational reasons. The remaining residues are hydrophobic and stabilize the two helices through hydrophobic interactions. The positioning of the coordinating residues results in a pentagonal bipyramidal configuration for the bound Ca2+ (Branden and Tooze, Introduction to protein structure 2nd ed. Garland Publishing: New York, N.Y., 1999). The loop region in EF hand domain of NUCB1 consists of residues 253-264 for the first EF hand and residues 305-316 for the second EF hand. Our aim was to engineer a NUCB1 protein variant which does not bind to calcium. Sequence alignment of the loop region of NUCB1 with the loop region of 4 EF hands region in Calmodulin (Finn and Forsen, Structure 3, 7-11. 1995) showed that residues 253 and 305 at the start of the loop were well conserved aspartic acids. Similarly residues 264 and 316 were highly conserved glutamic acid (FIG. 7). Construction of a co-ordination sphere of Ca2+ with the acidic residues in the loop region of NUCB1 using Calmodulin as a template showed that the 2 conserved residues in each loop region contributed to 3 ligand sites in the Ca2+ co-ordination sphere. Thus aspartic acid at positions 253 and 305 were each mutated to a lysine and glutamic acid residues at position 264 and 316 were mutated to alanine. The desired DNA construct was made through site-directed mutagenesis experiments. The mutations were confirmed through sequencing and the clone was transformed in BL21(DE3) strain of *E. coli* for protein expression. A protocol similar to the expression and purification of NUCB1 was followed for this NUCB1 protein variant referred to herein as sNUCBI (tetramutant). The yield of sNUCBI(tetramutant) was typically 5 mg/L.

Figure 8:
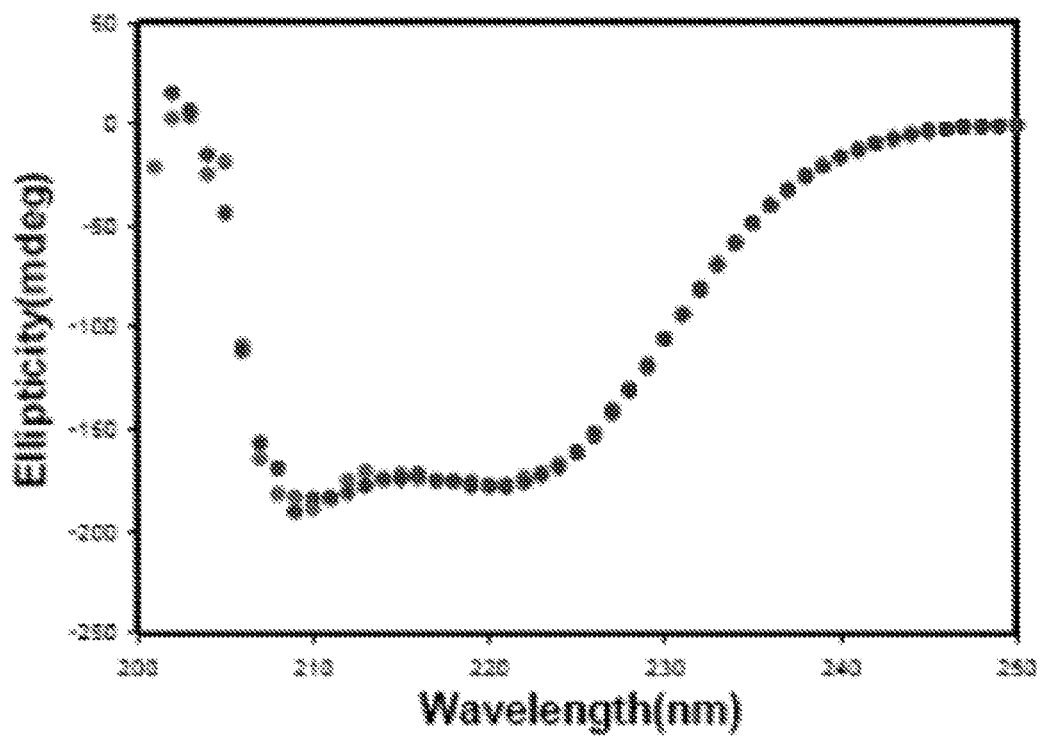
FIG. 8. Circular dichroism of 16 μM sNUCBI(tetramutant) in the absence of Ca2+ (red) and in the presence of 5 mM Ca2+ (blue) at pH 8.0 and 25 degrees C. in a buffer containing 50 mM Tris and 150 mM NaCl. sNUCBI(tetramutant) is NUCB1 Δ1-31; D253K, E264A, D305K, E316A (SEQ ID NO:6).
Figure 9:
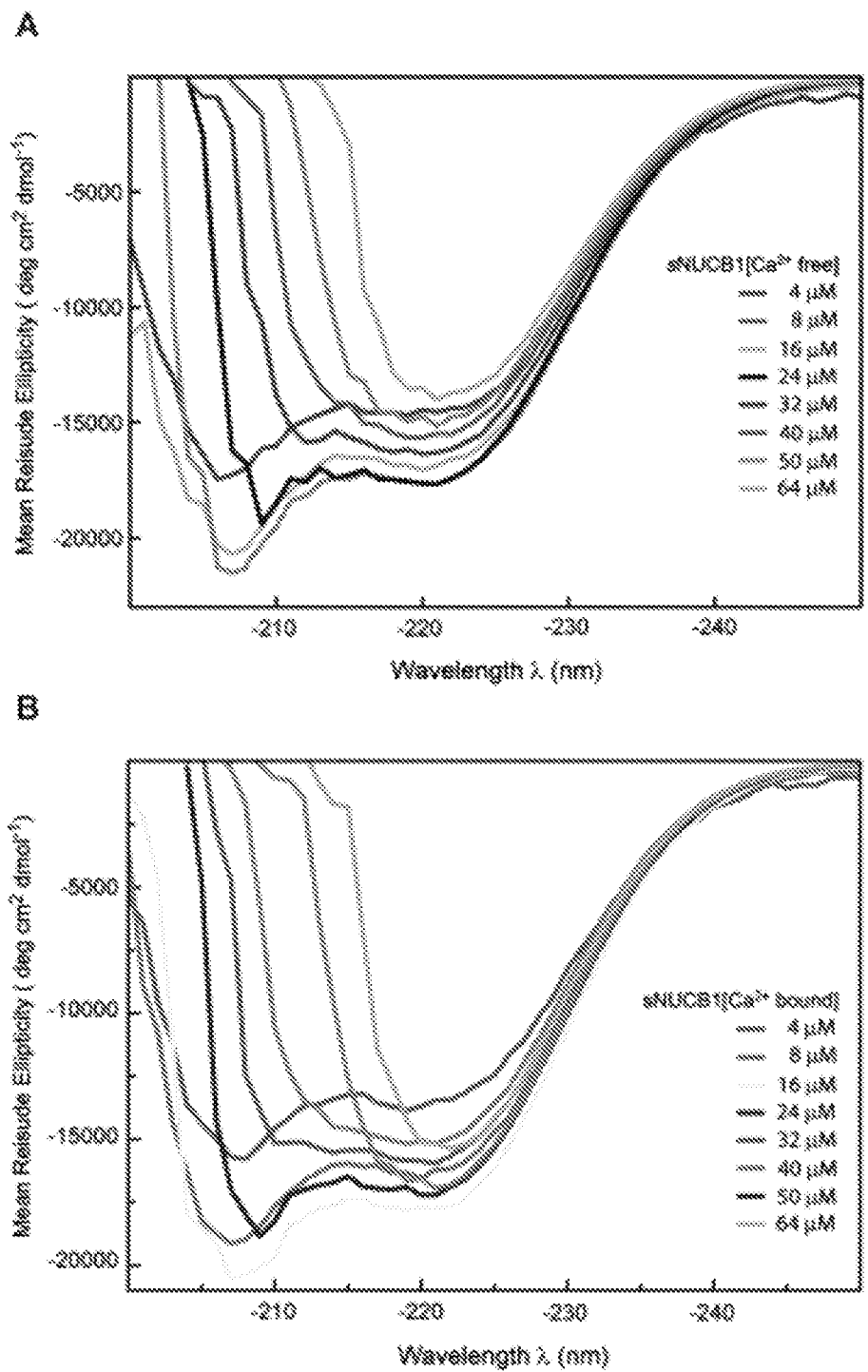
FIG. 9. Circular Dichroism spectroscopy for NUCB1 shows change in the secondary structure with increasing concentration (a) Calcium free sNUCBI(tetramutant) (b) sNUCBI(tetramutant) in the presence of 5 mM Ca2+ at pH 8.0 and 25 degrees C. in a buffer containing 50 mM Tris and 150 mM NaCl. sNUCBI(tetramutant) is NUCB1 Δ1-31; D253K, E264A, D305K, E316A (SEQ ID NO:6).
Figure 10:
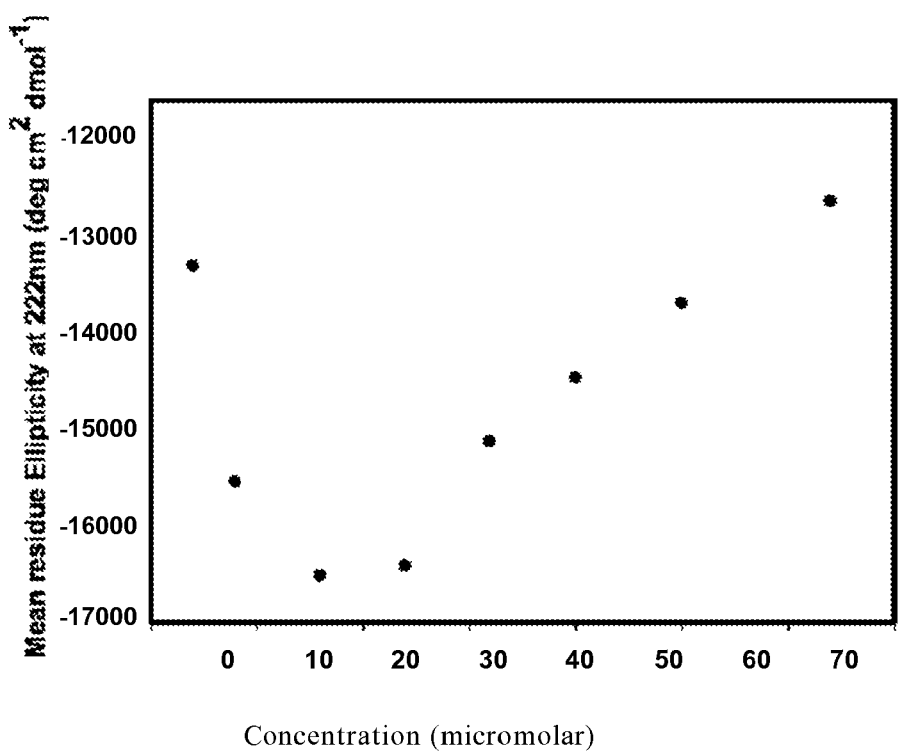
FIG. 10. Plot of mean residue ellipticity at 222 nm for Ca2+ free sNUCBI(tetramutant) in 50 mM Tris and 150 mM NaCl at pH 8.0 and 25 degrees C. sNUCBI(tetramutant) is NUCB1 Δ1-31; D253K, E264A, D305K, E316A (SEQ ID NO:6).
Figure 11:
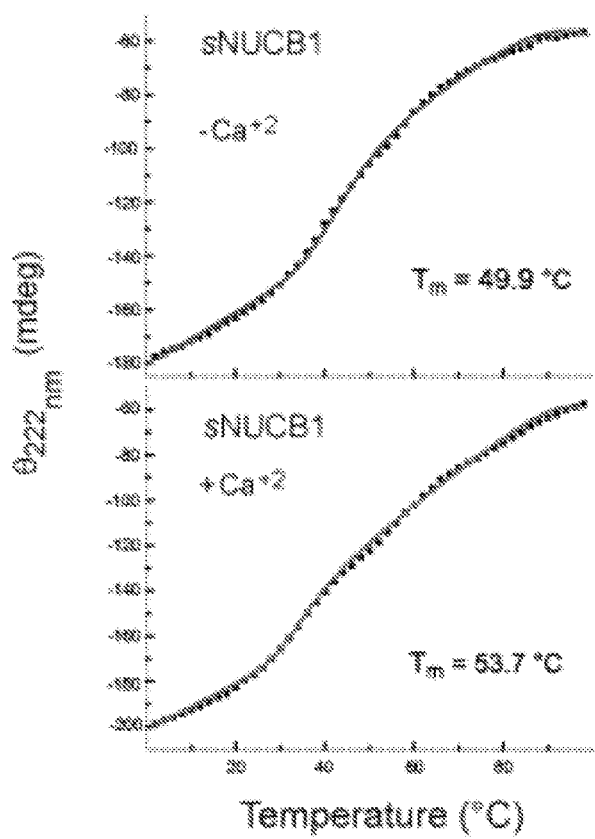
FIG. 11. Thermal unfolding experiment performed by monitoring the change in CD signal at 222 nm for 4 micromolar concentration of A) Ca2+ free sNUCBI(tetramutant) and B) sNUCBI(tetramutant) in the presence of 5 mM Ca2+ with increasing temperature at pH 8.0 in a buffer containing 50 mM Tris and 150 mM NaCl. sNUCBI(tetramutant) is NUCB1 Δ1-31; D253K, E264A, D305K, E316A (SEQ ID NO:6).

The purified sNUCBI(tetramutant) protein variant was first tested for potential calcium binding. Isothermal calorimetric titration of sNUCBI(tetramutant) with an increasing concentration of calcium showed no significant change in enthalpy of the system upon calcium addition. Comparison of the ITC data of sNUCBI(tetramutant) with NUCB1 clearly showed that the mutations have completely abolished the ability of the mutant to bind calcium. The secondary structure analysis of sNUCBI(tetramutant) using circular dichroism showed that the protein was well folded. There was no appreciable change in helicity in the absence or presence of calcium (FIG. 8). The mutant like NUCB1 continued to exhibit a concentration dependent structural transition. At lower concentrations, the CD spectra of sNUCBI(tetramutant) showed a well folded helical structure. However as the concentration was increased from 4 μM to 50 μM, the minima at 208 and 222 nm converged into a single minima at 220 nm corresponding to a β-sheet conformation (FIGS. 9 and 10). This structural transition might be associated with the dimerization through the leucine zipper domain present at the C-terminus of the EF hand region in the protein. The stability of the mutant was comparable to Ca2+ free NUCB1 and was independent of calcium. Thermal unfolding experiments on sNUCBI(tetramutant) revealed no significant gain in transition melting point, Tm, in the presence of calcium (FIG. 11).

Figure 12:
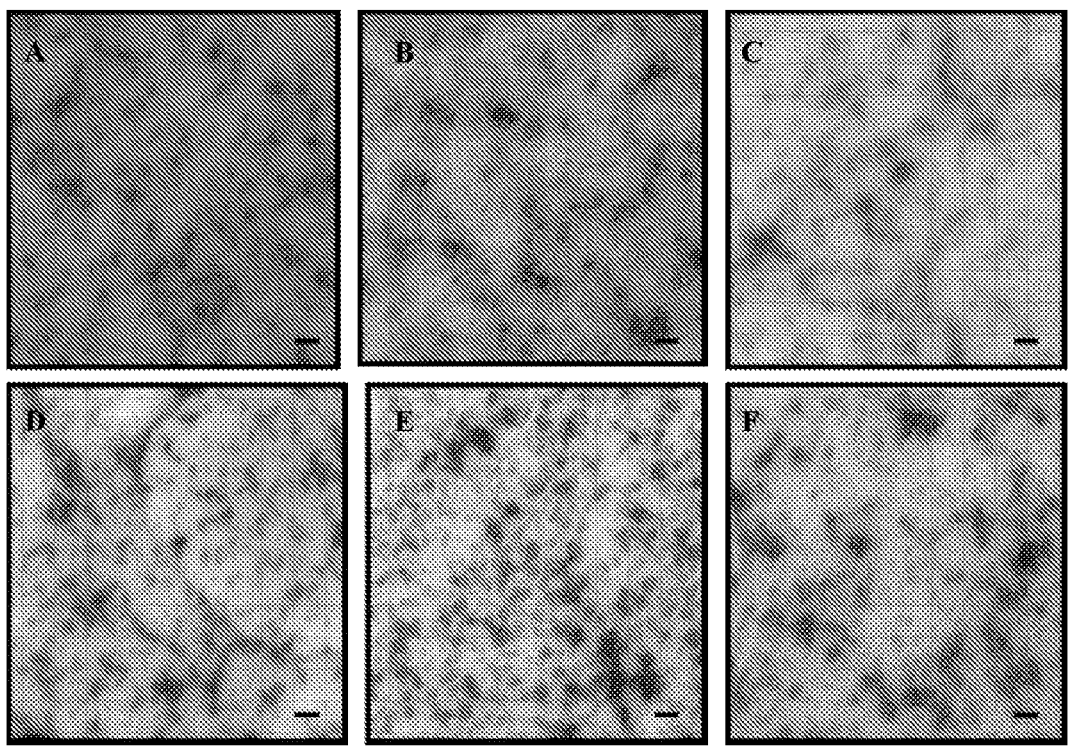
FIG. 12. Inhibition of fibril formation by Amylin in the presence of sNUCBI(tetramutant) without any calcium. Amylin peptide was incubated with sNUCBI(tetramutant) in 20 mM Tris at pH 7.5 and samples were withdrawn for TEM analysis after [A-C] 45 mins and [D-F] 60 mins. Scale bar in the images represents 200 nm. sNUCBI(tetramutant) is NUCB1 Δ1-31; D253K, E264A, D305K, E316A (SEQ ID NO:6).
Figure 13:
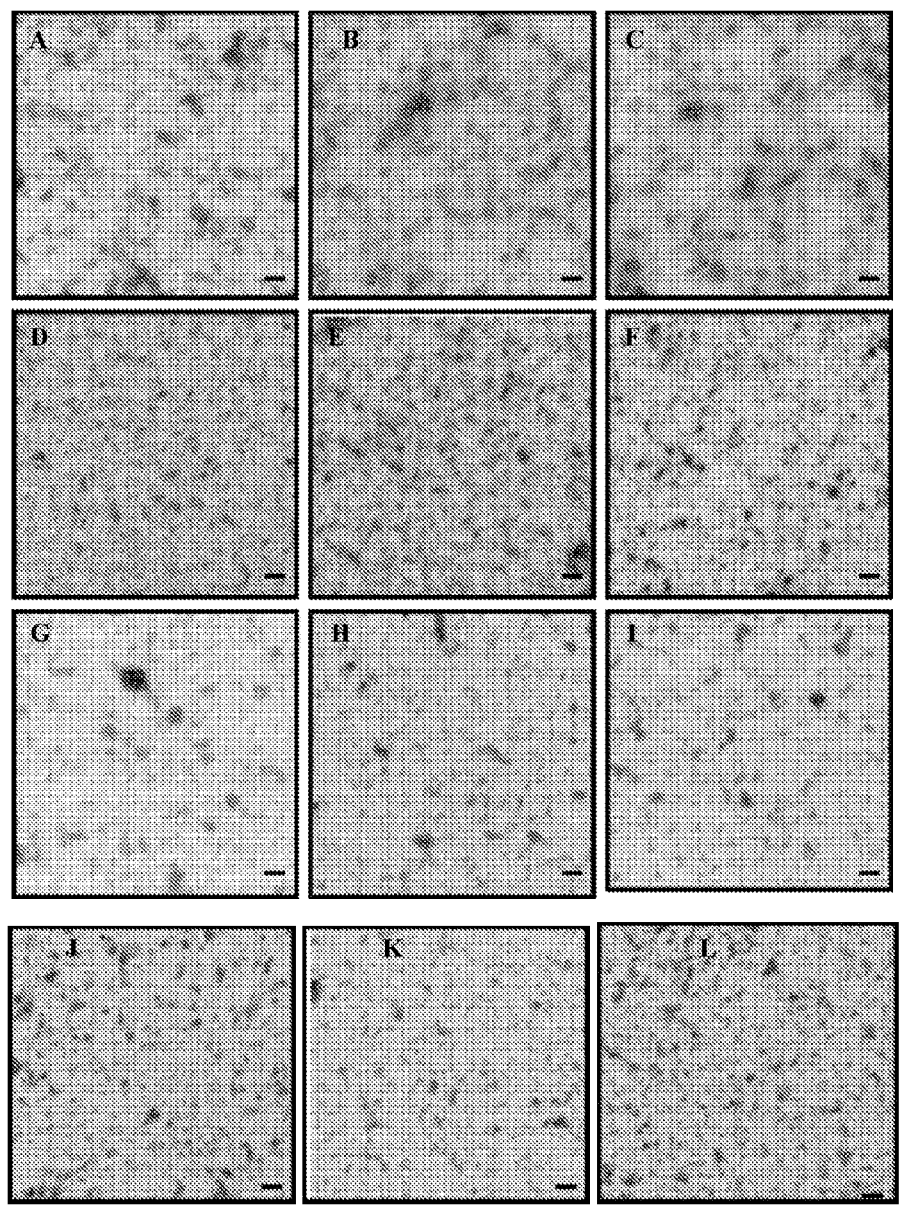
FIG. 13. Inhibition of Amylin fibrillization by 1:1 sNUCBI (tetramutant) pre-incubated with calcium. sNUCBI(tetramutant) was added to Amylin in a 1:1 ratio at 32 μM concentration at t=0 in 20 mM Tris at pH 7.5. [A-C] Sample withdrawn at 60 min with a final Ca2+ concentration of 200 μM. [D-F], [G-I] and [J-L] with Ca2+ concentration of 3 mM and samples withdrawn at 5 min, 30 min and 60 min respectively. Scale bar in the images represents 200 nm. sNUCBI(tetramutant) is NUCB 1Δ1; D253K, E264A, D305K, E316A (SEQ ID NO:6).

The engineered mutant was then tested for its ability to prevent amyloidogenesis. sNUCBI(tetramutant) was incubated with Amylin at pH 7.4 in 1:1 molar ratio at 32 μM concentration and the reaction was monitored through TEM for the formation of fibrils. The samples withdrawn after 45 minutes and 60 minutes of incubation showed no fibrillar species by TEM (FIG. 12). Thus sNUCBI(tetramutant) in the absence of calcium was as effective at inhibiting Amylin aggregation as Ca2+ free NUCB1. A control experiment of Amylin alone in 20 mM Tris at pH 7.4 showed extensive fibrillization in equivalent time periods when assayed by TEM. In the subsequent set of experiments, sNUCBI(tetramutant) was first incubated with calcium and then added to Amylin in 20 mM Tris at pH 7.4 with a final Ca2+ concentration of 200 μM in the reaction mixture. TEM images of the samples withdrawn after 60 min of sNUCBI(tetramutant) with Ca2+ addition showed no signs of fibril formation (FIG. 13). The final concentration of Ca2+ in the reaction mixture was then increased to 3 mM and sNUCBI(tetramutant)-Ca2+ was evaluated for its ability to inhibit Amylin aggregation. Aliquots were withdrawn after different time points at 5 min, 30 min and 60 min and analyzed by TEM (FIG. 13). The images showed no trace of Amylin fibrillization. Thus the engineered sNUCBI(tetramutant) protein can inhibit Amylin fibril formation both in the absence and presence of calcium. The effects on Aβ fibril formation were also tested. sNUCBI (tetramutant) was incubated with Aβ42 (64 micromolar) in 1:1 molar ratio in the presence of 1 mM Ca2+ in the reaction mixture. Samples were withdrawn after 7 hours and 24 hours of incubation. TEM images of the sample grids were clear and devoid of any fibrillar aggregates (FIG. 14). A control experiment of Aβ alone showed extensive fibril formation in 24 hours under the conditions used. Hence, the functional efficacy of NUCB1 at inhibiting amyloid formation was retained by sNUCBI(tetramutant).

NUCB1 also showed a unique ability to disaggregate preformed fibrils in the absence of calcium. Consequently, the ability of sNUCBI(tetramutant) to disaggregate amyloid was examined. sNUCBI(tetramutant) was added to the fibrillar aggregates of Amylin in the absence of calcium. The reaction was monitored via TEM at 5 min, 30 min and 45 min after the addition of sNUCBI(tetramutant). FIG. 15 shows the gradual dissolution of fibrillar aggregates on incubation with equimolar concentration of sNUCBI(tetramutant). sNUCBI(tetramutant) incubated with Ca2+ to the Amylin fibrils was equally effective at the disaggregation of the fibrils. TEM images of the samples with sNUCBI(tetramutant) plus 200 micromolar Ca2+ were indistinguishable from the images of the samples containing 3 mM Ca2+ in the mixture and both were the same as the no calcium experiment. The TEM grids showed complete dissolution of the preformed fibrils on addition of sNUCBI(tetramutant) even in the presence of calcium (FIG. 16). Similar results were observed when Aβ42 fibrils were incubated with sNUCBI(tetramutant) in equimolar ratio. TEM images of the aliquots from the reaction mixture containing sNUCBI(tetramutant) and Aβ42 fibrils show the dissolution of fibrils within 30 min of incubation (FIG. 17). The presence of 1 mM calcium in the reaction mixture did not disrupt the interaction of sNUCBI(tetramutant) with the fibrils. Samples withdrawn at 5 min, 15 min and 30 min after the addition of sNUCBI(tetramutant)-Ca2+ showed the absence of any fibrillar aggregates (FIG. 18). Thus sNUCBI (tetramutant)'s efficacy at disaggregating the fibrillar deposits was comparable to that of wild type NUCB1 and was retained even in the presence of high concentrations of calcium.

The ability of sNUCBI(tetramutant) to inhibit cytotoxicity was tested using PC12 cells. Undifferentiated PC12 cells were exposed to Aβ42 fibrils and to the disaggregated species obtained after incubation with sNUCBI(tetramutant). In the presence of Aβ42 monomers, PC12 cells showed an 80% survival rate. As Aβ42 aggregated to form amyloidogenic oligomers and fibrils, the cell viability decreased to 60% and 40% respectively. Each sample was analyzed using TEM before administering to the cells and were found to contain fibrils. These aliquots were then administered to undifferentiated PC12 cells and their cytotoxicity was assayed through reduction of MTT. However when these cytotoxic fibrils were incubated with sNUCBI(tetramutant), their fibrillar architecture was completely disrupted. The resulting species when tested for their cytotoxicity showed 90-98% cell viability (FIG. 19). Thus there is a direct correlation between the disaggregation of the amyloid deposit by sNUCBI(tetramutant) and cell viability. Similarly, incubation of Aβ42 with sNUCBI(tetramutant) at t=0 inhibited the association of monomers/oligomers into fibrillar species. MTT assay of the inhibition reaction showed no increase in cellular toxicity with time as was observed when no sNUCBI(tetramutant) was added (FIG. 20). Hence the engineered mutant of NUCB1 was able to inhibit and disaggregate fibrils and the resulting species produced by sNUCBI(tetramutant)-mediated disaggregation had no cytotoxic effect in a cell based assay unlike the oligomeric/fibrillar species.

Example 3

Cloning, Heterologous Expression and Purification of Nucleobindin Family (NUCB1 and NUCB2) of Proteins To determine the hydropathy of the proteins, Kyte-Doolitle plots were obtained (FIG. 21). On the basis if hydrophobicity of the proteins, it was noticed that the N-terminus of both proteins had highly hydrophobic residues which may be transmembrane or amphipathic in nature. Hence it was decided to truncate the protein from the N-terminus by deletion mutagenesis (standard quick change mutagenesis, Stratagene, La Jolla, Calif., USA). The N-terminal residues that were deleted from the wild type NUCB1 protein (SEQ ID NO: 2) were residues 1-31 to yield the N-terminally truncated NUCB1 protein (SEQ ID NO:3). The N-terminally truncated NUCB1 protein contains six additional amino acids at its N-terminus that are derived from a protease cleavage site. In other experiments, the N-terminal amino acid residues 2-31 were deleted from the NUCB1 protein (SEQ ID NO:2). However, the deletion of residues 1-31 of NUCB1 provided greater yield than the deletion of residues 2-31 of NUCB1 in the E. coli coli BL21 (DE3) expression system. Residues 1-32 of the NUCB2 protein (SEQ ID NO:4) to yield the N-terminally truncated NUCB2 protein (SEQ ID NO:5) used herein.

Full length NUCB1 with the N-terminus signal sequence was expressed under identical conditions described here, but the expression levels in the soluble cytosolic fractions were negligible. However, it is possible that alternative mammalian cell-based or yeast cell-based expression systems could be used to obtain expression genes encoding full NUCB1 variant proteins. Deletion of EF hand domains of NUCB1 resulted in a viscous supernatant fraction, which was very difficult to filter and no further purification was attempted. The high viscosity could be due to the proper unfolding of the NUCB1 variant lacking the EF hand domains. However, it is possible that alternative mammalian cell-based or yeast cell-based expression systems could be used to obtain expression of NUCB1 variant proteins that lack the EF hand domains.

The clones for NUCB1 (*Homo sapiens*) and NUCB2 (*Mus musculus*) were obtained from the American Type Culture Collection or ATCC (Manassas, Va., USA). NUCB1 (ATCC Accession MGC-8479) was in the vector, pOTB-7 obtained from the small cell carcinoma of the lungs, while NUCB2 (ATCC Accession MGC-5832) in the vector pCMV-SPORT6 was from the mammary gland tumor of a mouse. The nucleotide sequence of NUCB1 is provided as SEQ ID NO: 17 and the amino acid sequence of NUCB1 is SEQ ID NO:2. The nucleotide sequence of NUCB2 is provided as SEQ ID NO:18 and the amino acid sequence of NUCB2 is SEQ ID NO:4. The clones obtained from ATCC were grown in the media as described by the manufacturer. The cDNA were isolated by maxi-prep as described by the vendor (Qiagen, Carlsbad, Calif., USA). The obtained DNAs were then analyzed by nucleotide sequencing. The coding fragments were then amplified using PCR with the 5' end having a Nhe-1 while the 3' having a HindIII restriction site. The 5' oligo for the amplification was 5'CGCCGCTAGCATGCCTCCCTCTGGGC-CCCGAGG (SEQ ID NO:19) and the 3' oligo was CGC-CAAGCTTTCACAGATGCTGGGGCACCTCAACCTCA-GGGA (SEQ ID NO:20) The coding fragments were then inserted into a modified pET-28a(+) vector (Stavropoulos et al, Nature Structural & Molecular Biology 13, 626-632, 2006) at the NheI/HindIII sites using the standard PCR protocol. The pET-28a(+) (Novagen, Madison, Wis., USA) had a Hisx6 purification tag and a PreScission™ protease cleavage site (GE Healthcare, Piscataway, N.J., USA) at the N-terminus of the coding sequence. (FIG. 22). PreScission protease is a genetically engineered fusion protein comprising a human rhinovirus 3C protease and GST (GE Healthcare, Piscataway, N.J., USA). This protease cleaves specifically between the Gln and Gly residues in the human rhinovirus 3C protease cleavage site located between the N-terminal Hisx6 purification tag and the N-terminus of the N-terminally truncated NUCB1 protein to leave six additional amino acids at the N-terminus of the N-terminally truncated NUCB1 protein (SEQ ID NO:6). Large scale recombinant DNA was obtained from TOP-10™ cells (Life Technologies, Carlsbad, Calif. USA). The DNAs isolated by the maxi-prep were sequenced by Genewiz™ (South Plainfield, N.J.) using the vendor's T-7 forward and T-7 term sequencing primers. Only the correct sequences were used for protein expression.

The E. coli BL21(DE3) cell line was used for the expression of the recombinant NUCB1, NUCB1 protein variant, and NUCB2 proteins. A single colony obtained after transformation following the manufacturer's instructions, was grown in 100 mL culture containing kanamycin as the antibiotic marker. This starter culture was then used for large scale expression of the proteins. Typically a dilution of 1:100 (16 mL) is used for the inoculation for 1.6 L of the LB media containing kanamycin. The large scale cultures were grown at 37 degrees Centigrade until the OD reached around 0.5-0.7, when it was induced by 0.4 mM IPTG and subsequently the temperature was brought down to 17 degrees Centigrade. The cultures were grown for about 16-18 hours overnight and the bacterial pellet was obtained by centrifugation of the culture media for 3800 rpm for 25 min. The pellet obtained is suspended in homogenization buffer (Homogenization buffer consisted of 50 mM Tris, pH8.0, 150 mM NaCl, 2 mM beta-mercaptoethanol, 2 mM $CaCl_2$ and protease inhibitors (such as aprotinin, PMSF and EDTA-free protease inhibitor tablets) while the supernatant fraction is discarded. The pellets were then snap frozen in liquid nitrogen until it is ready to use. Usually the pellets are thawed at room temperature and homogenized using the French press (Avestin™, Ottawa, Canada). The homogenate is allowed to undergo about 4-5 passages at 10,000 psi to get the complete lysis of the bacterial cell pellet. The homogenate was then spun at 17,000 rpm (Beckman™ J-17 rotor, Fullerton, Calif., USA) for an hour and the supernatant fraction is collected in a clean glass bottle which has already been cooled in ice. The supernatant fraction is filtered using a 0.45 micron (Nalgene™) filter with a syringe.

Purification of NUCB1, NUCB1 variant, and NUCB2 proteins was effected essentially as follows. The filtered supernatant fraction obtained after filtration is loaded onto a Ni-NTA column (Nickel-nitrilotriaceticacid resin; Qiagen™, Valencia, Calif., USA) using either a 150 mL, 50 mL, or 10 mL Superloop™ loading column (GE Healthcare, Piscataway, N.J., USA) as required by sample volume. The equilibration buffer for the following chromatographic step consisted of 50 mM Tris, pH8.0; 150 mM NaCl, 5 mM $CaCl_2$, 1 mM beta-mercaptoethanol and 10 mM imidazole while the bound proteins were eluted by a higher concentration of imidazole. The elution buffer for the following step consisted of 50 mM Tris pH 8.0; 150 mM NaCl, 5 mM $CaCl_2$, 1 mM beta-mercaptoethanol and 500 mM imidazole. Usually the proteins eluted between 145 mM-200 mM imidazole concentration. In order to deplete the imidazole from the previous step, the eluted protein was either dialyzed with the same buffer as the equilibration buffer lacking imidazole or desalted with a suitable column. When dialysis is carried out, then the PreScission™ protease is added along with the protein. The protease is added after the protein eluate was desalted or has been passed through HiLoad™ Superdex desalting column (GE Healthcare, Piscataway, N.J., USA). In either case, the desalted protein was incubated with the protease for more than 24 hours to get complete or maximum cleavage.

Following the protease cleavage step, the N-terminal Hisx6 tag was removed from the NUCB1, NUCB1 variant, and NUCB2 proteins by a second round of NI-NTA chromatography. The equilibration and elution buffer had the same composition as in the previous NI-NTA chromatography step. Since the level of the expressed protein was high, the protease is unable to cleave all of the fusion protein in the entire collected fractions. In order to separate the uncleaved NUCB1, NUCB1 variant, and NUCB2 fusion proteins from the cleaved NUCB1, NUCB1 variant, and NUCB2 proteins that lack N-terminal Hisx6 tags, the total protein from the protease reaction is loaded on to a 2nd Ni-NTA chromatography column and eluted as described above. The cleaved NUCB1, NUCB1 variant, and NUCB2 proteins that lack N-terminal Hisx6 tags comes out as an eluate in the flow-through fraction while the uncleaved proteins are eluted out with imidazole. The flow through fraction is collected and loaded on to a GSH-Sepharose 4FF column chromatography (GE Healthcare). Since the PreScission™ protease has a N-terminal GST (Glutathione S-transferase) attached, this tag is used for affinity chromatography to separate the NUCB proteins from the PreScission™ protease that is used to remove the Hisx6 tag. Since the PreScission™ protease has the GST tag, this fusion protein remains bound to the GSH-Sepharose 4FF column while the cleaved NUCB1 proteins come out in the flow through. The buffers used in the GSH-Sepharose 4FF column chromatography step were as follows: (i) Equilibration buffer: 50 mM Tris, pH8.0; 150 mM NaCl, and 1 mM beta-mercaptoethanol, while the elution buffer consisted of the same composition as the equilibration buffer except that this buffer had 20 mM reduced glutathione. The eluent from the GSH-sepharose chromatography step is then concentrated by using an Amicon™ filter (Millipore, Bedford, Mass., USDA) having a cutoff of 10 kDa. The protein is concentrated to less than 10 mL and is loaded onto a HiLoad 26/60 Superdex 200 column. The wild type protein elutes out as a major peak while the mutant proteins had multiple peaks. In either case scenario, the protein that was obtained from these fractions were of high purity (>95%) as observed in an SDS page electrophoresis. The sizing column buffer consisted of 50 mM Tris, pH8.0; 150 mM NaCl, 2 mM CaCl2 and 1 mM DTT.

Once the protein has been eluted from the size exclusion chromatography, they are further concentrated to about 1-2 mL. The protein is aliquoted in 40 microliter tubes and flash frozen in liquid nitrogen. The protein concentration was determined by using the extinction coefficient after the sequence has been submitted to the program PROTPARAM described in Gasteiger et al., in Protein Identification and Analysis Tools on the ExPASy Server; (In) John M. Walker (ed): The Proteomics Protocols Handbook, Humana Press (2005). pp. 571-607; and located on the World Wide Web at http://www.expasy.ch). Typically a liter of bacterial host culture yielded about 5-6 mg of purified NUCB1, NUCB1 variant, or NUCB2 protein per liter of the LB broth culture.

Example 4

Peptidase Activity of a NUCB1 Protein Variant and NUCB1 in the Presence of Calcium A NUCB1 protein variant referred to as the NUCB1 tetra-mutant (SEQ ID NO:6) and an NUCB1 control protein (SEQ ID NO:3) were assayed for peptidase activity. In brief, purified NUCB1 protein variant and NUCB1 protein were assayed with the EnzChek™ Protease Assay Kit (Molecular Probes (Life Technologies), Eugene, Oreg., US). Assays were typically performed in a 3 mL quartz cuvette that contained 20 mM Tris, pH 8.0 and 100 micromolar sodium azide. The substrate concentration (BODIPY-Casein, 1 microgram/microliter) as well as the cofactor (Zn2+) were kept constant while varying only the protein concentration (166 nanomolar to 2.5 micromolar). Results of the peptidase assays are provided in FIG. 23 (NUCB1 protein variant of SEQ ID NO:6) and FIG. 24 (NUCB1; SEQ ID NO:3). The NUCB1 assays of FIG. 24 were performed by loading the NUCB1 protein with 80 micromolar Ca2+. All the assays were carried out at 25° C. in a Jobin-Yvon Spex Fluorometer (Edison, N.J., USA) connected to a water bath. The excitation wavelength was 505 nm and the emission wavelength was 513 nm.

Significant peptidase activity was observed in both reactions containing the NUCB1 protein variant (SEQ ID NO:6) and NUCB1 (SEQ ID NO:3).

Example 5

Zinc Binding Activity of a NUCB1 Protein Variant

Zinc binding activity of the NUCB1 tetramutant (NUCB1 Δ1-31; D253K, E264A, D305K, E316A; SEQ ID NO:6) was assayed by a spectral analysis of emissions of the protein at different zinc concentrations. In the assay, the protein was in 20 mM Tris, pH8.0 and the concentration of Zinc varied from 166 micromolar to 2.6 millimolar. The spectral measurement was done on a Jobin-Yvon Spex t3 spectrofluorimeter, while exciting the sample at 295 nm and monitoring the emission from 320 to 400 nm. The spectra was collected at 25 degrees C. Results of the spectral analysis shown in FIG. 25 are consistent with zinc binding to the NUCB1 protein variant.

In this assay, the non-polar fluorescent probe BIS-ANS was used to study the conformational changes in the protein after the addition of Zinc. Bis-ANS is non-fluorescent or weakly fluorescent in polar environment but the fluorescence enhances if this probe moves to a more hydrophobic environment. Typically, this experiment consists of about 200 nanomolar NUCB1 protein variant (NUCB1 tetramutant of SEQ ID NO:6) in 50 mM Tris pH 8.0 buffer with constant concentration of BIS-ANS and titrated against varying concentrations of Zinc as indicated in FIG. 26, Panel A. The excitation was 390 nm while monitoring the emission from 460-600 nm. The overall changes in the BIS-ANS fluorescence on binding to Zinc as well as Ca2+ and Mg2+ is shown in FIG. 26, Panel B.

Tests to determine if purified NUCB-1 (tetramutant) had bound zinc were done by monitoring the conformational change of the protein upon bis-ANS binding in the presence of increasing concentrations of the Zn2+ specific chelator, 1,10-phenanthroline (FIG. 27). Removal of zinc from the protein by this chelator results in the quenching of BIS-ANS fluorescence, indicating that the purified protein had bound zinc. The concentration of the purified protein was 200 nanomolar while the concentration of the chelator (1,10-OP) varied from 0-2.4 millimolar. The fluorescence experiment was done on a Jobin-Yvon T2 Fluorescence spectrometer (Jobin-Yvon Edison, N.J., USA), while exciting at 390 nm and monitoring the spectral changes from 460-600 nm. The data were consistent with zinc binding to the NUCB1 protein variant.

In order to asses the thermodynamic characteristics and binding affinities of the NUCB1 tetramutant for zinc, ITC (Isothermal Titration calorimetry) was used (FIG. 28). The study was done at 25 degrees C. In this experiment, 50 micromolar NUCB1 (Tetramutant) in a buffer containing 50 mM Tris, pH 8.0, 150 mM NaCl and 1 mM TCEP was titrated with Zinc Chloride (molar ratio of 50 to the protein concentration). Based on this experiment it is seen that the protein binds to Zinc both endothermically (low affinity) and exothermically (high affinity). When the plot was fitted for 2 binding sites it gave a Kd of 190 nanomolar for the high affinity zinc binding while a Kd of 5.0 micromolar was seen for the low affinity (endothermic) zinc binding site.

Example 6

Expression of Additional NUCB1 Mutant Proteins in E. coli

The E. coli expression system comprising the T7 expression system described in Example 3. This system essentially comprised an insertion of the mutant NUCB1 sequence into a modified pET-28a(+) vector such that a Hisx6 purification tag and a PreScission™ protease cleavage site were operably linked to the N-terminus of the coding sequence.

Expression of a NUCB1 mutant protein comprising a deletion of residues 1-31 and a deletion of residues 253-264 (i.e. a N-terminal EF hand loop region deletion) of SEQ ID NO:2 in this E. coli based system presented difficulties with the purification of this protein since the N-terminal Hisx6-tag could not be cleaved even with extensive incubation with the PreScission™ protease in the elution buffer.

Expression of a NUCB1 mutant protein comprising a deletion of residues 1-31 and a deletion of residues 305 to 316 (i.e. the C-terminal EF hand loop region deletion) of SEQ ID NO:2 in this E. coli based system presented difficulties with the purification of this protein since the N-terminal Hisx6-tag could not be cleaved even with extensive incubation with the PreScission™ protease in the elution buffer.

Expression of a NUCB1 mutant protein comprising a deletion of residues 1-31, a deletion of residues 253-264 (i.e. a N-terminal EF hand loop region deletion), and a deletion of residues 305 to 316 (i.e. the C-terminal EF hand loop region deletion) of SEQ ID NO:2 in this E. coli based system presented difficulties with the purification of this protein since the N-terminal Hisx6-tag could not be cleaved even with extensive incubation with the PreScission™ protease in the elution buffer.

Expression of a NUCB1 mutant protein comprising a deletion of residues 1-31, a substitution of aspartate 253 with lysine, and a substitution of glutamate 316 with alanine in SEQ ID NO:2 in this E. coli based system presented difficulties with the purification of this protein since the N-terminal Hisx6-tag could not be cleaved with the PreScission™ protease. In a Ca2+ free state the protein that comprised the Hisx6 tag and obtained from E. coli was mixed with amylin in a 1:1 stoichiometric ratio but did not exhibit inhibition of fibril formation.

Expression of a NUCB1 mutant protein comprising a deletion of residues 1-31 and a deletion of residues 333 to 461 of SEQ ID NO:2 in this E. coli based system resulted in expression of a protein that was purified to homogeneity after cleavage of the N-terminal Hisx6-tag. In one experiment, this protein was unable to inhibit the aggregation process of amylin in a 1:1 stoichiometry under calcium free conditions. In one other experiment, this C-terminally truncated NUCB1 mutant protein exhibited amylin fibril disaggregating property under calcium free conditions similar to that observed in wild type NUCB1 protein under calcium free conditions.

Expression of a NUCB1 mutant protein comprising a deletion of residues 1-31 and a deletion of residues 407 to 461 of SEQ ID NO:2 in this E. coli based system resulted in expression of a protein that was purified to homogeneity after cleavage of the N-terminal Hisx6 tag. In one experiment, this protein was able to inhibit the aggregation process of amylin in a 1:1 stoichiometry under calcium free conditions.

Example 7

Inhibition of hIAPP Aggregation by Various NUCB1 Variant Proteins

The following NUCB1 wild type and NUCB1 variant proteins were obtained and tested as described.

sNUCB1 (FIG. 29) was able to inhibit hIAPP aggregation as well as dissociate preformed hIAPP fibrils. The functional capability of sNUCB1 was dependent on the presence of Ca2+ in the reaction vessel as the Ca2+-bound sNUCB1 was ineffective at both inhibiting as well as disaggregation fibrils.

The NUCB1 Tetramutant (NUCB1 Δ1-31; D253K, E264A, D305K, E316A; SEQ ID NO:6; NUCB1 Tetra in FIG. 29) mutant was insensitive to the presence of Ca2+ in the reaction vessel. Each of the conserved glutamic acids and the aspartic acids in the EF hand domains of the two respective EF hands of sNUCB1 were mutated to alanine and lysine, respectively, to completely disrupt the Ca2+ co-ordination sphere thereby abolishing binding of Ca2+ to the protein. Importantly, this protein was effective at inhibiting and disaggregating hIAPP fibrils and the effect was insensitive to the presence of Ca2+ in the reaction mixture (Table 2). Even at high concentrations of Ca2+ the protein was functionally active.

In the sNUCB1(S44C)A protein variant (FIG. 29), cysteine was incorporated into the protein in place of a serine at the 44th position. The protein was purified to homogeneity and used in labeling studies by conjugating the protein to nanogold probe. We then utilized this labeled protein to perform inhibition studies and look for the presence of sNUCB1 (S44C) on the intermediate aggregation species of hIAPP. The sNUCB1(S44C) protein was efficacious in inhibiting fibril formation (Table 2) and TEM analysis of the reaction mixture showed the presence of nanogold density at ends of the intermediate aggregates of hIAPP suggesting the sNUCB1 inhibits the aggregation of these intermediates into mature fibrils by blocking the ends of this intermediate aggregate so that growth is halted.

In the sNUCB1(G408Ter) protein variant (FIG. 29), 54 C-terminal amino acids of NUCB1 are deleted. The wild-type sNUCB1 is a dimer in solution irrespective of the presence of Ca2+ in the solution. In order to investigate the importance of the oligomeric state and to isolate the smallest possible functional unit of sNUCB1 capable to inhibit the aggregation of hIAPP into mature fibrils, sNUCB1(G408Ter) was purified where sNUCB1 was C-terminally truncated. The sNUCB1 (G408Ter) truncation mutant was still effective at inhibiting aggregation of hIAPP into mature fibrils (Table 2). Similar to sNUCB1, the sNUCB1(G408Ter) truncation mutant was unable to inhibit aggregation in the presence of excess amount of Ca2+ in the reaction mixture.

In the eNUCB1 (Q401 Ter) protein variant (FIG. 29), of a further truncation of the C-terminal PolyQ motif (polyglutamine) of sNUCB1 was made and the protein was purified to homogeneity. Interestingly the mutation affected the overall structure of the protein such that the N-terminal His6-tag could no longer be cleaved by using PreScission Protease. Hence an uncleaved protein was purified which was still effective at inhibiting aggregation of hIAPP peptide into mature fibrils in the absence of Ca2+ (Table 2). The ability of the eNUCB1 (Q401 Ter) protein variant to inhibit aggregation of hIAPP in the presence of Ca2+ has not been tested.

In order to investigate the importance of the dimeric state of sNUCB1 on its functional efficacy, a C-terminal truncation mutant sNUCB1(W333Ter) was designed and purified to homogeneity. The protein was still effective at inhibition aggregation of hIAPP peptide into mature fibrils suggesting that dimer might be important but not necessary for the functional efficacy of the protein. Even the monomeric form of the protein is sufficient at inhibiting aggregation in the absence of Ca2+ (Table 2). The ability of sNUCB1(W333Ter) to inhibit aggregation in the presence of Ca2+ needs further investigation.

In the eNUCB1(233-400) protein variant (FIG. 29), both C-terminal and N-terminal truncations were introduced into the expressed protein. The protein was purified as a His6-tag protein whereby the tag could not be cleaved even after extensive incubation with PreScission Protease. The uncleaved protein was purified to homogeneity and similar to above was effective at inhibiting aggregation of the hIAPP peptide into mature fibrils (Table 2). The eNUCB1(233-400) protein variant is thus structurally sufficient to inhibit the aggregation reaction.

sNUCB1 (P240Ter)

A further truncation of the sNUCB1 protein was done whereby the portion of the protein C-terminal to the DNA binding domain was deleted. The protein expressed well and the cleaved protein was purified to homogeneity. Interestingly this protein was ineffective towards inhibiting the aggregation of hIAPP into mature fibrils (Table 2). This suggests the possibility that the core of the protein comprising the EF hand along with the intervening sequence might be the smallest functional unit capable of inhibiting the aggregation reaction.

TABLE 2

Summary of results obtained with NUCB1 and various NUCB1 protein variants shown in FIG. 29

| Protein (FIG. 29 No.) | Oligomeric State | Calcium Binding | Interaction with WT $G\alpha_{i1}$ | Inhibition of hIAPP Aggregation | | Dissociation of hIAPP Fibrils | |
|---|---|---|---|---|---|---|---|
| | | | | $-Ca^{2+}$ | $+Ca^{2+}$ | $-Ca^{2+}$ | $+Ca^{2+}$ |
| sNUCB1 (3) | Dimer | Yes | Yes | Yes | No | Yes | No |
| sNUCB1 Tetra (4) | Dimer | No | N.D. | Yes | Yes | Yes | Yes |
| sNUCB1(S44C) (5) | Dimer | Yes | Yes | Yes | N.D. | Yes | N.D. |
| sNUCB1 (G408Ter) (6) | Dimer | Yes | Yes | Yes | No | N.D. | N.D. |
| eNUCB1 (Q401Ter) (7) | Dimer | Yes | Yes | Yes | N.D. | N.D. | N.D. |
| sNUCB1 (W333Ter) (8) | Monomer | N.D. | Yes | Yes | N.D. | N.D. | N.D. |
| eNUCB1(233-400) | N.D. | Yes | Yes | Yes | N.D. | N.D. | N.D. |

TABLE 2-continued

Summary of results obtained with NUCB1 and various NUCB1 protein variants shown in FIG. 29

| Protein (FIG. 29 No.) | Oligomeric State | Calcium Binding | Interaction with WT $G\alpha_{i1}$ | Inhibition of hIAPP Aggregation | | Dissociation of hIAPP Fibrils | |
|---|---|---|---|---|---|---|---|
| | | | | $-Ca^{2+}$ | $+Ca^{2+}$ | $-Ca^{2+}$ | $+Ca^{2+}$ |
| (9) sNUCB1 (P240Ter) (10) | Monomer | No | N.D. | No | N.D. | N.D. | N.D. |

Certain biological sequences referenced herein by their "NCBI Accession Number" or common names can be accessed through the National Center of Biotechnology Information on the world wide web at http://www.ncbi.nlm.nih.gov.

Various patent and non-patent publications are cited herein, the disclosures of each of which are, to the extent necessary, incorporated herein by reference in their entireties.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. An isolated protein comprising a non-naturally occurring human nucleobindin 1 (NUCB1) protein variant, wherein said NUCB1 protein variant comprises an EF hand loop 1 domain, an intervening acidic region, an EF hand loop 2 domain, wherein said protein variant comprises at least one mutation in each loop region of each EF hand domain of said NUCB1 protein variant that inhibits calcium binding, wherein said protein variant does not include a deletion of either or both entire 12 amino acid loop EF-hand domains and/or intervening acidic region, and wherein said protein variant displays amyloid fibril disaggregation activity in the presence of calcium and/or amyloid fibril formation inhibitory activity in the presence of calcium.

2. The isolated protein of claim 1, wherein said NUCB1 protein variant comprises a first N-terminal proximal EF hand loop region of the SEQ ID NO: 7 and a second C-terminal proximal EF hand loop region of SEQ ID NO:8, wherein at least one residue in SEQ ID NO:7 is distinct from a corresponding residue of SEQ ID NO:9, and wherein at least one residue in SEQ ID NO:8 is distinct from a corresponding residue of SEQ ID NO:10.

3. The isolated protein of claim 2, wherein $Xaa_1$ of SEQ ID NO:7 and/or SEQ ID NO:8 is selected independently from alanine, serine, lysine, or arginine.

4. The isolated protein of claim 3, wherein $Xaa_3$ of SEQ ID NO:7 and/or SEQ ID NO:8 is selected independently from lysine or arginine.

5. The isolated protein of claim 3, wherein $Xaa_5$ of SEQ ID NO:7 and SEQ ID NO:8 is selected independently from lysine or arginine.

6. The isolated protein of claim 3, wherein $Xaa_{12}$ of SEQ ID NO:7 and/or SEQ ID NO:8 is selected independently from alanine, serine, lysine, or arginine.

7. The isolated protein of claim 2, wherein $Xaa_1$ of SEQ ID NO:7 and/or SEQ ID NO:8 is selected independently from lysine or arginine, wherein $Xaa_3$ of SEQ ID NO:7 and/or SEQ ID NO:8 is selected independently from lysine or arginine, wherein $Xaa_5$ of SEQ ID NO:7 and/or SEQ ID NO:8 is selected independently from lysine or arginine, and wherein $Xaa_{12}$ of SEQ ID NO:7 and/or SEQ ID NO:8 is selected independently from alanine, lysine, or arginine.

8. The isolated protein of claim 2, wherein $Xaa_1$ of both SEQ ID NO:7 and SEQ ID NO:8 is lysine and wherein $Xaa_{12}$ of both SEQ ID NO:7 and SEQ ID NO:8 is alanine.

9. The isolated protein of claim 7, wherein said first N-terminal proximal EF hand loop region is SEQ ID NO: 11 and wherein said second C-terminal proximal EF hand loop region is SEQ ID NO:12.

10. The isolated protein of claim 8, wherein said NUCB1 protein variant comprises SEQ ID NO:6.

11. The isolated protein according to claim 1, wherein said NUCB1 variant protein displays increased amyloid fibril disaggregation activity and/or increased amyloid fibril formation inhibitory activity relative to the naturally occurring NUCB1 protein when calcium is present at a concentration of 200 micromolar to at least 3 mM.

12. The isolated protein according to claim 1, wherein said NUCB1 protein variant has a C-terminal deletion of 1 to about 128 C-terminal amino acids of a NUCB1 protein.

13. The isolated protein according to claim 1, wherein said NUCB1 protein variant has: i) a C-terminal deletion of 1 to about 61 C-terminal amino acids of an NUCB1 protein and ii) a N-terminal deletion of about 1 to about 232 N-terminal amino acids of a NUCB1 protein.

14. The isolated protein according to claim 1, wherein said NUCB1 protein variant has a N-terminal deletion of about 31 to about 232 N-terminal amino acids of a NUCB1 protein.

15. The isolated protein of claim 14, wherein said NUCB1 protein comprises the polypeptide of SEQ ID NO:25.

16. The isolated protein according to claim 1, wherein said NUCB1 protein variant further comprises an operably linked protease cleavage site, purification tag, signal peptide, or combination thereof.

17. The isolated protein according to claim 1, wherein said NUCB1 protein variant further comprises a chemical modification selected from the group consisting of amidation, lipidation, glycosylation, pegylation, and combinations thereof.

18. The isolated protein according to claim 1, wherein said NUCB1 variant protein displays peptidase activity.

19. The isolated protein of claim 18, wherein said NUCB1 protein variant comprises at least one carboxypeptidase motif, said carboxypeptidase motif comprising a NQHTFEARDLELL motif (SEQ ID NO:21), a GLDPNRFNP motif (SEQ ID NO:22), a DGHFREKLQAA motif (SEQ ID NO:23), or a motif comprising one or more conservative substitutions of SEQ ID NO:21, SEQ ID NO:22, or SEQ ID NO:23.

20. A method of treating a subject suffering from amyloidosis, comprising the step of administering a therapeutically effective amount of a pharmaceutical composition comprising a non-naturally occurring nucleobindin 1 (NUCB1) variant protein, wherein the NUCB1 variant protein comprises at least one mutation in each loop region of each EF hand domain of said NUCB1 protein variant that inhibits calcium binding, wherein said protein variant does not include a deletion of either or both entire 12 amino acid loop EF-hand domains and/or intervening acidic region, and wherein said protein variant has amyloid fibril disaggregating activity in the presence of calcium and/or inhibits amyloid fibril formation in the presence of calcium, thereby treating a subject suffering from amyloidosis.

21. The method of claim 20, wherein said subject is a non-human primate, horse, cow, pig, dog, or cat.

22. The method of claim 21, wherein said subject is suffering from renal or hepatic amyloidosis.

23. A method for disaggregating amyloid fibrils comprising the step of contacting said fibrils with an exogenously provided and non-naturally occurring NUCB1 protein variant, wherein the NUCB1 variant protein comprises at least one mutation in each loop region of each EF hand domain of said NUCB1 protein variant that inhibits calcium binding, wherein said protein variant does not include a deletion of either or both entire 12 amino acid loop EF-hand domains and/or intervening acidic region, and wherein said protein variant has amyloid fibril disaggregating activity in the presence of calcium and/or inhibits amyloid fibril formation in the presence of calcium.

* * * * *

SEQUENCE LISTING

```
<160> NUMBER OF SEQ ID NOS: 39

<210> SEQ ID NO 1
<211> LENGTH: 430
<212> TYPE: PRT
<213> ORGANISM: Artificial
<220> FEATURE:
<223> OTHER INFORMATION: sequence of NUCB1 protein variant core
<220> FEATURE:
<221> NAME/KEY: MISC_FEATURE
<222> LOCATION: (159)..(159)
<223> OTHER INFORMATION: Xaa can be asparagine or tyrosine
<220> FEATURE:
<221> NAME/KEY: MISC_FEATURE
<222> LOCATION: (168)..(168)
<223> OTHER INFORMATION: Xaa can be lysine or arginine
<220> FEATURE:
<221> NAME/KEY: MISC_FEATURE
<222> LOCATION: (222)..(233)
<223> OTHER INFORMATION: Xaa can be any amino acid
<220> FEATURE:
<221> NAME/KEY: MISC_FEATURE
<222> LOCATION: (274)..(285)
<223> OTHER INFORMATION: Xaa can be any amino acid
<220> FEATURE:
<221> NAME/KEY: MISC_FEATURE
<222> LOCATION: (307)..(307)
<223> OTHER INFORMATION: Xaa is valine or methionine
<220> FEATURE:
<221> NAME/KEY: MISC_FEATURE
<222> LOCATION: (354)..(354)
<223> OTHER INFORMATION: Xaa is lysine or glutamine

<400> SEQUENCE: 1

Gly Ala Pro Asn Lys Glu Glu Thr Pro Ala Thr Glu Ser Pro Asp Thr
1               5                   10                  15

Gly Leu Tyr Tyr His Arg Tyr Leu Gln Glu Val Ile Asp Val Leu Glu
            20                  25                  30

Thr Asp Gly His Phe Arg Glu Lys Leu Gln Ala Ala Asn Ala Glu Asp
        35                  40                  45

Ile Lys Ser Gly Lys Leu Ser Arg Glu Leu Asp Phe Val Ser His His
    50                  55                  60
```

| | | | | | | | | | | | | | | | |
|---|---|---|---|---|---|---|---|---|---|---|---|---|---|---|---|

Val Arg Thr Lys Leu Asp Glu Leu Lys Arg Gln Glu Val Ser Arg Leu
65                  70                  75                  80

Arg Met Leu Leu Lys Ala Lys Met Asp Ala Glu Gln Asp Pro Asn Val
                    85                  90                  95

Gln Val Asp His Leu Asn Leu Lys Gln Phe Glu His Leu Asp Pro
                100                 105                 110

Gln Asn Gln His Thr Phe Glu Ala Arg Asp Leu Glu Leu Leu Ile Gln
                115                 120                 125

Thr Ala Thr Arg Asp Leu Ala Gln Tyr Asp Ala Ala His His Glu Glu
            130                 135                 140

Phe Lys Arg Tyr Glu Met Leu Lys Glu His Glu Arg Arg Xaa Leu
145                 150                 155                 160

Glu Ser Leu Gly Glu Glu Gln Xaa Lys Glu Ala Glu Arg Lys Leu Glu
                165                 170                 175

Glu Gln Gln Arg Arg His Arg Glu His Pro Lys Val Asn Val Pro Gly
                180                 185                 190

Ser Gln Ala Gln Leu Lys Glu Val Trp Glu Glu Leu Asp Gly Leu Asp
            195                 200                 205

Pro Asn Arg Phe Asn Pro Lys Thr Phe Phe Ile Leu His Xaa Xaa Xaa
            210                 215                 220

Xaa Xaa Xaa Xaa Xaa Xaa Xaa Xaa Xaa Leu Glu Ala Leu Phe Thr Lys
225                 230                 235                 240

Glu Leu Glu Lys Val Tyr Asp Pro Lys Asn Glu Glu Asp Asp Met Arg
                245                 250                 255

Glu Met Glu Glu Glu Arg Leu Arg Met Arg Glu His Val Met Lys Asn
                260                 265                 270

Val Xaa Xaa Xaa Xaa Xaa Xaa Xaa Xaa Xaa Xaa Phe Leu Ala
            275                 280                 285

Ser Thr Gln Arg Lys Glu Phe Gly Asp Thr Gly Glu Gly Trp Glu Thr
            290                 295                 300

Val Glu Xaa His Pro Ala Tyr Thr Glu Glu Leu Arg Arg Phe Glu
305                 310                 315                 320

Glu Glu Leu Ala Ala Arg Glu Ala Glu Leu Asn Ala Lys Ala Gln Arg
                325                 330                 335

Leu Ser Gln Glu Thr Glu Ala Leu Gly Arg Ser Gln Gly Arg Leu Glu
            340                 345                 350

Ala Xaa Lys Arg Glu Leu Gln Gln Ala Val Leu His Met Glu Gln Arg
    355                 360                 365

Lys Gln Gln Gln Gln Gln Gln Gly His Lys Ala Pro Ala His
370                 375                 380

Pro Glu Gly Gln Leu Lys Phe His Pro Asp Thr Asp Val Pro Val
385                 390                 395                 400

Pro Ala Pro Ala Gly Asp Gln Lys Glu Val Asp Thr Ser Glu Lys Lys
            405                 410                 415

Leu Leu Glu Arg Leu Pro Glu Val Glu Val Pro Gln His Leu
            420                 425                 430

<210> SEQ ID NO 2
<211> LENGTH: 461
<212> TYPE: PRT
<213> ORGANISM: Homo sapiens

<400> SEQUENCE: 2

Met Pro Pro Ser Gly Pro Arg Gly Thr Leu Leu Leu Pro Leu Leu
1               5                   10                  15

```
Leu Leu Leu Leu Leu Arg Ala Val Ala Val Pro Leu Glu Arg Gly
            20                  25                  30
Ala Pro Asn Lys Glu Glu Thr Pro Ala Thr Glu Ser Pro Asp Thr Gly
            35                  40                  45
Leu Tyr Tyr His Arg Tyr Leu Gln Glu Val Ile Asp Val Leu Glu Thr
 50                  55                  60
Asp Gly His Phe Arg Glu Lys Leu Gln Ala Ala Asn Ala Glu Asp Ile
 65                  70                  75                  80
Lys Ser Gly Lys Leu Ser Arg Glu Leu Asp Phe Val Ser His Val
                85                  90                  95
Arg Thr Lys Leu Asp Glu Leu Lys Arg Gln Glu Val Ser Arg Leu Arg
                100                 105                 110
Met Leu Leu Lys Ala Lys Met Asp Ala Glu Gln Asp Pro Asn Val Gln
            115                 120                 125
Val Asp His Leu Asn Leu Leu Lys Gln Phe Glu His Leu Asp Pro Gln
130                 135                 140
Asn Gln His Thr Phe Glu Ala Arg Asp Leu Glu Leu Leu Ile Gln Thr
145                 150                 155                 160
Ala Thr Arg Asp Leu Ala Gln Tyr Asp Ala Ala His His Glu Glu Phe
                165                 170                 175
Lys Arg Tyr Glu Met Leu Lys Glu His Glu Arg Arg Tyr Leu Glu
                180                 185                 190
Ser Leu Gly Glu Glu Gln Arg Lys Glu Ala Glu Arg Lys Leu Glu Glu
            195                 200                 205
Gln Gln Arg Arg His Arg Glu His Pro Lys Val Asn Val Pro Gly Ser
            210                 215                 220
Gln Ala Gln Leu Lys Glu Val Trp Glu Glu Leu Asp Gly Leu Asp Pro
225                 230                 235                 240
Asn Arg Phe Asn Pro Lys Thr Phe Phe Ile Leu His Asp Ile Asn Ser
                245                 250                 255
Asp Gly Val Leu Asp Glu Gln Glu Leu Glu Ala Leu Phe Thr Lys Glu
            260                 265                 270
Leu Glu Lys Val Tyr Asp Pro Lys Asn Glu Glu Asp Asp Met Arg Glu
            275                 280                 285
Met Glu Glu Glu Arg Leu Arg Met Arg Glu His Val Met Lys Asn Val
290                 295                 300
Asp Thr Asn Gln Asp Arg Leu Val Thr Leu Glu Glu Phe Leu Ala Ser
305                 310                 315                 320
Thr Gln Arg Lys Glu Phe Gly Asp Thr Gly Glu Gly Trp Glu Thr Val
                325                 330                 335
Glu Met His Pro Ala Tyr Thr Glu Glu Glu Leu Arg Arg Phe Glu Glu
            340                 345                 350
Glu Leu Ala Ala Arg Glu Ala Glu Leu Asn Ala Lys Ala Gln Arg Leu
            355                 360                 365
Ser Gln Glu Thr Glu Ala Leu Gly Arg Ser Gln Gly Arg Leu Glu Ala
            370                 375                 380
Gln Lys Arg Glu Leu Gln Gln Ala Val Leu His Met Glu Gln Arg Lys
385                 390                 395                 400
Gln Gln Gln Gln Gln Gln Gly His Lys Ala Pro Ala His Pro
                405                 410                 415
Glu Gly Gln Leu Lys Phe His Pro Asp Thr Asp Val Pro Val Pro
            420                 425                 430
Ala Pro Ala Gly Asp Gln Lys Glu Val Asp Thr Ser Glu Lys Lys Leu
```

```
                      435                 440                 445
Leu Glu Arg Leu Pro Glu Val Glu Val Pro Gln His Leu
    450                 455                 460

<210> SEQ ID NO 3
<211> LENGTH: 436
<212> TYPE: PRT
<213> ORGANISM: Artificial
<220> FEATURE:
<223> OTHER INFORMATION: synthetic
<220> FEATURE:
<221> NAME/KEY: MISC_FEATURE
<223> OTHER INFORMATION: NUCB1 deletion amino acids 1-31 with six amino
      acid portion of protease cleavage site at N-terminus

<400> SEQUENCE: 3

Gly Pro His Met Ala Ser Gly Ala Pro Asn Lys Glu Thr Pro Ala
1               5                   10                  15

Thr Glu Ser Pro Asp Thr Gly Leu Tyr Tyr His Arg Tyr Leu Gln Glu
            20                  25                  30

Val Ile Asp Val Leu Glu Thr Asp Gly His Phe Arg Glu Lys Leu Gln
        35                  40                  45

Ala Ala Asn Ala Glu Asp Ile Lys Ser Gly Lys Leu Ser Arg Glu Leu
    50                  55                  60

Asp Phe Val Ser His His Val Arg Thr Lys Leu Asp Glu Leu Lys Arg
65                  70                  75                  80

Gln Glu Val Ser Arg Leu Arg Met Leu Leu Lys Ala Lys Met Asp Ala
                85                  90                  95

Glu Gln Asp Pro Asn Val Gln Val Asp His Leu Asn Leu Leu Lys Gln
            100                 105                 110

Phe Glu His Leu Asp Pro Gln Asn Gln His Thr Phe Glu Ala Arg Asp
        115                 120                 125

Leu Glu Leu Leu Ile Gln Thr Ala Thr Arg Asp Leu Ala Gln Tyr Asp
    130                 135                 140

Ala Ala His His Glu Glu Phe Lys Arg Tyr Glu Met Leu Lys Glu His
145                 150                 155                 160

Glu Arg Arg Arg Tyr Leu Glu Ser Leu Gly Glu Glu Gln Arg Lys Glu
                165                 170                 175

Ala Glu Arg Lys Leu Glu Glu Gln Gln Arg His Arg Glu His Pro
            180                 185                 190

Lys Val Asn Val Pro Gly Ser Gln Ala Gln Leu Lys Glu Val Trp Glu
        195                 200                 205

Glu Leu Asp Gly Leu Asp Pro Asn Arg Phe Asn Pro Lys Thr Phe Phe
    210                 215                 220

Ile Leu His Asp Ile Asn Ser Asp Gly Val Leu Asp Glu Gln Glu Leu
225                 230                 235                 240

Glu Ala Leu Phe Thr Lys Glu Leu Glu Lys Val Tyr Asp Pro Lys Asn
                245                 250                 255

Glu Glu Asp Asp Met Arg Glu Met Glu Glu Glu Arg Leu Arg Met Arg
            260                 265                 270

Glu His Val Met Lys Asn Val Asp Thr Asn Gln Asp Arg Leu Val Thr
        275                 280                 285

Leu Glu Glu Phe Leu Ala Ser Thr Gln Arg Lys Glu Phe Gly Asp Thr
    290                 295                 300

Gly Glu Gly Trp Glu Thr Val Glu Met His Pro Ala Tyr Thr Glu Glu
305                 310                 315                 320

Glu Leu Arg Arg Phe Glu Glu Glu Leu Ala Ala Arg Glu Ala Glu Leu
```

```
                      325                 330                 335
Asn Ala Lys Ala Gln Arg Leu Ser Gln Glu Thr Glu Ala Leu Gly Arg
                340                 345                 350

Ser Gln Gly Arg Leu Glu Ala Gln Lys Arg Glu Leu Gln Gln Ala Val
            355                 360                 365

Leu His Met Glu Gln Arg Lys Gln Gln Gln Gln Gln Gln Gln Gly His
        370                 375                 380

Lys Ala Pro Ala Ala His Pro Glu Gly Gln Leu Lys Phe His Pro Asp
385                 390                 395                 400

Thr Asp Asp Val Pro Val Pro Ala Pro Ala Gly Asp Gln Lys Glu Val
                405                 410                 415

Asp Thr Ser Glu Lys Lys Leu Leu Glu Arg Leu Pro Glu Val Glu Val
            420                 425                 430

Pro Gln His Leu
        435

<210> SEQ ID NO 4
<211> LENGTH: 420
<212> TYPE: PRT
<213> ORGANISM: Mus musculus

<400> SEQUENCE: 4

Met Arg Trp Arg Ile Ile Gln Val Gln Tyr Cys Phe Leu Leu Val Pro
1               5                   10                  15

Cys Met Leu Thr Ala Leu Glu Ala Val Pro Ile Asp Val Asp Lys Thr
            20                  25                  30

Lys Val His Asn Thr Glu Pro Val Glu Asn Ala Arg Ile Glu Pro Pro
        35                  40                  45

Asp Thr Gly Leu Tyr Tyr Asp Glu Tyr Leu Lys Gln Val Ile Glu Val
    50                  55                  60

Leu Glu Thr Asp Pro His Phe Arg Glu Lys Leu Gln Lys Ala Asp Ile
65                  70                  75                  80

Glu Glu Ile Arg Ser Gly Arg Leu Ser Gln Glu Leu Asp Leu Val Ser
                85                  90                  95

His Lys Val Arg Thr Arg Leu Asp Glu Leu Lys Arg Gln Glu Val Gly
            100                 105                 110

Arg Leu Arg Met Leu Ile Lys Ala Lys Leu Asp Ala Leu Gln Asp Thr
        115                 120                 125

Gly Met Asn His His Leu Leu Leu Lys Gln Phe Glu His Leu Asn His
    130                 135                 140

Gln Asn Pro Asn Thr Phe Glu Ser Arg Asp Leu Asp Met Leu Ile Lys
145                 150                 155                 160

Ala Ala Thr Ala Asp Leu Glu Gln Tyr Asp Arg Thr Arg His Glu Glu
                165                 170                 175

Phe Lys Lys Tyr Glu Met Met Lys Glu His Glu Arg Arg Glu Tyr Leu
            180                 185                 190

Lys Thr Leu Ser Glu Glu Lys Arg Lys Glu Glu Ser Lys Phe Glu
        195                 200                 205

Glu Met Lys Arg Lys His Glu Asp His Pro Lys Val Asn His Pro Gly
    210                 215                 220

Ser Lys Asp Gln Leu Lys Glu Val Trp Glu Thr Asp Gly Leu Asp
225                 230                 235                 240

Pro Asn Asp Phe Asp Pro Lys Thr Phe Phe Lys Leu His Asp Val Asn
                245                 250                 255

Asn Asp Gly Phe Leu Asp Glu Gln Glu Leu Glu Ala Leu Phe Thr Arg
```

```
                   260                 265                 270
Glu Leu Glu Lys Val Tyr Asn Pro Gln Asn Ala Glu Asp Asp Met Ile
                275                 280                 285

Glu Met Glu Glu Glu Arg Leu Arg Met Arg Glu His Val Met Ser Glu
            290                 295                 300

Ile Asp Asn Asn Lys Asp Arg Leu Val Thr Leu Glu Phe Leu Arg
305                 310                 315                 320

Ala Thr Glu Lys Lys Glu Phe Leu Glu Pro Asp Ser Trp Glu Thr Leu
                325                 330                 335

Asp Gln Gln Leu Phe Thr Glu Asp Glu Leu Lys Glu Tyr Glu Ser
            340                 345                 350

Ile Ile Ala Ile Gln Glu Asn Glu Leu Lys Lys Arg Ala Glu Glu Leu
                355                 360                 365

Gln Lys Gln Lys Glu Asp Leu Gln Arg Gln His Asp His Leu Glu Ala
            370                 375                 380

Gln Lys Gln Glu Tyr His Gln Ala Val Gln His Leu Gln Lys Lys
385                 390                 395                 400

Leu Gln Gln Gly Ile Ala Pro Ser Gly Pro Ala Gly Glu Leu Lys Phe
                405                 410                 415

Glu Pro Arg Met
            420

<210> SEQ ID NO 5
<211> LENGTH: 389
<212> TYPE: PRT
<213> ORGANISM: Mus musculus
<220> FEATURE:
<221> NAME/KEY: MISC_FEATURE
<223> OTHER INFORMATION: NUCB2 N-terminal deletion of amino acids  2-32

<400> SEQUENCE: 5

Met Lys Val His Asn Thr Glu Pro Val Glu Asn Ala Arg Ile Glu Pro
1               5                   10                  15

Pro Asp Thr Gly Leu Tyr Tyr Asp Glu Tyr Leu Lys Gln Val Ile Glu
                20                  25                  30

Val Leu Glu Thr Asp Pro His Phe Arg Glu Lys Leu Gln Lys Ala Asp
            35                  40                  45

Ile Glu Glu Ile Arg Ser Gly Arg Leu Ser Gln Glu Leu Asp Leu Val
50                  55                  60

Ser His Lys Val Arg Thr Arg Leu Asp Glu Leu Lys Arg Gln Glu Val
65                  70                  75                  80

Gly Arg Leu Arg Met Leu Ile Lys Ala Lys Leu Asp Ala Leu Gln Asp
                85                  90                  95

Thr Gly Met Asn His His Leu Leu Leu Lys Gln Phe Glu His Leu Asn
            100                 105                 110

His Gln Asn Pro Asn Thr Phe Glu Ser Arg Asp Leu Asp Met Leu Ile
        115                 120                 125

Lys Ala Ala Thr Ala Asp Leu Glu Gln Tyr Asp Arg Thr Arg His Glu
130                 135                 140

Glu Phe Lys Lys Tyr Glu Met Met Lys Glu His Glu Arg Arg Glu Tyr
145                 150                 155                 160

Leu Lys Thr Leu Ser Glu Glu Lys Arg Lys Glu Glu Ser Lys Phe
                165                 170                 175

Glu Glu Met Lys Arg Lys His Glu Asp His Pro Lys Val Asn His Pro
            180                 185                 190

Gly Ser Lys Asp Gln Leu Lys Glu Val Trp Glu Glu Thr Asp Gly Leu
```

```
                195                 200                 205
Asp Pro Asn Asp Phe Asp Pro Lys Thr Phe Phe Lys Leu His Asp Val
    210                 215                 220
Asn Asn Asp Gly Phe Leu Asp Glu Gln Glu Leu Glu Ala Leu Phe Thr
225                 230                 235                 240
Arg Glu Leu Glu Lys Val Tyr Asn Pro Gln Asn Ala Glu Asp Asp Met
                245                 250                 255
Ile Glu Met Glu Glu Arg Leu Arg Met Arg Glu His Val Met Ser
                260                 265                 270
Glu Ile Asp Asn Asn Lys Asp Arg Leu Val Thr Leu Glu Glu Phe Leu
        275                 280                 285
Arg Ala Thr Glu Lys Lys Glu Phe Leu Glu Pro Asp Ser Trp Glu Thr
    290                 295                 300
Leu Asp Gln Gln Gln Leu Phe Thr Glu Asp Glu Leu Lys Glu Tyr Glu
305                 310                 315                 320
Ser Ile Ile Ala Ile Gln Glu Asn Glu Leu Lys Lys Arg Ala Glu Glu
                325                 330                 335
Leu Gln Lys Gln Lys Glu Asp Leu Gln Arg Gln His Asp His Leu Glu
            340                 345                 350
Ala Gln Lys Gln Glu Tyr His Gln Ala Val Gln His Leu Glu Gln Lys
        355                 360                 365
Lys Leu Gln Gln Gly Ile Ala Pro Ser Gly Pro Ala Gly Glu Leu Lys
    370                 375                 380
Phe Glu Pro Arg Met
385

<210> SEQ ID NO 6
<211> LENGTH: 435
<212> TYPE: PRT
<213> ORGANISM: Artificial
<220> FEATURE:
<223> OTHER INFORMATION: synthetic
<220> FEATURE:
<221> NAME/KEY: MISC_FEATURE
<223> OTHER INFORMATION: NUCB1 protein variant with deletion of amino
      acids 1-31; D253K, E264A, D305K, E316A and six additional amino
      acids from protease cleavage site at N-terminal

<400> SEQUENCE: 6

Gly Pro His Met Ala Ser Gly Ala Pro Asn Lys Glu Glu Thr Pro Ala
1               5                   10                  15

Thr Glu Ser Pro Asp Thr Gly Leu Tyr Tyr His Arg Tyr Leu Gln Glu
                20                  25                  30

Val Ile Asp Val Leu Glu Thr Asp Gly His Phe Arg Glu Lys Leu Gln
            35                  40                  45

Ala Ala Asn Ala Glu Asp Lys Ser Gly Lys Leu Ser Arg Glu Leu Asp
    50                  55                  60

Phe Val Ser His His Val Arg Thr Lys Leu Asp Glu Leu Lys Arg Gln
65                  70                  75                  80

Glu Val Ser Arg Leu Arg Met Leu Leu Lys Ala Lys Met Asp Ala Glu
                85                  90                  95

Gln Asp Pro Asn Val Gln Val Asp His Leu Asn Leu Leu Lys Gln Phe
            100                 105                 110

Glu His Leu Asp Pro Gln Asn Gln His Thr Phe Glu Ala Arg Asp Leu
        115                 120                 125

Glu Leu Leu Ile Gln Thr Ala Thr Arg Asp Leu Ala Gln Tyr Asp Ala
    130                 135                 140
```

```
Ala His His Glu Glu Phe Lys Arg Tyr Glu Met Leu Lys Glu His Glu
145                 150                 155                 160

Arg Arg Arg Tyr Leu Glu Ser Leu Gly Glu Gln Arg Lys Glu Ala
            165                 170                 175

Glu Arg Lys Leu Glu Glu Gln Gln Arg Arg His Arg Glu His Pro Lys
            180                 185                 190

Val Asn Val Pro Gly Ser Gln Ala Gln Leu Lys Glu Val Trp Glu Glu
            195                 200                 205

Leu Asp Gly Leu Asp Pro Asn Arg Phe Asn Pro Lys Thr Phe Phe Ile
210                 215                 220

Leu His Lys Ile Asn Ser Asp Gly Val Leu Asp Glu Gln Ala Leu Glu
225                 230                 235                 240

Ala Leu Phe Thr Lys Glu Leu Glu Lys Val Tyr Asp Pro Lys Asn Glu
            245                 250                 255

Glu Asp Asp Met Arg Glu Met Glu Glu Glu Arg Leu Arg Met Arg Glu
            260                 265                 270

His Val Met Lys Asn Val Lys Thr Asn Gln Asp Arg Leu Val Thr Leu
            275                 280                 285

Glu Ala Phe Leu Ala Ser Thr Gln Arg Lys Glu Phe Gly Asp Thr Gly
290                 295                 300

Glu Gly Trp Glu Thr Val Glu Met His Pro Ala Tyr Thr Glu Glu Glu
305                 310                 315                 320

Leu Arg Arg Phe Glu Glu Leu Ala Ala Arg Glu Ala Glu Leu Asn
            325                 330                 335

Ala Lys Ala Gln Arg Leu Ser Gln Glu Thr Glu Ala Leu Gly Arg Ser
            340                 345                 350

Gln Gly Arg Leu Glu Ala Gln Lys Arg Glu Leu Gln Gln Ala Val Leu
            355                 360                 365

His Met Glu Gln Arg Lys Gln Gln Gln Gln Gln Gln Gly His Lys
            370                 375                 380

Ala Pro Ala Ala His Pro Glu Gly Gln Leu Lys Phe His Pro Asp Thr
385                 390                 395                 400

Asp Asp Val Pro Val Pro Ala Pro Ala Gly Asp Gln Lys Glu Val Asp
            405                 410                 415

Thr Ser Glu Lys Lys Leu Leu Glu Arg Leu Pro Glu Val Glu Val Pro
            420                 425                 430

Gln His Leu
        435

<210> SEQ ID NO 7
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(12)
<223> OTHER INFORMATION: at least one residue in SEQ ID NO:7 is distinct
      from a corresponding residue of the 12 amino acid loop region of
      the first N-terminal proximal EF hand loop domain of NUCB1

<400> SEQUENCE: 7

Xaa Xaa Xaa Xaa Xaa Xaa Xaa Xaa Xaa Xaa Xaa Xaa
1               5                   10

<210> SEQ ID NO 8
<211> LENGTH: 12
<212> TYPE: PRT
```

```
<213> ORGANISM: Artificial
<220> FEATURE:
<223> OTHER INFORMATION: NUCB1 protein variant C-terminal proximal EF
      hand loop domain residues 1-12
<220> FEATURE:
<221> NAME/KEY: MISC_FEATURE
<222> LOCATION: (1)..(12)
<223> OTHER INFORMATION: at least one residue in SEQ ID NO:8 is distinct
      from a corresponding residue of the 12 amino acid loop region of
      the second C-terminal proximal EF hand loop domain of NUCB1

<400> SEQUENCE: 8

Xaa Xaa Xaa Xaa Xaa Xaa Xaa Xaa Xaa Xaa Xaa Xaa
1               5                   10

<210> SEQ ID NO 9
<211> LENGTH: 12
<212> TYPE: PRT
<213> ORGANISM: Homo sapiens
<220> FEATURE:
<221> NAME/KEY: MISC_FEATURE
<223> OTHER INFORMATION: NUCB1 n-terminal proximal EF hand loop domain
      residues 1-12 corresponding to residues 253 to 264 of NUCB1

<400> SEQUENCE: 9

Asp Ile Asn Ser Asp Gly Val Leu Asp Glu Gln Glu
1               5                   10

<210> SEQ ID NO 10
<211> LENGTH: 12
<212> TYPE: PRT
<213> ORGANISM: Homo sapiens
<220> FEATURE:
<221> NAME/KEY: MISC_FEATURE
<223> OTHER INFORMATION: NUCB1 C-terminal proximal EF hand loop domain
      residues 1-12 corresponding to residues 305-316 of NUCB1

<400> SEQUENCE: 10

Asp Thr Asn Gln Asp Arg Leu Val Thr Leu Glu Glu
1               5                   10

<210> SEQ ID NO 11
<211> LENGTH: 12
<212> TYPE: PRT
<213> ORGANISM: Artificial
<220> FEATURE:
<223> OTHER INFORMATION: NUCB1 N-TERMINAL EF-HAND LOOP  MUTANT D253K,
      E264A

<400> SEQUENCE: 11

Lys Ile Asn Ser Asp Gly Val Leu Asp Glu Gln Ala
1               5                   10

<210> SEQ ID NO 12
<211> LENGTH: 12
<212> TYPE: PRT
<213> ORGANISM: Artificial
<220> FEATURE:
<223> OTHER INFORMATION: NUCB1 C-TERMINAL EF-HAND LOOP  MUTANT D305K,
      E316A

<400> SEQUENCE: 12

Lys Thr Asn Gln Asp Arg Leu Val Thr Leu Glu Ala
1               5                   10

<210> SEQ ID NO 13
<211> LENGTH: 12
<212> TYPE: PRT
<213> ORGANISM: Unknown
<220> FEATURE:
```

<223> OTHER INFORMATION: Calmodulin EF Hand 4 Loop domain

<400> SEQUENCE: 13

Asp Ile Asp Gly Asp Gly Gln Val Asn Tyr Glu Glu
1               5                   10

<210> SEQ ID NO 14
<211> LENGTH: 12
<212> TYPE: PRT
<213> ORGANISM: unknown
<220> FEATURE:
<223> OTHER INFORMATION: Calmodulin EF Hand 2 Loop domain

<400> SEQUENCE: 14

Asp Ala Asp Gly Asn Gly Thr Ile Asp Phe Pro Glu
1               5                   10

<210> SEQ ID NO 15
<211> LENGTH: 12
<212> TYPE: PRT
<213> ORGANISM: unknown
<220> FEATURE:
<223> OTHER INFORMATION: Calmodulin EF Hand 3 Loop domain

<400> SEQUENCE: 15

Asp Lys Asp Gly Asn Gly Tyr Ile Ser Ala Ala Glu
1               5                   10

<210> SEQ ID NO 16
<211> LENGTH: 12
<212> TYPE: PRT
<213> ORGANISM: unknown
<220> FEATURE:
<223> OTHER INFORMATION: Calmodulin EF Hand 1 Loop domain

<400> SEQUENCE: 16

Asp Lys Asp Gly Asp Gly Thr Ile Thr Thr Lys Glu
1               5                   10

<210> SEQ ID NO 17
<211> LENGTH: 1386
<212> TYPE: DNA
<213> ORGANISM: Homo sapiens
<220> FEATURE:
<221> NAME/KEY: misc_feature
<223> OTHER INFORMATION: NUCB1 nucleotide sequence

<400> SEQUENCE: 17

```
atgcctccct ctgggccccg aggaaccctc cttctgttgc cgctgctgct gctgctcctg        60
cttcgcgccg tgctggctgt cccccctgga g cgagggggcgc ccaacaagga ggagacccct     120
gcgactgaga gtcccgacac aggcctgtac taccaccggt acctccagga ggtcatcgat       180
gtactggaga cggatgggca tttccgagag aagctgcagg ctgccaatgc ggaggacatc       240
aagagcggga agctgagccg agagctggac tttgtcagcc accacgtccg caccaagctg       300
gatgagctca gcgacaggag ggtgtcacgg ctgcggatgc tgctcaaggc caagatggac       360
gccgagcagg atcccaatgt acaggtggat catctgaatc tcctgaaaca gtttgaacac       420
ctggaccctc agaaccagca tacattcgag gcccgcgacc tggagctgct gatccagacg       480
gccacccggg accttgccca gtacgacgca gcccatcatg aagagttcaa gcgctacgag       540
atgcttaagg aacacgagag acggcgttat ctggagtcac tgggagagga gcagagaaag       600
gaggcggaga ggaagctgga agagcaacag cgccggcacc gcgagcaccc taaagtcaac       660
gtgcctggca gccaagccca gttgaaggag gtgtgggagg agctggatgg actggacccc       720
```

| | | |
|---|---|---|
| aacaggttta accccaagac cttcttcata ctgcatgata tcaacagtga tggtgtcctg | 780 | |
| gatgagcagg agctggaggc actcttcacc aaggagctgg agaaagtgta cgacccaaag | 840 | |
| aatgaggagg acgacatgcg ggagatggag gaggagcgac tgcgcatgcg ggagcatgtg | 900 | |
| atgaagaatg tggacaccaa ccaggaccgc ctcgtgaccc tggaggagtt cctcgcatcc | 960 | |
| actcagagga aggagtttgg ggacaccggg gagggctggg agacagtgga gatgcacccct | 1020 | |
| gcctacaccg aggaagagct gaggcgcttt gaagaggagc tggctgcccg ggaggcagag | 1080 | |
| ctgaatgcca aggcccagcg cctcagccag gagacagagg ctctagggcg gtcccagggc | 1140 | |
| cgcctggagg cccagaagag agagctgcag caggctgtgc tgcacatgga gcagcggaag | 1200 | |
| cagcagcagc agcagcagca aggccacaag gccccggctg cccaccctga ggggcagctc | 1260 | |
| aagttccacc cagacacaga cgatgtacct gtcccagctc cagccggtga ccagaaggag | 1320 | |
| gtggacactt cagaaaagaa acttctcgag cggctccctg aggttgaggt gccccagcat | 1380 | |
| ctgtga | 1386 | |

<210> SEQ ID NO 18
<211> LENGTH: 1263
<212> TYPE: DNA
<213> ORGANISM: Mus musculus
<220> FEATURE:
<221> NAME/KEY: misc_feature
<223> OTHER INFORMATION: NUCB2 sequence

<400> SEQUENCE: 18

| | | |
|---|---|---|
| atgaggtgga ggatcatcca agtacagtac tgttttctct tggttccgtg catgctgacc | 60 | |
| gctctggaag ctgttcctat cgatgtggac aagaccaaag tacacaacac tgagccagtg | 120 | |
| gaaaatgcaa ggatagagcc accagatact ggactttatt atgatgaata cctcaagcaa | 180 | |
| gtgattgaag tcttggaaac agatccacat ttcagagaaa agctccagaa agcagacata | 240 | |
| gaggagataa ggagcgggag gctgagtcaa gagctggact tagtaagtca caaagtgagg | 300 | |
| acgagactgg atgagctgaa gaggcaagaa gtaggaagac tgcggatgct catcaaagct | 360 | |
| aagctggatg cccttcaaga cactggcatg aatcaccacc ttcttctgaa gcagtttgaa | 420 | |
| cacctgaacc accagaatcc taacacattt gaatccagag atttggatat gctaatcaaa | 480 | |
| gcagctaccg cggatctgga gcaatatgac cggactcggc atgaagagtt taagaagtac | 540 | |
| gagatgatga aggaacacga gcggagagag tatttaaaaa cgctgagtga ggagaagagg | 600 | |
| aaagaagaag agtctaagtt tgaagagatg aagaggaagc acgaagacca ccccaaagtt | 660 | |
| aatcatcccg gaagcaaaga tcaactaaaa gaggtttggg aagagactga tggattggac | 720 | |
| cctaatgact ttgaccccaa gacatttttc aaattacatg atgttaacaa cgatggattc | 780 | |
| ctggatgaac aagaattaga agcactattc acaagagagt tggagaaagt gtataaccca | 840 | |
| caaaatgcag aggacgatat gatagaaatg aagaggagaa ggctcaggat gagagaacac | 900 | |
| gtcatgagtg agattgataa caacaaagac cgattggtga ctctggagga attcctgaga | 960 | |
| gctacagaga gaaagaatt cctggagcct gatagctggg agacactgga ccagcaacag | 1020 | |
| ttattcaccg aggacgagct taaagagtat gaaagcatta ttgctatcca agagaacgag | 1080 | |
| cttaagaaga gggcggaaga gctgcagaaa cagaaggagg atctgcagcg gcagcacgac | 1140 | |
| cacctcgagg cgcagaagca ggagtatcat caggccgtcc agcacctgga acagaagaaa | 1200 | |
| cttcaacaag gcattgctcc atcagggcca gcgggagagc tgaagtttga gccacgtatg | 1260 | |
| taa | 1263 | |

```
<210> SEQ ID NO 19
<211> LENGTH: 33
<212> TYPE: DNA
<213> ORGANISM: Artificial
<220> FEATURE:
<223> OTHER INFORMATION: 5' amplification oligo for NUCB1 amino acid 1-
      31deletion

<400> SEQUENCE: 19
cgccgctagc atgcctccct ctgggccccg agg                                33

<210> SEQ ID NO 20
<211> LENGTH: 42
<212> TYPE: DNA
<213> ORGANISM: Artificial
<220> FEATURE:
<223> OTHER INFORMATION: 3' Amplification oligonucleotide for NUCB1
      expression vector clone

<400> SEQUENCE: 20
cgccaagctt tcacagatgc tggggcacct caacctcagg ga                      42

<210> SEQ ID NO 21
<211> LENGTH: 13
<212> TYPE: PRT
<213> ORGANISM: Homo sapiens

<400> SEQUENCE: 21

Asn Gln His Thr Phe Glu Ala Arg Asp Leu Glu Leu Leu
1               5                   10

<210> SEQ ID NO 22
<211> LENGTH: 9
<212> TYPE: PRT
<213> ORGANISM: Homo sapiens

<400> SEQUENCE: 22

Gly Leu Asp Pro Asn Arg Phe Asn Pro
1               5

<210> SEQ ID NO 23
<211> LENGTH: 11
<212> TYPE: PRT
<213> ORGANISM: Homo sapiens

<400> SEQUENCE: 23

Asp Gly His Phe Arg Glu Lys Leu Gln Ala Ala
1               5                   10

<210> SEQ ID NO 24
<211> LENGTH: 1293
<212> TYPE: DNA
<213> ORGANISM: Artificial
<220> FEATURE:
<223> OTHER INFORMATION: synthetic
<220> FEATURE:
<221> NAME/KEY: CDS
<222> LOCATION: (1)..(1290)

<400> SEQUENCE: 24 ggg gcg ccc aac aag gag gag acc cct gcg act gag tgc gcc gac aca    48
Gly Ala Pro Asn Lys Glu Glu Thr Pro Ala Thr Glu Cys Ala Asp Thr
1               5                   10                  15 ggc ctg tac tac cac cgg tac ctc cag gag gtc atc gat gta ctg gag    96
Gly Leu Tyr Tyr His Arg Tyr Leu Gln Glu Val Ile Asp Val Leu Glu
            20                  25                  30
```

```
acg gat ggg cat ttc cga gag aag ctg cag gct gcc aat gcg gag gac    144
Thr Asp Gly His Phe Arg Glu Lys Leu Gln Ala Ala Asn Ala Glu Asp
         35                  40                  45 atc aag agc ggg aag ctg agc cga gag ctg gac ttt gtc agc cac cac    192
Ile Lys Ser Gly Lys Leu Ser Arg Glu Leu Asp Phe Val Ser His His
 50                  55                  60 gtc cgc acc aag ctg gat gag ctc aag cga cag gag gtg tca cgg ctg    240
Val Arg Thr Lys Leu Asp Glu Leu Lys Arg Gln Glu Val Ser Arg Leu
 65                  70                  75                  80 cgg atg ctg ctc aag gcc aag atg gac gcc gag cag gat ccc aat gta    288
Arg Met Leu Leu Lys Ala Lys Met Asp Ala Glu Gln Asp Pro Asn Val
                 85                  90                  95 cag gtg gat cat ctg aat ctc ctg aaa cag ttt gaa cac ctg gac cct    336
Gln Val Asp His Leu Asn Leu Leu Lys Gln Phe Glu His Leu Asp Pro
            100                 105                 110 cag aac cag cat aca ttc gag gcc cgc gac ctg gag ctg ctg atc cag    384
Gln Asn Gln His Thr Phe Glu Ala Arg Asp Leu Glu Leu Leu Ile Gln
        115                 120                 125 acg gcc acc cgg gac ctt gcc cag tac gac gca gcc cat cat gaa gag    432
Thr Ala Thr Arg Asp Leu Ala Gln Tyr Asp Ala Ala His His Glu Glu
130                 135                 140 ttc aag cgc tac gag atg ctt aag gaa cac gag aga cgg cgt tat ctg    480
Phe Lys Arg Tyr Glu Met Leu Lys Glu His Glu Arg Arg Arg Tyr Leu
145                 150                 155                 160 gag tca ctg gga gag gag cag aga aag gag gcg gag agg aag ctg gaa    528
Glu Ser Leu Gly Glu Glu Gln Arg Lys Glu Ala Glu Arg Lys Leu Glu
                165                 170                 175 gag caa cag cgc cgg cac cgc gag cac cct aaa gtc aac gtg cct ggc    576
Glu Gln Gln Arg Arg His Arg Glu His Pro Lys Val Asn Val Pro Gly
            180                 185                 190 agc caa gcc cag ttg aag gag gtg tgg gag gag ctg gat gga ctg gac    624
Ser Gln Ala Gln Leu Lys Glu Val Trp Glu Glu Leu Asp Gly Leu Asp
        195                 200                 205 ccc aac agg ttt aac ccc aag acc ttc ttc ata ctg cat gat atc aac    672
Pro Asn Arg Phe Asn Pro Lys Thr Phe Phe Ile Leu His Asp Ile Asn
210                 215                 220 agt gat ggt gtc ctg gat gag cag gag ctg gag gca ctc ttc acc aag    720
Ser Asp Gly Val Leu Asp Glu Gln Glu Leu Glu Ala Leu Phe Thr Lys
225                 230                 235                 240 gag ctg gag aaa gtg tac gac cca aag aat gag gag gac gac atg cgg    768
Glu Leu Glu Lys Val Tyr Asp Pro Lys Asn Glu Glu Asp Asp Met Arg
                245                 250                 255 gag atg gag gag gag cga ctg cgc atg cgg gag cat gtg atg aag aat    816
Glu Met Glu Glu Glu Arg Leu Arg Met Arg Glu His Val Met Lys Asn
            260                 265                 270 gtg gac acc aac cag gac cgc ctc gtg acc ctg gag gag ttc ctc gca    864
Val Asp Thr Asn Gln Asp Arg Leu Val Thr Leu Glu Glu Phe Leu Ala
        275                 280                 285 tcc act cag agg aag gag ttt ggg gac acc ggg gag ggc tgg gag aca    912
Ser Thr Gln Arg Lys Glu Phe Gly Asp Thr Gly Glu Gly Trp Glu Thr
290                 295                 300 gtg gag atg cac cct gcc tac acc gag gaa gag ctg agg cgc ttt gaa    960
Val Glu Met His Pro Ala Tyr Thr Glu Glu Glu Leu Arg Arg Phe Glu
305                 310                 315                 320 gag gag ctg gct gcc cgg gag gca gag ctg aat gcc aag gcc cag cgc   1008
Glu Glu Leu Ala Ala Arg Glu Ala Glu Leu Asn Ala Lys Ala Gln Arg
                325                 330                 335 ctc agc cag gag aca gag gct cta ggg cgg tcc cag ggc cgc ctg gag   1056
Leu Ser Gln Glu Thr Glu Ala Leu Gly Arg Ser Gln Gly Arg Leu Glu
            340                 345                 350
```

```
gcc cag aag aga gag ctg cag cag gct gtg ctg cac atg gag cag cgg      1104
Ala Gln Lys Arg Glu Leu Gln Gln Ala Val Leu His Met Glu Gln Arg
    355                 360                 365 aag cag cag cag cag cag cag caa ggc cac aag gcc ccg gct gcc cac      1152
Lys Gln Gln Gln Gln Gln Gln Gln Gly His Lys Ala Pro Ala Ala His
370                 375                 380 cct gag ggg cag ctc aag ttc cac cca gac aca gac gat gta cct gtc      1200
Pro Glu Gly Gln Leu Lys Phe His Pro Asp Thr Asp Asp Val Pro Val
385                 390                 395                 400 cca gct cca gcc ggt gac cag aag gag gtg gac act tca gaa aag aaa      1248
Pro Ala Pro Ala Gly Asp Gln Lys Glu Val Asp Thr Ser Glu Lys Lys
            405                 410                 415 ctt ctc gag cgg ctc cct gag gtt gag gtg ccc cag cat ctg tga          1293
Leu Leu Glu Arg Leu Pro Glu Val Glu Val Pro Gln His Leu
        420                 425                 430
```

<210> SEQ ID NO 25
<211> LENGTH: 430
<212> TYPE: PRT
<213> ORGANISM: Artificial
<220> FEATURE:
<223> OTHER INFORMATION: Synthetic Construct

<400> SEQUENCE: 25

```
Gly Ala Pro Asn Lys Glu Glu Thr Pro Ala Thr Glu Cys Ala Asp Thr
1               5                   10                  15

Gly Leu Tyr Tyr His Arg Tyr Leu Gln Glu Val Ile Asp Val Leu Glu
            20                  25                  30

Thr Asp Gly His Phe Arg Glu Lys Leu Gln Ala Ala Asn Ala Glu Asp
        35                  40                  45

Ile Lys Ser Gly Lys Leu Ser Arg Glu Leu Asp Phe Val Ser His His
50                  55                  60

Val Arg Thr Lys Leu Asp Glu Leu Lys Arg Gln Glu Val Ser Arg Leu
65                  70                  75                  80

Arg Met Leu Leu Lys Ala Lys Met Asp Ala Glu Gln Asp Pro Asn Val
                85                  90                  95

Gln Val Asp His Leu Asn Leu Leu Lys Gln Phe Glu His Leu Asp Pro
            100                 105                 110

Gln Asn Gln His Thr Phe Glu Ala Arg Asp Leu Glu Leu Leu Ile Gln
        115                 120                 125

Thr Ala Thr Arg Asp Leu Ala Gln Tyr Asp Ala Ala His His Glu Glu
130                 135                 140

Phe Lys Arg Tyr Glu Met Leu Lys Glu His Glu Arg Arg Tyr Leu
145                 150                 155                 160

Glu Ser Leu Gly Glu Glu Gln Arg Lys Glu Ala Glu Arg Lys Leu Glu
                165                 170                 175

Glu Gln Gln Arg Arg His Arg Glu His Pro Lys Val Asn Val Pro Gly
            180                 185                 190

Ser Gln Ala Gln Leu Lys Glu Val Trp Glu Glu Leu Asp Gly Leu Asp
        195                 200                 205

Pro Asn Arg Phe Asn Pro Lys Thr Phe Ile Leu His Asp Ile Asn
210                 215                 220

Ser Asp Gly Val Leu Asp Glu Gln Glu Leu Glu Ala Leu Phe Thr Lys
225                 230                 235                 240

Glu Leu Glu Lys Val Tyr Asp Pro Lys Asn Glu Glu Asp Asp Met Arg
                245                 250                 255

Glu Met Glu Glu Glu Arg Leu Arg Met Arg Glu His Val Met Lys Asn
            260                 265                 270
```

```
Val Asp Thr Asn Gln Asp Arg Leu Val Thr Leu Glu Glu Phe Leu Ala
            275                 280                 285

Ser Thr Gln Arg Lys Glu Phe Gly Asp Thr Glu Gly Trp Glu Thr
        290                 295                 300

Val Glu Met His Pro Ala Tyr Thr Glu Glu Leu Arg Arg Phe Glu
305                 310                 315                 320

Glu Glu Leu Ala Ala Arg Glu Ala Glu Leu Asn Ala Lys Ala Gln Arg
                325                 330                 335

Leu Ser Gln Glu Thr Glu Ala Leu Gly Arg Ser Gln Gly Arg Leu Glu
            340                 345                 350

Ala Gln Lys Arg Glu Leu Gln Gln Ala Val Leu His Met Glu Gln Arg
        355                 360                 365

Lys Gln Gln Gln Gln Gln Gln Gly His Lys Ala Pro Ala Ala His
            370                 375                 380

Pro Glu Gly Gln Leu Lys Phe His Pro Asp Thr Asp Val Pro Val
385                 390                 395                 400

Pro Ala Pro Ala Gly Asp Gln Lys Glu Val Asp Thr Ser Glu Lys Lys
                405                 410                 415

Leu Leu Glu Arg Leu Pro Glu Val Glu Val Pro Gln His Leu
            420                 425                 430

<210> SEQ ID NO 26
<211> LENGTH: 1293
<212> TYPE: DNA
<213> ORGANISM: Artificial
<220> FEATURE:
<223> OTHER INFORMATION: synthetic
<220> FEATURE:
<221> NAME/KEY: CDS
<222> LOCATION: (1)..(1131)

<400> SEQUENCE: 26 ggg gcg ccc aac aag gag gag acc cct gcg act gag agt ccc gac aca      48
Gly Ala Pro Asn Lys Glu Glu Thr Pro Ala Thr Glu Ser Pro Asp Thr
1               5                   10                  15 ggc ctg tac tac cac cgg tac ctc cag gag gtc atc gat gta ctg gag    96
Gly Leu Tyr Tyr His Arg Tyr Leu Gln Glu Val Ile Asp Val Leu Glu
            20                  25                  30 acg gat ggg cat ttc cga gag aag ctg cag gct gcc aat gcg gag gac   144
Thr Asp Gly His Phe Arg Glu Lys Leu Gln Ala Ala Asn Ala Glu Asp
        35                  40                  45 atc aag agc ggg aag ctg agc cga gag ctg gac ttt gtc agc cac cac   192
Ile Lys Ser Gly Lys Leu Ser Arg Glu Leu Asp Phe Val Ser His His
    50                  55                  60 gtc cgc acc aag ctg gat gag ctc aag cga cag gag gtg tca cgg ctg   240
Val Arg Thr Lys Leu Asp Glu Leu Lys Arg Gln Glu Val Ser Arg Leu
65                  70                  75                  80 cgg atg ctg ctc aag gcc aag atg gac gcc gag cag gat ccc aat gta   288
Arg Met Leu Leu Lys Ala Lys Met Asp Ala Glu Gln Asp Pro Asn Val
                85                  90                  95 cag gtg gat cat ctg aat ctc ctg aaa cag ttt gaa cac ctg gac cct   336
Gln Val Asp His Leu Asn Leu Leu Lys Gln Phe Glu His Leu Asp Pro
            100                 105                 110 cag aac cag cat aca ttc gag gcc cgc gac ctg gag ctg ctg atc cag   384
Gln Asn Gln His Thr Phe Glu Ala Arg Asp Leu Glu Leu Leu Ile Gln
        115                 120                 125 acg gcc acc cgg gac ctt gcc cag tac gac gca gcc cat cat gaa gag   432
Thr Ala Thr Arg Asp Leu Ala Gln Tyr Asp Ala Ala His His Glu Glu
    130                 135                 140
```

```
ttc aag cgc tac gag atg ctt aag gaa cac gag aga cgg cgt tat ctg    480
Phe Lys Arg Tyr Glu Met Leu Lys Glu His Glu Arg Arg Tyr Leu
145                 150                 155                 160 gag tca ctg gga gag gag cag aga aag gag gcg gag agg aag ctg gaa    528
Glu Ser Leu Gly Glu Glu Gln Arg Lys Glu Ala Glu Arg Lys Leu Glu
            165                 170                 175 gag caa cag cgc cgg cac cgc gag cac cct aaa gtc aac gtg cct ggc    576
Glu Gln Gln Arg Arg His Arg Glu His Pro Lys Val Asn Val Pro Gly
        180                 185                 190 agc caa gcc cag ttg aag gag gtg tgg gag gag ctg gat gga ctg gac    624
Ser Gln Ala Gln Leu Lys Glu Val Trp Glu Glu Leu Asp Gly Leu Asp
    195                 200                 205 ccc aac agg ttt aac ccc aag acc ttc ttc ata ctg cat gat atc aac    672
Pro Asn Arg Phe Asn Pro Lys Thr Phe Phe Ile Leu His Asp Ile Asn
210                 215                 220 agt gat ggt gtc ctg gat gag cag gag ctg gag gca ctc ttc acc aag    720
Ser Asp Gly Val Leu Asp Glu Gln Glu Leu Glu Ala Leu Phe Thr Lys
225                 230                 235                 240 gag ctg gag aaa gtg tac gac cca aag aat gag gag gac gac atg cgg    768
Glu Leu Glu Lys Val Tyr Asp Pro Lys Asn Glu Glu Asp Asp Met Arg
            245                 250                 255 gag atg gag gag gag cga ctg cgc atg cgg gag cat gtg atg aag aat    816
Glu Met Glu Glu Glu Arg Leu Arg Met Arg Glu His Val Met Lys Asn
        260                 265                 270 gtg gac acc aac cag gac cgc ctc gtg acc ctg gag gag ttc ctc gca    864
Val Asp Thr Asn Gln Asp Arg Leu Val Thr Leu Glu Glu Phe Leu Ala
    275                 280                 285 tcc act cag agg aag gag ttt ggg gac acc ggg gag ggc tgg gag aca    912
Ser Thr Gln Arg Lys Glu Phe Gly Asp Thr Gly Glu Gly Trp Glu Thr
290                 295                 300 gtg gag atg cac cct gcc tac acc gag gaa gag ctg agg cgc ttt gaa    960
Val Glu Met His Pro Ala Tyr Thr Glu Glu Glu Leu Arg Arg Phe Glu
305                 310                 315                 320 gag gag ctg gct gcc cgg gag gca gag ctg aat gcc aag gcc cag cgc   1008
Glu Glu Leu Ala Ala Arg Glu Ala Glu Leu Asn Ala Lys Ala Gln Arg
            325                 330                 335 ctc agc cag gag aca gag gct cta ggg cgg tcc cag ggc cgc ctg gag   1056
Leu Ser Gln Glu Thr Glu Ala Leu Gly Arg Ser Gln Gly Arg Leu Glu
        340                 345                 350 gcc cag aag aga gag ctg cag cag gct gtg ctg cac atg gag cag cgg   1104
Ala Gln Lys Arg Glu Leu Gln Gln Ala Val Leu His Met Glu Gln Arg
    355                 360                 365 aag cag cag cag cag cag cag caa taa cacaaggccc cggctgccca         1151
Lys Gln Gln Gln Gln Gln Gln
    370                 375 ccctgagggg cagctcaagt tccacccaga cacagacgat gtacctgtcc cagctccagc 1211 cggtgaccag aaggaggtgg acacttcaga aaagaaactt ctcgagcggc tccctgaggt 1271 tgaggtgccc cagcatctgt ga                                          1293

<210> SEQ ID NO 27
<211> LENGTH: 376
<212> TYPE: PRT
<213> ORGANISM: Artificial
<220> FEATURE:
<223> OTHER INFORMATION: Synthetic Construct

<400> SEQUENCE: 27

Gly Ala Pro Asn Lys Glu Glu Thr Pro Ala Thr Glu Ser Pro Asp Thr
1               5                   10                  15

Gly Leu Tyr Tyr His Arg Tyr Leu Gln Glu Val Ile Asp Val Leu Glu
```

20                  25                  30
Thr Asp Gly His Phe Arg Glu Lys Leu Gln Ala Ala Asn Ala Glu Asp
            35                  40                  45
Ile Lys Ser Gly Lys Leu Ser Arg Glu Leu Asp Phe Val Ser His His
        50                  55                  60
Val Arg Thr Lys Leu Asp Glu Leu Lys Arg Gln Glu Val Ser Arg Leu
65                  70                  75                  80
Arg Met Leu Leu Lys Ala Lys Met Asp Ala Glu Gln Asp Pro Asn Val
                85                  90                  95
Gln Val Asp His Leu Asn Leu Leu Lys Gln Phe Glu His Leu Asp Pro
            100                 105                 110
Gln Asn Gln His Thr Phe Glu Ala Arg Asp Leu Glu Leu Leu Ile Gln
        115                 120                 125
Thr Ala Thr Arg Asp Leu Ala Gln Tyr Asp Ala Ala His His Glu Glu
    130                 135                 140
Phe Lys Arg Tyr Glu Met Leu Lys Glu His Glu Arg Arg Arg Tyr Leu
145                 150                 155                 160
Glu Ser Leu Gly Glu Glu Gln Arg Lys Glu Ala Glu Arg Lys Leu Glu
                165                 170                 175
Glu Gln Gln Arg Arg His Arg Glu His Pro Lys Val Asn Val Pro Gly
            180                 185                 190
Ser Gln Ala Gln Leu Lys Glu Val Trp Glu Glu Leu Asp Gly Leu Asp
        195                 200                 205
Pro Asn Arg Phe Asn Pro Lys Thr Phe Phe Ile Leu His Asp Ile Asn
    210                 215                 220
Ser Asp Gly Val Leu Asp Glu Gln Glu Leu Glu Ala Leu Phe Thr Lys
225                 230                 235                 240
Glu Leu Glu Lys Val Tyr Asp Pro Lys Asn Glu Glu Asp Asp Met Arg
                245                 250                 255
Glu Met Glu Glu Glu Arg Leu Arg Met Arg Glu His Val Met Lys Asn
            260                 265                 270
Val Asp Thr Asn Gln Asp Arg Leu Val Thr Leu Glu Glu Phe Leu Ala
        275                 280                 285
Ser Thr Gln Arg Lys Glu Phe Gly Asp Thr Gly Glu Gly Trp Glu Thr
    290                 295                 300
Val Glu Met His Pro Ala Tyr Thr Glu Glu Glu Leu Arg Arg Phe Glu
305                 310                 315                 320
Glu Glu Leu Ala Ala Arg Glu Ala Glu Leu Asn Ala Lys Ala Gln Arg
                325                 330                 335
Leu Ser Gln Glu Thr Glu Ala Leu Gly Arg Ser Gln Gly Arg Leu Glu
            340                 345                 350
Ala Gln Lys Arg Glu Leu Gln Gln Ala Val Leu His Met Glu Gln Arg
        355                 360                 365
Lys Gln Gln Gln Gln Gln Gln
    370                 375

<210> SEQ ID NO 28
<211> LENGTH: 1293
<212> TYPE: DNA
<213> ORGANISM: Artificial
<220> FEATURE:
<223> OTHER INFORMATION: synthetic
<220> FEATURE:
<221> NAME/KEY: CDS
<222> LOCATION: (1)..(1107)

<400> SEQUENCE: 28

| | | | | | | | | | | | | | | | | |
|---|---|---|---|---|---|---|---|---|---|---|---|---|---|---|---|---|
| ggg | gcg | ccc | aac | aag | gag | gag | acc | cct | gcg | act | gag | agt | ccc | gac | aca | 48 |
| Gly | Ala | Pro | Asn | Lys | Glu | Glu | Thr | Pro | Ala | Thr | Glu | Ser | Pro | Asp | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggc | ctg | tac | tac | cac | cgg | tac | ctc | cag | gag | gtc | atc | gat | gta | ctg | gag | 96 |
| Gly | Leu | Tyr | Tyr | His | Arg | Tyr | Leu | Gln | Glu | Val | Ile | Asp | Val | Leu | Glu | |
| | | | 20 | | | | | 25 | | | | | 30 | | | |

| | | | | | | | | | | | | | | | | |
|---|---|---|---|---|---|---|---|---|---|---|---|---|---|---|---|---|
| acg | gat | ggg | cat | ttc | cga | gag | aag | ctg | cag | gct | gcc | aat | gcg | gag | gac | 144 |
| Thr | Asp | Gly | His | Phe | Arg | Glu | Lys | Leu | Gln | Ala | Ala | Asn | Ala | Glu | Asp | |
| | | 35 | | | | | 40 | | | | | 45 | | | | |

| | | | | | | | | | | | | | | | | |
|---|---|---|---|---|---|---|---|---|---|---|---|---|---|---|---|---|
| atc | aag | agc | ggg | aag | ctg | agc | cga | gag | ctg | gac | ttt | gtc | agc | cac | cac | 192 |
| Ile | Lys | Ser | Gly | Lys | Leu | Ser | Arg | Glu | Leu | Asp | Phe | Val | Ser | His | His | |
| | 50 | | | | | 55 | | | | | 60 | | | | | |

| | | | | | | | | | | | | | | | | |
|---|---|---|---|---|---|---|---|---|---|---|---|---|---|---|---|---|
| gtc | cgc | acc | aag | ctg | gat | gag | ctc | aag | cga | cag | gag | gtg | tca | cgg | ctg | 240 |
| Val | Arg | Thr | Lys | Leu | Asp | Glu | Leu | Lys | Arg | Gln | Glu | Val | Ser | Arg | Leu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cgg | atg | ctc | ctc | aag | gcc | aag | atg | gac | gcc | gag | cag | gat | ccc | aat | gta | 288 |
| Arg | Met | Leu | Leu | Lys | Ala | Lys | Met | Asp | Ala | Glu | Gln | Asp | Pro | Asn | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| cag | gtg | gat | cat | ctg | aat | ctc | ctg | aaa | cag | ttt | gaa | cac | ctg | gac | cct | 336 |
| Gln | Val | Asp | His | Leu | Asn | Leu | Leu | Lys | Gln | Phe | Glu | His | Leu | Asp | Pro | |
| | | | 100 | | | | | 105 | | | | | 110 | | | |

| | | | | | | | | | | | | | | | | |
|---|---|---|---|---|---|---|---|---|---|---|---|---|---|---|---|---|
| cag | aac | cag | cat | aca | ttc | gag | gcc | cgc | gac | ctg | gag | ctg | ctg | atc | cag | 384 |
| Gln | Asn | Gln | His | Thr | Phe | Glu | Ala | Arg | Asp | Leu | Glu | Leu | Leu | Ile | Gln | |
| | | 115 | | | | | 120 | | | | | 125 | | | | |

| | | | | | | | | | | | | | | | | |
|---|---|---|---|---|---|---|---|---|---|---|---|---|---|---|---|---|
| acg | gcc | acc | cgg | gac | ctt | gcc | cag | tac | gac | gca | gcc | cat | cat | gaa | gag | 432 |
| Thr | Ala | Thr | Arg | Asp | Leu | Ala | Gln | Tyr | Asp | Ala | Ala | His | His | Glu | Glu | |
| | 130 | | | | | 135 | | | | | 140 | | | | | |

| | | | | | | | | | | | | | | | | |
|---|---|---|---|---|---|---|---|---|---|---|---|---|---|---|---|---|
| ttc | aag | cgc | tac | gag | atg | ctt | aag | gaa | cac | gag | aga | cgg | cgt | tat | ctg | 480 |
| Phe | Lys | Arg | Tyr | Glu | Met | Leu | Lys | Glu | His | Glu | Arg | Arg | Arg | Tyr | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gag | tca | ctg | gga | gag | gag | cag | aga | aag | gag | gcg | gag | agg | aag | ctg | gaa | 528 |
| Glu | Ser | Leu | Gly | Glu | Glu | Gln | Arg | Lys | Glu | Ala | Glu | Arg | Lys | Leu | Glu | |
| | | | | 165 | | | | | 170 | | | | | 175 | | |

| | | | | | | | | | | | | | | | | |
|---|---|---|---|---|---|---|---|---|---|---|---|---|---|---|---|---|
| gag | caa | cag | cgc | cgg | cac | cgc | gag | cac | cct | aaa | gtc | aac | gtg | cct | ggc | 576 |
| Glu | Gln | Gln | Arg | Arg | His | Arg | Glu | His | Pro | Lys | Val | Asn | Val | Pro | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| agc | caa | gcc | cag | ttg | aag | gag | gtg | tgg | gag | gag | ctg | gat | gga | ctg | gac | 624 |
| Ser | Gln | Ala | Gln | Leu | Lys | Glu | Val | Trp | Glu | Glu | Leu | Asp | Gly | Leu | Asp | |
| | | 195 | | | | | 200 | | | | | 205 | | | | |

| | | | | | | | | | | | | | | | | |
|---|---|---|---|---|---|---|---|---|---|---|---|---|---|---|---|---|
| ccc | aac | agg | ttt | aac | ccc | aag | acc | ttc | ttc | ata | ctg | cat | gat | atc | aac | 672 |
| Pro | Asn | Arg | Phe | Asn | Pro | Lys | Thr | Phe | Phe | Ile | Leu | His | Asp | Ile | Asn | |
| | 210 | | | | | 215 | | | | | 220 | | | | | |

| | | | | | | | | | | | | | | | | |
|---|---|---|---|---|---|---|---|---|---|---|---|---|---|---|---|---|
| agt | gat | ggt | gtc | ctg | gat | gag | cag | gag | ctg | gag | gca | ctc | ttc | acc | aag | 720 |
| Ser | Asp | Gly | Val | Leu | Asp | Glu | Gln | Glu | Leu | Glu | Ala | Leu | Phe | Thr | Lys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gag | ctg | gag | aaa | gtg | tac | gac | cca | aag | aat | gag | gag | gac | gac | atg | cgg | 768 |
| Glu | Leu | Glu | Lys | Val | Tyr | Asp | Pro | Lys | Asn | Glu | Glu | Asp | Asp | Met | Arg | |
| | | | | 245 | | | | | 250 | | | | | 255 | | |

| | | | | | | | | | | | | | | | | |
|---|---|---|---|---|---|---|---|---|---|---|---|---|---|---|---|---|
| gag | atg | gag | gag | gag | cga | ctg | cgc | atg | cgg | gag | cat | gtg | atg | aag | aat | 816 |
| Glu | Met | Glu | Glu | Glu | Arg | Leu | Arg | Met | Arg | Glu | His | Val | Met | Lys | Asn | |
| | | | 260 | | | | | 265 | | | | | 270 | | | |

| | | | | | | | | | | | | | | | | |
|---|---|---|---|---|---|---|---|---|---|---|---|---|---|---|---|---|
| gtg | gac | acc | aac | cag | gac | cgc | ctc | gtg | acc | ctg | gag | gag | ttc | ctc | gca | 864 |
| Val | Asp | Thr | Asn | Gln | Asp | Arg | Leu | Val | Thr | Leu | Glu | Glu | Phe | Leu | Ala | |
| | | 275 | | | | | 280 | | | | | 285 | | | | |

| | | | | | | | | | | | | | | | | |
|---|---|---|---|---|---|---|---|---|---|---|---|---|---|---|---|---|
| tcc | act | cag | agg | aag | gag | ttt | ggg | gac | acc | ggg | gag | ggc | tgg | gag | aca | 912 |
| Ser | Thr | Gln | Arg | Lys | Glu | Phe | Gly | Asp | Thr | Gly | Glu | Gly | Trp | Glu | Thr | |
| | 290 | | | | | 295 | | | | | 300 | | | | | |

| | | | | | | | | | | | | | | | | |
|---|---|---|---|---|---|---|---|---|---|---|---|---|---|---|---|---|
| gtg | gag | atg | cac | cct | gcc | tac | acc | gag | gaa | gag | ctg | agg | cgc | ttt | gaa | 960 |
| Val | Glu | Met | His | Pro | Ala | Tyr | Thr | Glu | Glu | Glu | Leu | Arg | Arg | Phe | Glu | |
| 305 | | | | | 310 | | | | | 315 | | | | | 320 | |

```
gag gag ctg gct gcc cgg gag gca gag ctg aat gcc aag gcc cag cgc    1008
Glu Glu Leu Ala Ala Arg Glu Ala Glu Leu Asn Ala Lys Ala Gln Arg
            325                 330                 335 ctc agc cag gag aca gag gct cta ggg cgg tcc cag ggc cgc ctg gag    1056
Leu Ser Gln Glu Thr Glu Ala Leu Gly Arg Ser Gln Gly Arg Leu Glu
            340                 345                 350 gcc cag aag aga gag ctg cag cag gct gtg ctg cac atg gag cag cgg    1104
Ala Gln Lys Arg Glu Leu Gln Gln Ala Val Leu His Met Glu Gln Arg
        355                 360                 365 taa cagcagcagc agcagcagca aggccacaag gccccggctg cccaccctga         1157
ggggcagctc aagttccacc cagacacaga cgatgtacct gtcccagctc agccggtga   1217 ccagaaggag gtggacactt cagaaaagaa acttctcgag cggctccctg aggttgaggt  1277
gccccagcat ctgtga                                                  1293

<210> SEQ ID NO 29
<211> LENGTH: 368
<212> TYPE: PRT
<213> ORGANISM: Artificial
<220> FEATURE:
<223> OTHER INFORMATION: Synthetic Construct

<400> SEQUENCE: 29

Gly Ala Pro Asn Lys Glu Glu Thr Pro Ala Thr Glu Ser Pro Asp Thr
1               5                   10                  15

Gly Leu Tyr Tyr His Arg Tyr Leu Gln Glu Val Ile Asp Val Leu Glu
            20                  25                  30

Thr Asp Gly His Phe Arg Glu Lys Leu Gln Ala Ala Asn Ala Glu Asp
        35                  40                  45

Ile Lys Ser Gly Lys Leu Ser Arg Glu Leu Asp Phe Val Ser His His
    50                  55                  60

Val Arg Thr Lys Leu Asp Glu Leu Lys Arg Gln Glu Val Ser Arg Leu
65                  70                  75                  80

Arg Met Leu Leu Lys Ala Lys Met Asp Ala Glu Gln Asp Pro Asn Val
                85                  90                  95

Gln Val Asp His Leu Asn Leu Leu Lys Gln Phe Glu His Leu Asp Pro
            100                 105                 110

Gln Asn Gln His Thr Phe Glu Ala Arg Asp Leu Glu Leu Leu Ile Gln
        115                 120                 125

Thr Ala Thr Arg Asp Leu Ala Gln Tyr Asp Ala Ala His His Glu Glu
    130                 135                 140

Phe Lys Arg Tyr Glu Met Leu Lys Glu His Glu Arg Arg Tyr Leu
145                 150                 155                 160

Glu Ser Leu Gly Glu Glu Gln Arg Lys Glu Ala Glu Arg Lys Leu Glu
                165                 170                 175

Glu Gln Gln Arg Arg His Arg Glu His Pro Lys Val Asn Val Pro Gly
            180                 185                 190

Ser Gln Ala Gln Leu Lys Glu Val Trp Glu Glu Leu Asp Gly Leu Asp
        195                 200                 205

Pro Asn Arg Phe Asn Pro Lys Thr Phe Phe Ile Leu His Asp Ile Asn
    210                 215                 220

Ser Asp Gly Val Leu Asp Glu Gln Glu Leu Glu Ala Leu Phe Thr Lys
225                 230                 235                 240

Glu Leu Glu Lys Val Tyr Asp Pro Lys Asn Glu Glu Asp Asp Met Arg
                245                 250                 255

Glu Met Glu Glu Glu Arg Leu Arg Met Arg Glu His Val Met Lys Asn
```

```
                    260                 265                 270
Val Asp Thr Asn Gln Asp Arg Leu Val Thr Leu Glu Glu Phe Leu Ala
            275                 280                 285

Ser Thr Gln Arg Lys Glu Phe Gly Asp Thr Gly Glu Gly Trp Glu Thr
        290                 295                 300

Val Glu Met His Pro Ala Tyr Thr Glu Glu Glu Leu Arg Arg Phe Glu
305                 310                 315                 320

Glu Glu Leu Ala Ala Arg Glu Ala Glu Leu Asn Ala Lys Ala Gln Arg
                325                 330                 335

Leu Ser Gln Glu Thr Glu Ala Leu Gly Arg Ser Gln Gly Arg Leu Glu
            340                 345                 350

Ala Gln Lys Arg Glu Leu Gln Gln Ala Val Leu His Met Glu Gln Arg
        355                 360                 365

<210> SEQ ID NO 30
<211> LENGTH: 1293
<212> TYPE: DNA
<213> ORGANISM: Artificial
<220> FEATURE:
<223> OTHER INFORMATION: synthetic
<220> FEATURE:
<221> NAME/KEY: CDS
<222> LOCATION: (1)..(906)

<400> SEQUENCE: 30
```

| | |
|---|---|
| ggg gcg ccc aac aag gag gag acc cct gcg act gag agt ccc gac aca<br>Gly Ala Pro Asn Lys Glu Glu Thr Pro Ala Thr Glu Ser Pro Asp Thr<br>1               5                  10                  15 | 48 |
| ggc ctg tac tac cac cgg tac ctc cag gag gtc atc gat gta ctg gag<br>Gly Leu Tyr Tyr His Arg Tyr Leu Gln Glu Val Ile Asp Val Leu Glu<br>                20                  25                  30 | 96 |
| acg gat ggg cat ttc cga gag aag ctg cag gct gcc aat gcg gag gac<br>Thr Asp Gly His Phe Arg Glu Lys Leu Gln Ala Ala Asn Ala Glu Asp<br>            35                  40                  45 | 144 |
| atc aag agc ggg aag ctg agc cga gag ctg gac ttt gtc agc cac cac<br>Ile Lys Ser Gly Lys Leu Ser Arg Glu Leu Asp Phe Val Ser His His<br>        50                  55                  60 | 192 |
| gtc cgc acc aag ctg gat gag ctc aag cga cag gag gtg tca cgg ctg<br>Val Arg Thr Lys Leu Asp Glu Leu Lys Arg Gln Glu Val Ser Arg Leu<br>65                  70                  75                  80 | 240 |
| cgg atg ctg ctc aag gcc aag atg gac gcc gag cag gat ccc aat gta<br>Arg Met Leu Leu Lys Ala Lys Met Asp Ala Glu Gln Asp Pro Asn Val<br>                85                  90                  95 | 288 |
| cag gtg gat cat ctg aat ctc ctg aaa cag ttt gaa cac ctg gac cct<br>Gln Val Asp His Leu Asn Leu Leu Lys Gln Phe Glu His Leu Asp Pro<br>            100                 105                 110 | 336 |
| cag aac cag cat aca ttc gag gcc cgc gac ctg gag ctg ctg atc cag<br>Gln Asn Gln His Thr Phe Glu Ala Arg Asp Leu Glu Leu Leu Ile Gln<br>        115                 120                 125 | 384 |
| acg gcc acc cgg gac ctt gcc cag tac gac gca gcc cat cat gaa gag<br>Thr Ala Thr Arg Asp Leu Ala Gln Tyr Asp Ala Ala His His Glu Glu<br>130                 135                 140 | 432 |
| ttc aag cgc tac gag atg ctt aag gaa cac gag aga cgg cgt tat ctg<br>Phe Lys Arg Tyr Glu Met Leu Lys Glu His Glu Arg Arg Arg Tyr Leu<br>145                 150                 155                 160 | 480 |
| gag tca ctg gga gag gag cag aga aag gag gcg gag agg aag ctg gaa<br>Glu Ser Leu Gly Glu Glu Gln Arg Lys Glu Ala Glu Arg Lys Leu Glu<br>                165                 170                 175 | 528 |
| gag caa cag cgc cgg cac cgc gag cac cct aaa gtc aac gtg cct ggc<br>Glu Gln Gln Arg Arg His Arg Glu His Pro Lys Val Asn Val Pro Gly<br>            180                 185                 190 | 576 |

```
agc caa gcc cag ttg aag gag gtg tgg gag gag ctg gat gga ctg gac       624
Ser Gln Ala Gln Leu Lys Glu Val Trp Glu Glu Leu Asp Gly Leu Asp
        195                 200                 205 ccc aac agg ttt aac ccc aag acc ttc ttc ata ctg cat gat atc aac       672
Pro Asn Arg Phe Asn Pro Lys Thr Phe Phe Ile Leu His Asp Ile Asn
    210                 215                 220 agt gat ggt gtc ctg gat gag cag gag ctg gag gca ctc ttc acc aag       720
Ser Asp Gly Val Leu Asp Glu Gln Glu Leu Glu Ala Leu Phe Thr Lys
225                 230                 235                 240 gag ctg gag aaa gtg tac gac cca aag aat gag gag gac gac atg cgg       768
Glu Leu Glu Lys Val Tyr Asp Pro Lys Asn Glu Glu Asp Asp Met Arg
                245                 250                 255 gag atg gag gag gag cga ctg cgc atg cgg gag cat gtg atg aag aat       816
Glu Met Glu Glu Glu Arg Leu Arg Met Arg Glu His Val Met Lys Asn
            260                 265                 270 gtg gac acc aac cag gac cgc ctc gtg acc ctg gag gag ttc ctc gca       864
Val Asp Thr Asn Gln Asp Arg Leu Val Thr Leu Glu Glu Phe Leu Ala
        275                 280                 285 tcc act cag agg aag gag ttt ggg gac acc ggg gag ggc taa               906
Ser Thr Gln Arg Lys Glu Phe Gly Asp Thr Gly Glu Gly
    290                 295                 300 gagacagtgg agatgcaccc tgcctacacc gaggaagagc tgaggcgctt tgaagaggag     966
ctggctgccc gggaggcaga gctgaatgcc aaggcccagc gcctcagcca ggagacagag    1026
gctctagggc ggtcccaggg ccgcctggag gcccagaaga gagagctgca gcaggctgtg    1086
ctgcacatgg agcagcggaa gcagcagcag cagcagcagc aaggccacaa ggccccggct    1146
gcccaccctg aggggcagct caagttccac ccagacacag acgatgtacc tgtcccagct    1206
ccagccggtg accagaagga ggtggacact tcagaaaaga aacttctcga gcggctccct    1266
gaggttgagg tgccccagca tctgtga                                        1293

<210> SEQ ID NO 31
<211> LENGTH: 301
<212> TYPE: PRT
<213> ORGANISM: Artificial
<220> FEATURE:
<223> OTHER INFORMATION: Synthetic Construct

<400> SEQUENCE: 31

Gly Ala Pro Asn Lys Glu Glu Thr Pro Ala Thr Glu Ser Pro Asp Thr
1               5                   10                  15

Gly Leu Tyr Tyr His Arg Tyr Leu Gln Glu Val Ile Asp Val Leu Glu
            20                  25                  30

Thr Asp Gly His Phe Arg Glu Lys Leu Gln Ala Ala Asn Ala Glu Asp
        35                  40                  45

Ile Lys Ser Gly Lys Leu Ser Arg Glu Leu Asp Phe Val Ser His His
    50                  55                  60

Val Arg Thr Lys Leu Asp Glu Leu Lys Arg Gln Glu Val Ser Arg Leu
65                  70                  75                  80

Arg Met Leu Leu Lys Ala Lys Met Asp Ala Glu Gln Asp Pro Asn Val
                85                  90                  95

Gln Val Asp His Leu Asn Leu Leu Lys Gln Phe Glu His Leu Asp Pro
            100                 105                 110

Gln Asn Gln His Thr Phe Glu Ala Arg Asp Leu Glu Leu Leu Ile Gln
        115                 120                 125

Thr Ala Thr Arg Asp Leu Ala Gln Tyr Asp Ala Ala His His Glu Glu
    130                 135                 140
```

```
Phe Lys Arg Tyr Glu Met Leu Lys Glu His Glu Arg Arg Tyr Leu
145                 150                 155                 160

Glu Ser Leu Gly Glu Gln Arg Lys Glu Ala Glu Arg Lys Leu Glu
            165                 170                 175

Glu Gln Gln Arg Arg His Arg Glu His Pro Lys Val Asn Val Pro Gly
            180                 185                 190

Ser Gln Ala Gln Leu Lys Glu Val Trp Glu Glu Leu Asp Gly Leu Asp
            195                 200                 205

Pro Asn Arg Phe Asn Pro Lys Thr Phe Phe Ile Leu His Asp Ile Asn
            210                 215                 220

Ser Asp Gly Val Leu Asp Glu Gln Glu Leu Glu Ala Leu Phe Thr Lys
225                 230                 235                 240

Glu Leu Glu Lys Val Tyr Asp Pro Lys Asn Glu Glu Asp Asp Met Arg
            245                 250                 255

Glu Met Glu Glu Glu Arg Leu Arg Met Arg Glu His Val Met Lys Asn
            260                 265                 270

Val Asp Thr Asn Gln Asp Arg Leu Val Thr Leu Glu Glu Phe Leu Ala
            275                 280                 285

Ser Thr Gln Arg Lys Phe Gly Asp Thr Gly Glu Gly
            290                 295                 300

<210> SEQ ID NO 32
<211> LENGTH: 504
<212> TYPE: DNA
<213> ORGANISM: Artificial
<220> FEATURE:
<223> OTHER INFORMATION: synthetic
<220> FEATURE:
<221> NAME/KEY: CDS
<222> LOCATION: (1)..(504)

<400> SEQUENCE: 32 gag gag ctg gat gga ctg gac ccc aac agg ttt aac ccc aag acc ttc       48
Glu Glu Leu Asp Gly Leu Asp Pro Asn Arg Phe Asn Pro Lys Thr Phe
1               5                   10                  15 ttc ata ctg cat gat atc aac agt gat ggt gtc ctg gat gag cag gag       96
Phe Ile Leu His Asp Ile Asn Ser Asp Gly Val Leu Asp Glu Gln Glu
                20                  25                  30 ctg gag gca ctc ttc acc aag gag ctg gag aaa gtg tac gac cca aag      144
Leu Glu Ala Leu Phe Thr Lys Glu Leu Glu Lys Val Tyr Asp Pro Lys
            35                  40                  45 aat gag gag gac gac atg cgg gag atg gag gag cga ctc gcc atg           192
Asn Glu Glu Asp Asp Met Arg Glu Met Glu Glu Arg Leu Arg Met
        50                  55                  60 cgg gag cat gtg atg aag aat gtg gac acc aac cag gac cgc ctc gtg      240
Arg Glu His Val Met Lys Asn Val Asp Thr Asn Gln Asp Arg Leu Val
65                  70                  75                  80 acc ctg gag gag ttc ctc gca tcc act cag agg aag gag ttt ggg gac      288
Thr Leu Glu Glu Phe Leu Ala Ser Thr Gln Arg Lys Glu Phe Gly Asp
                85                  90                  95 acc ggg gag ggc tgg gag aca gtg gag atg cac cct gcc tac acc gag      336
Thr Gly Glu Gly Trp Glu Thr Val Glu Met His Pro Ala Tyr Thr Glu
            100                 105                 110 gaa gag ctg agg cgc ttt gaa gag gag ctg gct gcc cgg gag gca gag      384
Glu Glu Leu Arg Arg Phe Glu Glu Glu Leu Ala Ala Arg Glu Ala Glu
            115                 120                 125 ctg aat gcc aag gcc cag cgc ctc agc cag gag aca gag gct cta ggg      432
Leu Asn Ala Lys Ala Gln Arg Leu Ser Gln Glu Thr Glu Ala Leu Gly
        130                 135                 140 cgg tcc cag ggc cgc ctg gag gcc cag aag aga gag ctg cag cag gct      480
```

```
Arg Ser Gln Gly Arg Leu Glu Ala Gln Lys Arg Glu Leu Gln Gln Ala
145                 150                 155                 160 gtg ctg cac atg gag cag cgg aag                                      504
Val Leu His Met Glu Gln Arg Lys
                165
```

<210> SEQ ID NO 33
<211> LENGTH: 168
<212> TYPE: PRT
<213> ORGANISM: Artificial
<220> FEATURE:
<223> OTHER INFORMATION: Synthetic Construct

<400> SEQUENCE: 33

```
Glu Glu Leu Asp Gly Leu Asp Pro Asn Arg Phe Asn Pro Lys Thr Phe
1               5                   10                  15

Phe Ile Leu His Asp Ile Asn Ser Asp Gly Val Leu Asp Glu Gln Glu
            20                  25                  30

Leu Glu Ala Leu Phe Thr Lys Glu Leu Glu Lys Val Tyr Asp Pro Lys
        35                  40                  45

Asn Glu Glu Asp Asp Met Arg Glu Met Glu Glu Arg Leu Arg Met
50                  55                  60

Arg Glu His Val Met Lys Asn Val Asp Thr Asn Gln Asp Arg Leu Val
65                  70                  75                  80

Thr Leu Glu Glu Phe Leu Ala Ser Thr Gln Arg Lys Glu Phe Gly Asp
                85                  90                  95

Thr Gly Glu Gly Trp Glu Thr Val Glu Met His Pro Ala Tyr Thr Glu
            100                 105                 110

Glu Glu Leu Arg Arg Phe Glu Glu Leu Ala Ala Arg Glu Ala Glu
        115                 120                 125

Leu Asn Ala Lys Ala Gln Arg Leu Ser Gln Glu Thr Glu Ala Leu Gly
130                 135                 140

Arg Ser Gln Gly Arg Leu Glu Ala Gln Lys Arg Glu Leu Gln Gln Ala
145                 150                 155                 160

Val Leu His Met Glu Gln Arg Lys
                165
```

<210> SEQ ID NO 34
<211> LENGTH: 1293
<212> TYPE: DNA
<213> ORGANISM: Artificial
<220> FEATURE:
<223> OTHER INFORMATION: synthetic
<220> FEATURE:
<221> NAME/KEY: CDS
<222> LOCATION: (1)..(627)

<400> SEQUENCE: 34

```
ggg gcg ccc aac aag gag gag acc cct gcg act gag agt ccc gac aca      48
Gly Ala Pro Asn Lys Glu Glu Thr Pro Ala Thr Glu Ser Pro Asp Thr
1               5                   10                  15 ggc ctg tac tac cac cgg tac ctc cag gag gtc atc gat gta ctg gag      96
Gly Leu Tyr Tyr His Arg Tyr Leu Gln Glu Val Ile Asp Val Leu Glu
            20                  25                  30 acg gat ggg cat ttc cga gag aag ctg cag gct gcc aat gcg gag gac      144
Thr Asp Gly His Phe Arg Glu Lys Leu Gln Ala Ala Asn Ala Glu Asp
        35                  40                  45 atc aag agc ggg aag ctg agc cga gag ctg gac ttt gtc agc cac cac      192
Ile Lys Ser Gly Lys Leu Ser Arg Glu Leu Asp Phe Val Ser His His
50                  55                  60 gtc cgc acc aag ctg gat gag ctc aag cga cag gag gtg tca cgg ctg      240
```

```
Val Arg Thr Lys Leu Asp Glu Leu Lys Arg Gln Glu Val Ser Arg Leu
 65                  70                  75                  80 cgg atg ctg ctc aag gcc aag atg gac gcc gag cag gat ccc aat gta     288
Arg Met Leu Leu Lys Ala Lys Met Asp Ala Glu Gln Asp Pro Asn Val
                 85                  90                  95 cag gtg gat cat ctg aat ctc ctg aaa cag ttt gaa cac ctg gac cct     336
Gln Val Asp His Leu Asn Leu Leu Lys Gln Phe Glu His Leu Asp Pro
            100                 105                 110 cag aac cag cat aca ttc gag gcc cgc gac ctg gag ctg ctg atc cag     384
Gln Asn Gln His Thr Phe Glu Ala Arg Asp Leu Glu Leu Leu Ile Gln
        115                 120                 125 acg gcc acc cgg gac ctt gcc cag tac gac gca gcc cat cat gaa gag     432
Thr Ala Thr Arg Asp Leu Ala Gln Tyr Asp Ala Ala His His Glu Glu
    130                 135                 140 ttc aag cgc tac gag atg ctt aag gaa cac gag aga cgg cgt tat ctg     480
Phe Lys Arg Tyr Glu Met Leu Lys Glu His Glu Arg Arg Arg Tyr Leu
145                 150                 155                 160 gag tca ctg gga gag gag cag aga aag gag gcg gag agg aag ctg gaa     528
Glu Ser Leu Gly Glu Glu Gln Arg Lys Glu Ala Glu Arg Lys Leu Glu
                165                 170                 175 gag caa cag cgc cgg cac cgc gag cac cct aaa gtc aac gtg cct ggc     576
Glu Gln Gln Arg Arg His Arg Glu His Pro Lys Val Asn Val Pro Gly
            180                 185                 190 agc caa gcc cag ttg aag gag gtg tgg gag gag ctg gat gga ctg gac     624
Ser Gln Ala Gln Leu Lys Glu Val Trp Glu Glu Leu Asp Gly Leu Asp
        195                 200                 205 taa aacaggttta accccaagac cttcttcata ctgcatgata tcaacagtga          677
tggtgtcctg gatgagcagg agctggaggc actcttcacc aaggagctgg agaaagtgta   737
cgacccaaag aatgaggagg acgacatgcg ggagatggag gaggagcgac tgcgcatgcg   797
ggagcatgtg atgaagaatg tggacaccaa ccaggaccgc ctcgtgaccc tggaggagtt   857
cctcgcatcc actcagagga aggagtttgg ggacaccggg gagggctggg agacagtgga   917
gatgcaccct gcctacaccg aggaagagct gaggcgcttt gaagaggagc tggctgcccg   977
ggaggcagag ctgaatgcca aggcccagcg cctcagccag gagacagagg ctctagggcg  1037
gtcccagggc cgcctggagg cccagaagag agagctgcag caggctgtgc tgcacatgga  1097
gcagcggaag cagcagcagc agcagcagca aggccacaag gccccggctg cccacccctg  1157
ggggcagctc aagttccacc cagacacaga cgatgtacct gtcccagctc agccggtga   1217 ccagaaggag gtggacactt cagaaaagaa acttctcgag cggctccctg aggttgaggt  1277
gccccagcat ctgtga                                                 1293

<210> SEQ ID NO 35
<211> LENGTH: 208
<212> TYPE: PRT
<213> ORGANISM: Artificial
<220> FEATURE:
<223> OTHER INFORMATION: Synthetic Construct

<400> SEQUENCE: 35

Gly Ala Pro Asn Lys Glu Glu Thr Pro Ala Thr Glu Ser Pro Asp Thr
1               5                  10                  15

Gly Leu Tyr Tyr His Arg Tyr Leu Gln Glu Val Ile Asp Val Leu Glu
            20                  25                  30

Thr Asp Gly His Phe Arg Glu Lys Leu Gln Ala Ala Asn Ala Glu Asp
        35                  40                  45

Ile Lys Ser Gly Lys Leu Ser Arg Glu Leu Asp Phe Val Ser His His
    50                  55                  60
```

Val Arg Thr Lys Leu Asp Glu Leu Lys Arg Gln Glu Val Ser Arg Leu
 65                  70                  75                  80

Arg Met Leu Leu Lys Ala Lys Met Asp Ala Glu Gln Asp Pro Asn Val
                 85                  90                  95

Gln Val Asp His Leu Asn Leu Lys Gln Phe Glu His Leu Asp Pro
            100                 105                 110

Gln Asn Gln His Thr Phe Glu Ala Arg Asp Leu Glu Leu Leu Ile Gln
            115                 120                 125

Thr Ala Thr Arg Asp Leu Ala Gln Tyr Asp Ala Ala His His Glu Glu
            130                 135                 140

Phe Lys Arg Tyr Glu Met Leu Lys Glu His Glu Arg Arg Tyr Leu
145                 150                 155                 160

Glu Ser Leu Gly Glu Glu Gln Arg Lys Glu Ala Glu Arg Lys Leu Glu
                165                 170                 175

Glu Gln Gln Arg Arg His Arg Glu His Pro Lys Val Asn Val Pro Gly
            180                 185                 190

Ser Gln Ala Gln Leu Lys Glu Val Trp Glu Glu Leu Asp Gly Leu Asp
            195                 200                 205

<210> SEQ ID NO 36
<211> LENGTH: 8
<212> TYPE: PRT
<213> ORGANISM: Artificial
<220> FEATURE:
<223> OTHER INFORMATION: synthetic

<400> SEQUENCE: 36

Leu Glu Val Leu Phe Gln Gly Pro
1               5

<210> SEQ ID NO 37
<211> LENGTH: 6
<212> TYPE: PRT
<213> ORGANISM: Artificial
<220> FEATURE:
<223> OTHER INFORMATION: synthetic

<400> SEQUENCE: 37

Gly Pro His Met Ala Ser
1               5

<210> SEQ ID NO 38
<211> LENGTH: 21
<212> TYPE: PRT
<213> ORGANISM: Artificial
<220> FEATURE:
<223> OTHER INFORMATION: synthetic

<400> SEQUENCE: 38

His His His His His His Ser Ser Gly Leu Glu Val Leu Phe Gln Gly
1               5                   10                  15

Pro His Met Ala Ser
            20

<210> SEQ ID NO 39
<211> LENGTH: 451
<212> TYPE: PRT
<213> ORGANISM: Artificial
<220> FEATURE:
<223> OTHER INFORMATION: synthetic

<400> SEQUENCE: 39

-continued

```
His His His His His His Ser Ser Gly Leu Glu Val Leu Phe Gln Gly
1               5                   10                  15

Pro His Met Ala Ser Gly Ala Pro Asn Lys Glu Thr Pro Ala Thr
            20                  25                  30

Glu Ser Pro Asp Thr Gly Leu Tyr Tyr His Arg Tyr Leu Gln Glu Val
        35                  40                  45

Ile Asp Val Leu Glu Thr Asp Gly His Phe Arg Glu Lys Leu Gln Ala
50                  55                  60

Ala Asn Ala Glu Asp Ile Lys Ser Gly Lys Leu Ser Arg Glu Leu Asp
65                  70                  75                  80

Phe Val Ser His His Val Arg Thr Lys Leu Asp Glu Leu Lys Arg Gln
                85                  90                  95

Glu Val Ser Arg Leu Arg Met Leu Leu Lys Ala Lys Met Asp Ala Glu
            100                 105                 110

Gln Asp Pro Asn Val Gln Val Asp His Leu Asn Leu Leu Lys Gln Phe
        115                 120                 125

Glu His Leu Asp Pro Gln Asn Gln His Thr Phe Glu Ala Arg Asp Leu
    130                 135                 140

Glu Leu Leu Ile Gln Thr Ala Thr Arg Asp Leu Ala Gln Tyr Asp Ala
145                 150                 155                 160

Ala His His Glu Glu Phe Lys Arg Tyr Glu Met Leu Lys Glu His Glu
                165                 170                 175

Arg Arg Arg Tyr Leu Glu Ser Leu Gly Glu Glu Gln Arg Lys Glu Ala
            180                 185                 190

Glu Arg Lys Leu Glu Glu Gln Gln Arg Arg His Arg Glu His Pro Lys
        195                 200                 205

Val Asn Val Pro Gly Ser Gln Ala Gln Leu Lys Glu Val Trp Glu Glu
    210                 215                 220

Leu Asp Gly Leu Asp Pro Asn Arg Phe Asn Pro Lys Thr Phe Phe Ile
225                 230                 235                 240

Leu His Asp Ile Asn Ser Asp Gly Val Leu Asp Gln Glu Leu Glu
                245                 250                 255

Ala Leu Phe Thr Lys Glu Leu Glu Lys Val Tyr Asp Pro Lys Asn Glu
            260                 265                 270

Glu Asp Asp Met Arg Glu Met Glu Glu Glu Arg Leu Arg Met Arg Glu
        275                 280                 285

His Val Met Lys Asn Val Asp Thr Asn Gln Asp Arg Leu Val Thr Leu
    290                 295                 300

Glu Glu Phe Leu Ala Ser Thr Gln Arg Lys Glu Phe Gly Asp Thr Gly
305                 310                 315                 320

Glu Gly Trp Glu Thr Val Glu Met His Pro Ala Tyr Thr Glu Glu Glu
                325                 330                 335

Leu Arg Arg Phe Glu Glu Glu Leu Ala Ala Arg Glu Ala Glu Leu Asn
            340                 345                 350

Ala Lys Ala Gln Arg Leu Ser Gln Glu Thr Glu Ala Leu Gly Arg Ser
        355                 360                 365

Gln Gly Arg Leu Glu Ala Gln Lys Arg Glu Leu Gln Gln Ala Val Leu
    370                 375                 380

His Met Glu Gln Arg Lys Gln Gln Gln Gln Gln Gln Gly His Lys
385                 390                 395                 400

Ala Pro Ala Ala His Pro Glu Gly Gln Leu Lys Phe His Pro Asp Thr
                405                 410                 415

Asp Asp Val Pro Val Pro Ala Pro Ala Gly Asp Gln Lys Glu Val Asp
            420                 425                 430
```

```
Thr Ser Glu Lys Lys Leu Leu Glu Arg Leu Pro Glu Val Glu Val Pro
        435                 440                 445
Gln His Leu
    450
```